US011925112B2

(12) United States Patent
Lee et al.

(10) Patent No.: US 11,925,112 B2
(45) Date of Patent: Mar. 5, 2024

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Je Woo Lee, Cheonan-si (KR); Hyun Ji Oh, Cheonan-si (KR); Sun Hee Lee, Cheonan-si (KR); Won Sam Kim, Cheonan-si (KR); Byoung Yeop Kang, Cheonan-si (KR)

(73) Assignee: DUK SAN NEOLUX CO., LTD., Cheonan-si (KR)

(*) Notice: Subject to any disclaimer, the term of this patent is extended or adjusted under 35 U.S.C. 154(b) by 0 days.

(21) Appl. No.: 18/062,370

(22) Filed: Dec. 6, 2022

(65) Prior Publication Data

US 2023/0189639 A1 Jun. 15, 2023

Related U.S. Application Data

(63) Continuation-in-part of application No. 17/756,193, filed as application No. PCT/KR2020/016272 on Nov. 18, 2020.

(30) Foreign Application Priority Data

Nov. 19, 2019 (KR) ........................ 10-2019-0148780
Aug. 14, 2020 (KR) ........................ 10-2020-0102536

(51) Int. Cl.
*C07D 407/12* (2006.01)
*C07D 405/12* (2006.01)
(Continued)

(52) U.S. Cl.
CPC ......... *H10K 85/636* (2023.02); *C07D 405/12* (2013.01); *C07D 405/14* (2013.01);
(Continued)

(58) Field of Classification Search
CPC ................ C07D 407/12; C07D 409/12; H10K 85/6574; H10K 85/6576; H10K 85/633
See application file for complete search history.

(56) References Cited

U.S. PATENT DOCUMENTS

2015/0295181 A1 10/2015 Mujica-Fernaud et al.
2017/0084843 A1 3/2017 Yun et al.
(Continued)

FOREIGN PATENT DOCUMENTS

CN 105778891 A 7/2016
CN 105906640 A 8/2016
(Continued)

OTHER PUBLICATIONS

Matsumoto et al., "27.5L: Late-News Paper: Multiphoton Organic EL device having Charge Generation Layer", SID 03 DIGEST, 2003, pp. 979-981.
(Continued)

*Primary Examiner* — Vu A Nguyen
(74) *Attorney, Agent, or Firm* — Vorys, Sater, Seymour and Pease LLP; Mih Suhn Koh

(57) ABSTRACT

The present invention provides a novel compound that can improve the luminous efficiency, stability and life span of the element, an organic electronic element using the same, and an electronic device thereof.

13 Claims, 2 Drawing Sheets

(51) Int. Cl.

| | |
|---|---|
| ***C07D 405/14*** | (2006.01) |
| ***C07D 409/12*** | (2006.01) |
| ***C07D 409/14*** | (2006.01) |
| ***H01L 51/00*** | (2006.01) |
| ***H01L 51/50*** | (2006.01) |
| ***H10K 85/60*** | (2023.01) |
| *H10K 30/80* | (2023.01) |
| *H10K 71/00* | (2023.01) |

(52) U.S. Cl.

CPC ......... *C07D 409/12* (2013.01); *C07D 409/14* (2013.01); *H10K 85/633* (2023.02); *H10K 30/865* (2023.02); *H10K 71/00* (2023.02); *H10K 71/311* (2023.02); *H10K 85/6574* (2023.02); *H10K 85/6576* (2023.02)

(56) References Cited

U.S. PATENT DOCUMENTS

| | | | |
|---|---|---|---|
| 2017/0365794 | A1 | 12/2017 | Park et al. |
| 2018/0026187 | A1 | 1/2018 | Park et al. |
| 2019/0088879 | A1 | 3/2019 | Haketa et al. |
| 2019/0363263 | A1 | 11/2019 | Uno |
| 2020/0044160 | A1 | 2/2020 | Voges et al. |

FOREIGN PATENT DOCUMENTS

| | | | | | |
|---|---|---|---|---|---|
| CN | 109867652 | A | | 6/2019 | |
| CN | 114641870 | A | | 6/2022 | |
| EP | 3 348 552 | A1 | | 7/2018 | |
| EP | 3 764 416 | A1 | | 1/2021 | |
| KR | 10-2013-0076842 | A | | 7/2013 | |
| KR | 10-2015-0083917 | A | | 7/2015 | |
| KR | 10-2017-0138799 | A | | 12/2017 | |
| KR | 20170138799 | A | * | 12/2017 | ........... C07D 307/94 |
| KR | 10-2018-0112962 | A | | 10/2018 | |
| KR | 10-2019-0015211 | A | | 2/2019 | |
| KR | 10-2019-0058640 | A | | 5/2019 | |
| KR | 10-2019-0061314 | A | | 6/2019 | |
| KR | 10-2019-0140659 | A | | 12/2019 | |
| WO | 2018/069167 | A1 | | 4/2018 | |
| WO | 2020/159019 | A1 | | 8/2020 | |

OTHER PUBLICATIONS

EESR for corresponding EP Application No. 20890898.8, dated Oct. 27, 2022, 4 pages.

Extended European Search Report dated Oct. 11, 2023, 5 pages.

* cited by examiner

COMPOUND FOR ORGANIC ELECTRONIC ELEMENT, ORGANIC ELECTRONIC ELEMENT USING THE SAME, AND AN ELECTRONIC DEVICE THEREOF

BACKGROUND

Cross-Reference of Related Applications

This application is a continuation-in-part of U.S. patent application Ser. No. 17/756,193 filed on May 19, 2022, which was a 371 of PCT/KR2020/016272 filed on Nov. 18, 2020, which claims the benefit of priority from Korean Patent Application No. 10-2020-0102536 filed on Aug. 14, 2020 and Korean Patent Application No. 10-2019-0148780 filed on Nov. 19, 2019, the contents of each of which are incorporated herein by reference in its entirety.

TECHNICAL FIELD

The present invention relates to compound for organic electronic element, organic electronic element using the same, and an electronic device thereof.

BACKGROUND ART

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function.

In the organic light emitting diode, the most problematic is the lifetime and the efficiency. As the display becomes large, the efficiency and the lifetime problem must be solved.

Efficiency, life span, driving voltage and the like are related to each other, as the efficiency is increased, the driving voltage is relatively decreased, and as the driving voltage drops, the crystallization of the organic material due to joule heating generated during driving is reduced, and as a result, the life span tends to increase.

However, simply improving the organic material layer cannot maximize the efficiency. This is because, when the optimal combination of the energy level and T1 value between each organic material layer and the intrinsic properties (mobility, interface characteristics, etc.) of the material are achieved, long life and high efficiency can be achieved at the same time.

Further, recently, in organic electroluminescent devices, in order to solve the emission problem in the hole transport layer, an emitting-auxiliary layer must be present between the hole transport layer and an emitting layer, and it is necessary to develop different emitting-auxiliary layers according to the respective emitting layers (R, G, B).

In general, electrons are transferred from the electron transport layer to the emitting layer, and holes are transferred from the hole transport layer to the emitting layer to generate excitons by recombination.

However, the material used for the hole transport layer has a low HOMO value and therefore has mostly low T1 value. As a result, the exciton generated in the emitting layer is transferred to the hole transport layer, resulting in charge unbalance in the emitting layer, and light is emitted at the interface of the hole transport layer.

When light is emitted at the interface of the hole transport layer, the color purity and efficiency of the organic electronic device are lowered and the life span is shortened. Therefore, it is urgently required to develop an emitting-auxiliary layer having a high T1 value and a HOMO level between the HOMO energy level of the hole transport layer and the HOMO energy level of the emitting layer.

Meanwhile, it is necessary to develop a hole injection layer material having stable characteristics, that is, a high glass transition temperature, against joule heating generated when the device is driven, while delaying penetration of the metal oxide from the anode electrode (ITO), which is one of the causes of shortening the lifetime of the organic electronic device, into the organic layer. The low glass transition temperature of the hole transport layer material has a characteristic that when the device is driven, the uniformity of the surface of the thin film is lowered, which has been reported to have a great influence on the lifetime of the device. In addition, OLED devices are mainly formed by a deposition method, and it is necessary to develop a material that can withstand long time in deposition, that is, a material having high heat resistance characteristics.

That is, in order to sufficiently exhibit the excellent characteristics of the organic electronic element, a material for forming an organic material layer in an element such as a hole injection material, a hole transport material, a light emitting material, an electron transport material, an electron injection material, an emitting-auxiliary layer material should be supported by stable and efficient materials. However, such a stable and efficient organic material layer material for an organic electronic element has not been sufficiently developed yet. Therefore, development of new materials is continuously required, and development of materials for the hole transport layer or the emitting-auxiliary layer is urgently required.

DETAILED DESCRIPTION OF THE INVENTION

Summary

In order to solve the problems of the background art described above, the present invention has revealed a compound having a novel structure, and that when the compound is applied to an organic electronic element, the luminous efficiency, stability and lifetime of the element are greatly improved.

Accordingly, it is an object of the present invention to provide a novel compound, an organic electronic element using the same, and an electronic device.

Technical Solution

The present invention provides a compound represented by Formula A.

<Formula A>

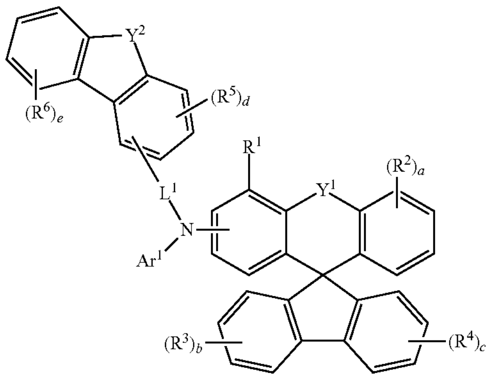

In another aspect, the present invention provides an organic electronic element comprising the compound represented by Formula A and an electronic device thereof.

Effects of the Invention

By using the compound according to the present invention, it is possible to achieve a high luminous efficiency, a low driving voltage, and a high heat resistance of the element, and can greatly improve the color purity and lifespan of the element.

Figure 1:
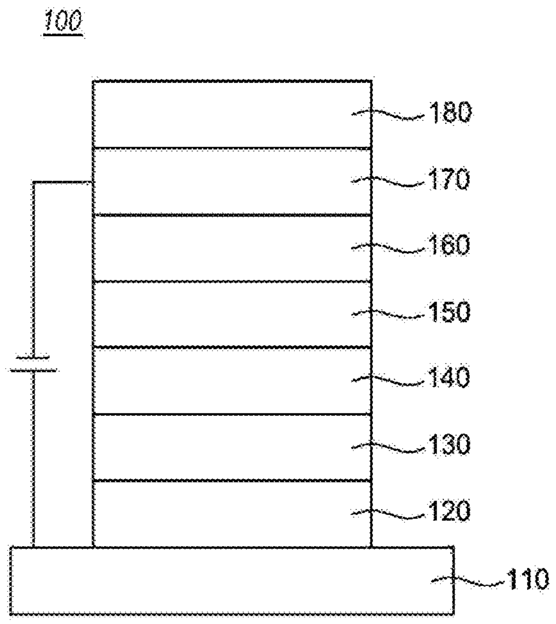
FIG. 1 to FIG. 3 illustrate an example of an organic electronic element according to the present invention.

| | |
|---|---|
| 100, 200, 300: | organic electronic element |
| 110: | the first electrode |
| 120: | hole injection layer |
| 130: | hole transport layer |
| 140: | emitting layer |
| 150: | electron transport layer |
| 160: | electron injection layer |
| 170: | second electrode |
| 180: | light efficiency enhancing Layer |
| 210: | buffer layer |
| 220: | emitting-auxiliary layer |
| 320: | first hole injection layer |
| 330: | first hole transport layer |
| 340: | first emitting layer |
| 350: | first electron transport layer |
| 360: | first charge generation layer |
| 361: | second charge generation layer |
| 420: | second hole injection layer |
| 430: | second hole transport layer |
| 440: | second emitting layer |
| 450: | second electron transport layer |
| CGL: | charge generation layer |
| ST1: | first stack |
| ST2: | second stack |

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being “connected”, “coupled”, or “connected” to another component, the component may be directly connected or connected to the other component, but another component may be “connected”, “coupled” or “connected” between each component.

As used in the specification and the accompanying claims, unless otherwise stated, the following is the meaning of the term as follows.

Unless otherwise stated, the term “halo” or “halogen”, as used herein, includes fluorine, bromine, chlorine, or iodine.

Unless otherwise stated, the term “alkyl” or “alkyl group”, as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term “alkenyl” or “alkynyl”, as used herein, has double or triple bonds of 2 to 60 carbon atoms, but is not limited thereto, and includes a linear or a branched chain group.

Unless otherwise stated, the term “cycloalkyl”, as used herein, means alkyl forming a ring having 3 to 60 carbon atoms, but is not limited thereto.

Unless otherwise stated, the term “alkoxyl group”, “alkoxy group” or “alkyloxy group”, as used herein, means an oxygen radical attached to an alkyl group, but is not limited thereto, and has 1 to 60 carbon atoms.

Unless otherwise stated, the term “aryloxy group” or “aryloxy group”, as used herein, means an oxygen radical attached to an aryl group, but is not limited thereto, and has 6 to 60 carbon atoms.

Unless otherwise stated, the term “aryl group” or “arylene group”, as used herein, has 6 to 60 carbon atoms, but is not limited thereto. Herein, the aryl group or arylene group means a monocyclic and polycyclic aromatic group, and may also be formed in conjunction with an adjacent group. Examples of “aryl group” may include a phenyl group, a biphenyl group, a fluorene group, or a spirofluorene group.

The prefix “aryl” or “ar” means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphatic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes compound below.

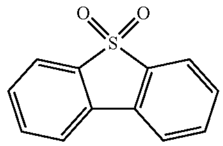 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

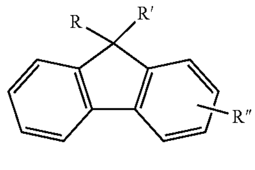

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro-' and 'tri-spiro-', respectively, depending on the number of atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiophen group, a $C_6$-$C_{20}$ arylthiophen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

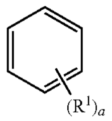

wherein, when a is an integer of zero, the substituent $R^1$ is absent, when a is an integer of 1, the sole substituent $R^1$ is linked to any one of the carbon constituting the benzene ring, when a is an integer of 2 or 3, each substituent $R^1$s may be the same and different, when a is an integer of 4 to 6, and is linked to the benzene ring in a similar manner, whereas the indication of hydrogen bound to the carbon forming the benzene ring is omitted.

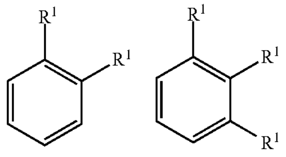

(a = 2) (a = 3)

Hereinafter, a compound according to an aspect of the present invention and an organic electronic element comprising the same will be described.

The present invention provides a compound represented by Formula A.

<Formula A>

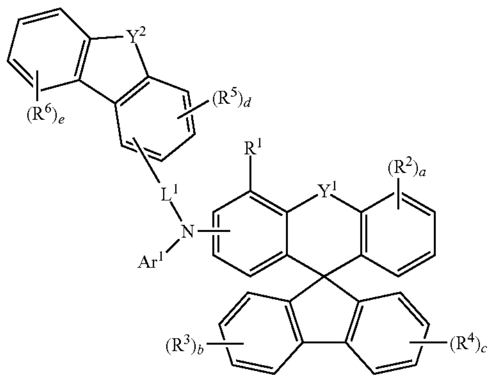

wherein, each symbol may be defined as follows.

1) $Y^1$ and $Y^2$ are each independently O or S;

2) $L^1$ is selected from the group consisting of single bond; a $C_6$-$C_{60}$ arylene group; a fluorenylene group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

wherein in case $L^1$ is an arylene group, it is preferably an $C_6$~$C_{30}$ arylene group, more preferably an $C_6$-$C_{25}$ arylene group, such as phenylene, biphenylene, naphthylene, terphenylene, etc.

wherein in case $L^1$ is a fluorenylene group, it may be 9,9-dimethyl-9H-fluorenylene, 9,9-diphenyl-9H-fluorenylene, 9,9'-spirobifluorenylene.

when $L^1$ is a heterocyclic group, it is preferably a $C_2$-$C_{30}$ heterocyclic group, and more preferably a $C_2$-$C_{24}$ heterocyclic group, for example, pyridine, pyrimidine, quinoline, quinazoline, quinoxaline, dibenzofuran, dibenzothiophene, naphthobenzothiophene, naphthobenzofuran, benzofuran, benzothiophene, etc.

when $L^1$ is a fused ring group, it is preferably a fused ring group of an $C_3$-$C_{30}$ aliphatic ring and an $C_6$~$C_{30}$ aromatic ring, and more preferably a fused ring group of an $C_3$-$C_{24}$ aliphatic ring and an $C_6$-$C_{24}$ aromatic ring, 3) $Ar^1$ is selected from the group consisting of $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

wherein in case $Ar^1$ is an aryl group, it is preferably an $C_6$-$C_{30}$ aryl group, more preferably an $C_6$-$C_{25}$ aryl group, such as phenyl, biphenyl, terphenyl, naphthalene, etc.

when $Ar^1$ is a heterocyclic group, it is preferably a $C_2$-$C_{30}$ heterocyclic group, and more preferably a $C_2$~$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, Phenylphenothiazine, etc.

when $Ar^1$ is a fused ring group, it is preferably a fused ring group of an $C_3$-$C_{30}$ aliphatic ring and an $C_6$~$C_{30}$ aromatic ring, and more preferably a fused ring group of an $C_3$-$C_{24}$ aliphatic ring and an $C_6$-$C_{24}$ aromatic ring, 4) $R^1$ is selected from the group consisting of a $C_6$-$C_{60}$ aryl group; a fluorenyl group; a $C_3$-$C_{60}$ aliphatic cyclic group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

wherein in case $R^1$ is an aryl group, it is preferably an $C_6$~$C_{30}$ aryl group, more preferably an $C_6$~$C_{25}$ aryl group, such as phenyl, biphenyl, terphenyl, naphthalene, etc.

when $R^1$ is a heterocyclic group, it is preferably a $C_2$~$C_{30}$ heterocyclic group, and more preferably a $C_2$~$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

When $R^1$ is an aliphatic cyclic group, it may be preferably a $C_3$~$C_{30}$ aliphatic group, more preferably a $C_3$~$C_{24}$ aliphatic group.

when $R^1$ is a fused ring group, it is preferably a fused ring group of an $C_3$~$C_{30}$ aliphatic ring and an $C_6$~$C_{30}$ aromatic ring, and more preferably a fused ring group of an $C_3$~$C_{24}$ aliphatic ring and an $C_6$~$C_{24}$ aromatic ring, 5) $R^2$, $R^3$, $R^4$, $R^5$ and $R^6$ are each independently selected from the group consisting of hydrogen; deuterium; tritium; halogen; cyano group; nitro group; $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; $C_1$-$C_{50}$ alkyl group; $C_2$-$C_{20}$ alkenyl group; $C_2$-$C_{20}$ alkynyl group; $C_1$-$C_{30}$ alkoxyl group; $C_6$-$C_{30}$ aryloxy group; and -L'-N($R^a$)($R^b$); wherein in case $R^2$, $R^3$, $R^4$, $R^5$ and $R^6$ are an aryl group, it is preferably an $C_6$~$C_{30}$ aryl group, more preferably an $C_6$~$C_{25}$ aryl group, such as phenyl, biphenyl, terphenyl, naphthalene, etc. wherein in case $R^2$, $R^3$, $R^4$, $R^5$ and $R^6$ are a heterocyclic group, it is preferably a $C_2$~$C_{30}$ heterocyclic group; and more preferably a $C_2$~$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

wherein in case $R^2$, $R^3$, $R^4$, $R^5$ and $R^6$ are a fused ring group, it is preferably a fused ring group of an $C_3$~$C_{30}$ aliphatic ring and an $C_6$~$C_{30}$ aromatic ring, more preferably a fused ring group of an $C_3$~$C_{24}$ aliphatic ring and an $C_6$~$C_{24}$ aromatic ring.

wherein in case $R^2$, $R^3$, $R^4$, $R^5$ and $R^6$ are an alkyl group, it is preferably an $C_1$~$C_{30}$ alkyl group, more preferably an $C_1$~$C_{24}$ alkyl group, wherein in case $R^2$, $R^3$, $R^4$, $R^5$ and $R^6$ are an alkoxyl group, it is preferably an $C_1$~$C_{24}$ alkoxyl group, wherein in case $R^2$, $R^3$, $R^4$, $R^5$ and $R^6$ are an aryloxy group, it is preferably an $C_6$~$C_{24}$ aryloxy group, 6) a, b, c and e are each independently an integer from 0 to 4, d is an integer from 0 to 3, wherein in case a, b, c and d are 2 or more, $R^2$, $R^3$, $R^4$, $R^5$ and $R^6$ are each in plural being the same or different, and an adjacent plurality of $R^2$ or a plurality of $R^3$ or a plurality of $R^4$ or a plurality of $R^5$ or a plurality of $R^6$ may be bonded to each other to form a ring, 7) L' is selected from the group consisting of single bond; a $C_6$-$C_{60}$ arylene group; a fluorenylene group; a $C_3$-$C_{60}$ aliphatic ring; a $C_2$-$C_{60}$ heterocyclic group including at least one heteroatom of O, N, S, Si or P; and combinations thereof, wherein $R^a$ and $R^b$ are each independently selected from the group consisting of a $C_6$-$C_{60}$ aryl group; a fluorenyl group; a $C_3$-$C_{60}$ aliphatic ring; a $C_2$-$C_{60}$ heterocyclic group including at least one heteroatom of O, N, S, Si or P; and combinations thereof, wherein in case L' is an arylene group, it is preferably an $C_6$~$C_{30}$ arylene group, more preferably an $C_6$~$C_{25}$ arylene group, such as phenylene, biphenylene, naphthylene, terphenylene, etc.

wherein in case L' is a fluorenylene group, it may be 9,9-dimethyl-9H-fluorenylene, 9,9-diphenyl-9H-fluorenylene, 9,9'-spirobifluorenylene.

wherein in case L' is an aliphatic ring, it may be preferably a $C_3$-$C_{30}$ aliphatic ring group, more preferably a $C_3$-$C_{24}$ aliphatic ring group.

In case L' is a heterocyclic group, it is preferably a $C_2$~$C_{30}$ heterocyclic group, and more preferably a $C_2$~$C_{24}$ heterocyclic group, for example, pyridine, pyrimidine, quinoline, quinazoline, quinoxaline, dibenzofuran, dibenzothiophene, naphthobenzothiophene, naphthobenzofuran, benzofuran, benzothiophene, etc.

wherein in case $R^a$ and $R^b$ are an aryl group, it is preferably an $C_6$-$C_{30}$ aryl group, more preferably an $C_6$-$C_{25}$ aryl group, such as phenyl, biphenyl, terphenyl, naphthalene, etc.

wherein in case $R^a$ and $R^b$ are a heterocyclic group, it is preferably a $C_2$-$C_{30}$ heterocyclic group; and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

wherein in case $R^a$ and $R^b$ are an aliphatic ring, it may be preferably a $C_3$-$C_{30}$ aliphatic ring group, more preferably a $C_3$-$C_{24}$ aliphatic ring group.

wherein, the aryl group, arylene group, heterocyclic group, fluorenyl group, fluorenylene group, fused ring group, alkyl group, alkenyl group, alkoxy group, aryloxy group and aliphatic cyclic group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; $C_5$-$C_{20}$ arylalkenyl group; and -L'-N($R_a$)($R_b$); wherein the substituents may be bonded to each other to form a saturated or unsaturated ring, wherein the term 'ring' means a $C_3$-$C_{60}$ aliphatic ring, a $C_6$-$C_{60}$ aromatic ring, or a $C_2$-$C_{60}$ heterocyclic group, or a fused ring formed by combination thereof.

Also, Formula A is represented by any one of Formulas A-1 to A-3.

<Formula A-1>

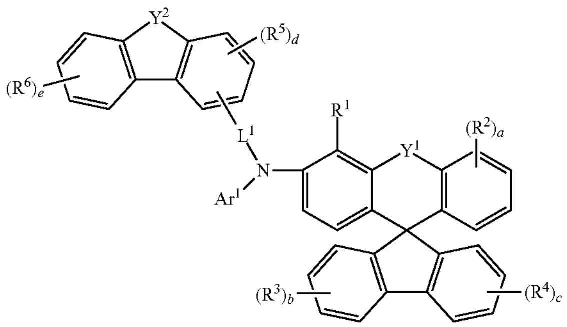

<Formula A-2>

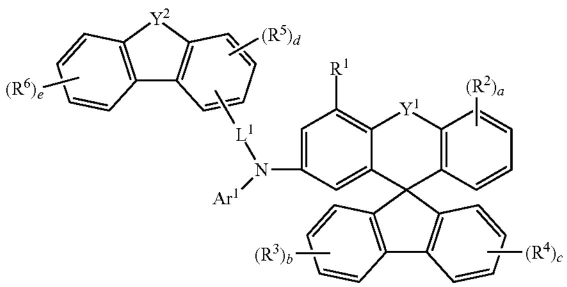

<Formula A-3>

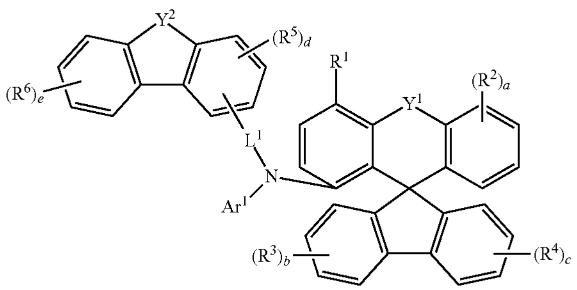

Wherein, $Y^1$, $Y^2$, $L^1$, $Ar^1$, $R^1$, $R^2$, $R^3$, $R^4$, $R^5$, $R^6$, a, b, c, d and e are the same as defined in Formula A.

Also, Formula A is represented by any one of Formulas A-4 to A-7.

<Formula A-4>

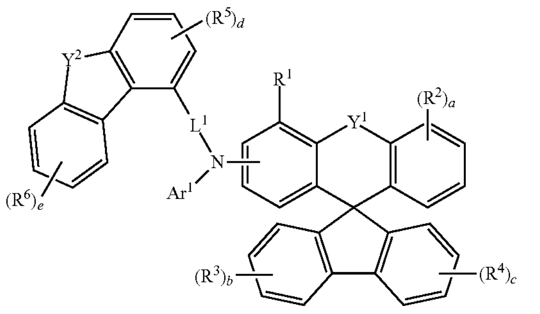

<Formula A-5>

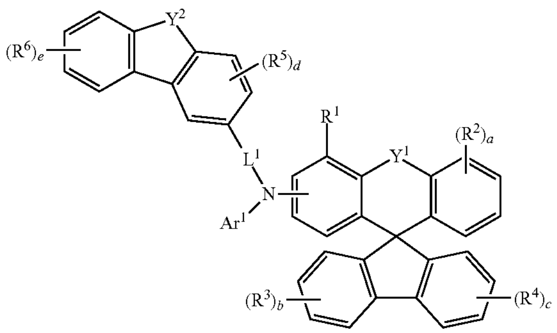

<Formula A-6>

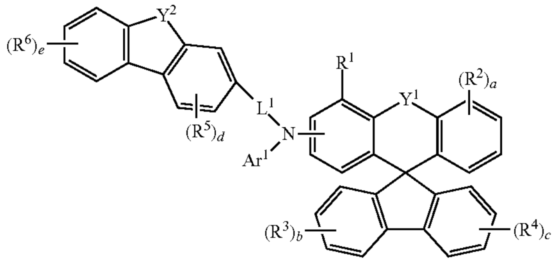

<Formula A-7>

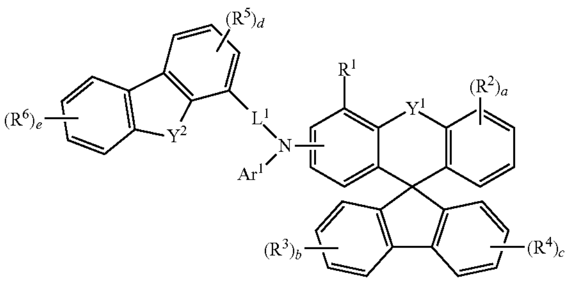

Wherein, $Y^1$, $Y^2$, $L^1$, $Ar^1$, $R^1$, $R^2$, $R^3$, $R^4$, $R^5$, $R^6$, a, b, c, d and e are the same as defined in Formula A.

Also, Formula A is represented by Formula A-8.

<Formula A-8>

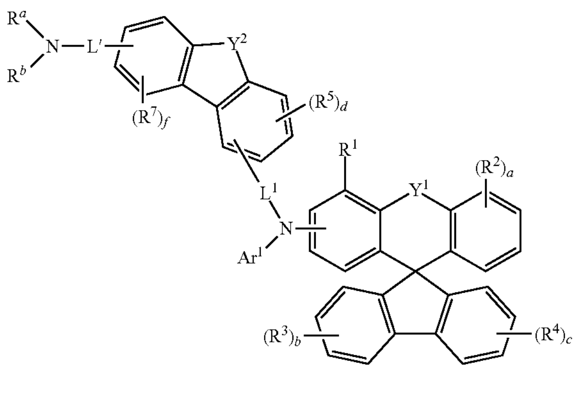

Wherein, $Y^1$, $Y^2$, $L^1$, $Ar^1$, $R^1$, $R^2$, $R^3$, $R^4$, $R^5$, a, b, c, d, L', $R^a$ and $R^b$ are the same as defined in Formula A. $R^7$ is the same as the definition of $R^2$, f is an integer from 0 to 3.

Also, $Ar^1$ is represented by any one of Formulas Ar-1 to Ar-6.

<Formula Ar-1>

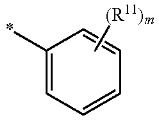

<Formula Ar-2>

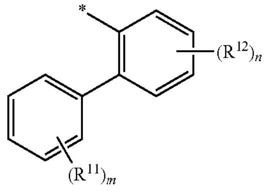

<Formula Ar-3>

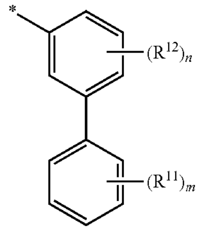

<Formula Ar-4>

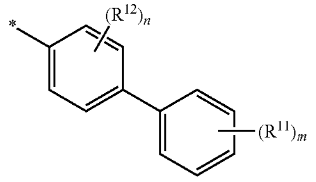

<Formula Ar-5>

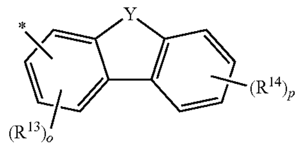

-continued

<Formula Ar-6>

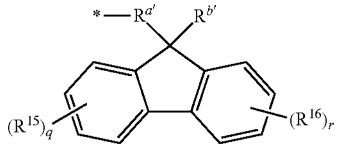

Wherein, each symbol may be defined as follows.

*- indicates the bonding position $R^{11}$, $R^{12}$, $R^{13}$, $R^{14}$, $R^{15}$ and $R^{16}$ are the same or different from each other and are each independently selected from the group consisting of hydrogen; deuterium; halogen; cyano group; nitro group; $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; $C_1$-$C_{50}$ alkyl group; $C_2$-$C_{20}$ alkenyl group; $C_2$-$C_{20}$ alkynyl group; $C_1$-$C_{30}$ alkoxyl group; $C_6$-$C_{30}$ aryloxy group;

wherein in case $R^{11}$, $R^{12}$, $R^{13}$, $R^{14}$, $R^{15}$ and $R^{16}$ are an aryl group, it is preferably an $C_6$~$C_{30}$ aryl group, more preferably an $C_6$~$C_{25}$ aryl group, such as phenyl, biphenyl, terphenyl, naphthalene, etc.

wherein in case $R^{11}$, $R^{12}$, $R^{13}$, $R^{14}$, $R^{15}$ and $R^{16}$ are a heterocyclic group, it is preferably a $C_2$-$C_{30}$ heterocyclic group; and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

wherein $R^{11}$, $R^{12}$, $R^{13}$, $R^{14}$, $R^{15}$ and $R^{16}$ are a fused ring group, it is preferably a fused ring group of an $C_3$~$C_{30}$ aliphatic ring and an $C_6$-$C_{30}$ aromatic ring, more preferably a fused ring group of an $C_3$~$C_{24}$ aliphatic ring and an $C_6$-$C_{24}$ aromatic ring.

wherein in case $R^{11}$, $R^{12}$, $R^{13}$, $R^{14}$, $R^{15}$ and $R^{16}$ are an alkyl group, it is preferably an $C_1$~$C_{30}$ alkyl group, more preferably an $C_1$-$C_{24}$ alkyl group, wherein in case $R^1$, $R^{12}$, $R^{13}$, $R^{14}$, $R^{15}$ and $R^{16}$ are an alkoxyl group, it is preferably an $C_1$~$C_{24}$ alkoxyl group, wherein in case $R^{11}$, $R^{12}$, $R^{13}$, $R^{14}$, $R^{15}$ and $R^{16}$ are an aryloxy group, it is preferably an $C_6$-$C_{24}$ aryloxy group, Y is O, S, $CR^xR^y$ or $NR^z$, $R^{a'}$, $R^{b'}$, $R^x$, $R^y$ and $R^z$ are each independently selected from the group consisting of a $C_6$-$C_{60}$ aryl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; $C_1$-$C_{50}$ alkyl group; $C_2$-$C_{20}$ alkenyl group; $C_2$-$C_{20}$ alkynyl group; $C_1$-$C_{30}$ alkoxyl group; and $C_6$-$C_{30}$ aryloxy group; or $R^{a'}$ and $R^{b'}$ may be bonded to each other to form a ring, or $R^x$ and $R^y$ may be bonded to each other to form a ring, wherein in case $R^{a'}$, $R^{b'}$, $R^x$, $R^y$ and $R^z$ are an aryl group, it is preferably an $C_6$-$C_{30}$ aryl group, more preferably an $C_6$-$C_{25}$ aryl group, such as phenyl, biphenyl, terphenyl, naphthalene, etc.

wherein in case $R^{a'}$, $R^{b'}$, $R^x$, $R^y$ and $R^Z$ are a heterocyclic group, it is preferably a $C_2$-$C_{30}$ heterocyclic group; and more preferably a $C_2$~$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc.

wherein $R^{a\prime}$, $R^{b\prime}$, $R^x$, $R^y$ and $R^Z$ are a fused ring group, it is preferably a fused ring group of an $C_3$-$C_{30}$ aliphatic ring and an $C_6$~$C_{30}$ aromatic ring, more preferably a fused ring group of an $C_3$~$C_{24}$ aliphatic ring and an $C_6$-$C_{24}$ aromatic ring.

wherein in case $R^{a\prime}$, $R^{b\prime}$, $R^x$, $R^y$ and $R^Z$ are an alkyl group, it is preferably an $C_1$~$C_{30}$ alkyl group, more preferably an $C_1$-$C_{24}$ alkyl group, wherein in case $R^{a\prime}$, $R^{b\prime}$, $R^x$, $R^y$ and $R^z$ are an alkoxyl group, it is preferably an $C_1$-$C_{24}$ alkoxyl group, wherein in case $R^{a\prime}$, $R^{b\prime}$, $R^x$, $R^y$ and $R^z$ are an aryloxy group, it is preferably an $C_6$-$C_{24}$ aryloxy group, m is an integer from 0 to 5, n, p, q and r are each independently an integer from 0 to 4, and o is an integer from 0 to 3.

Specifically, the compound represented by Formula A may be any one of the following compounds A-1 to A-112, but is not limited thereto.

A-1

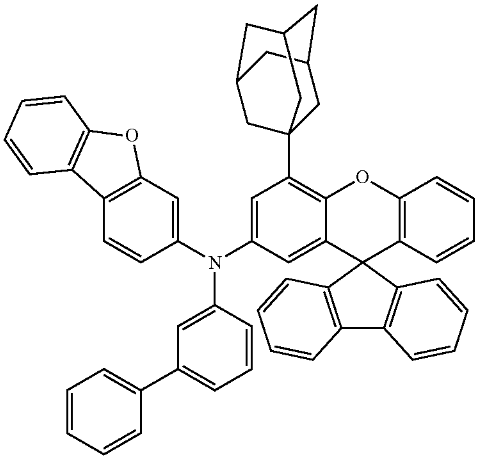

A-2

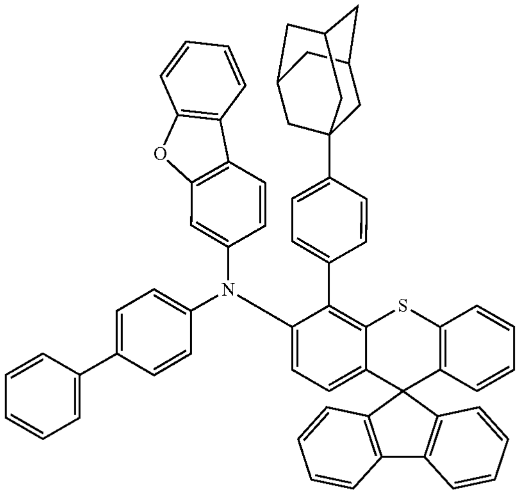

-continued

A-3

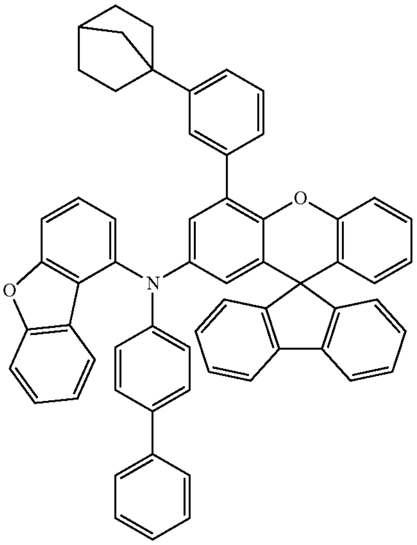

A-4

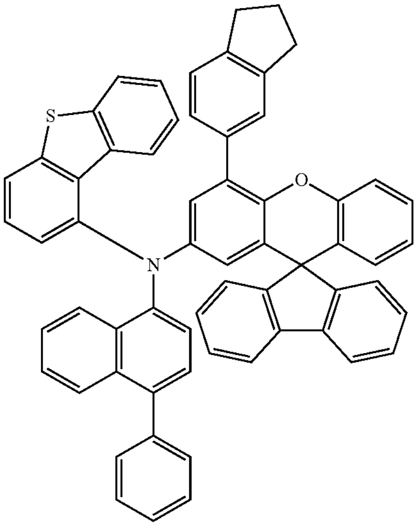

A-5

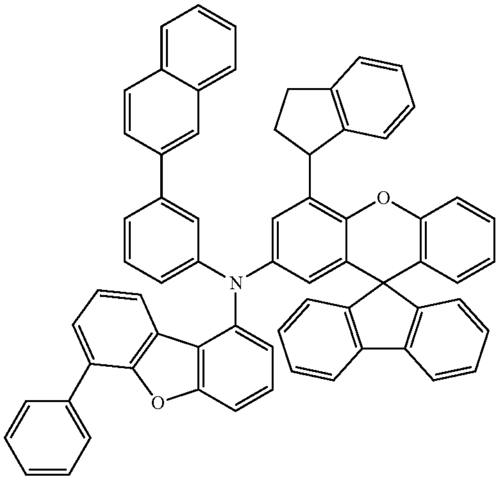

A-6
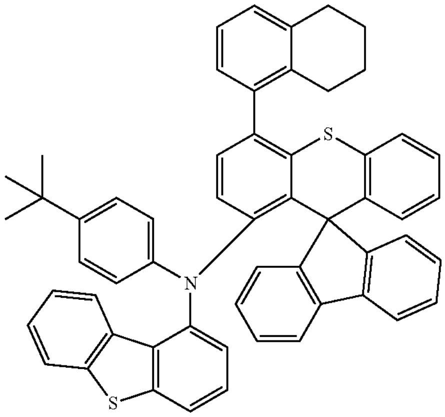
A-7
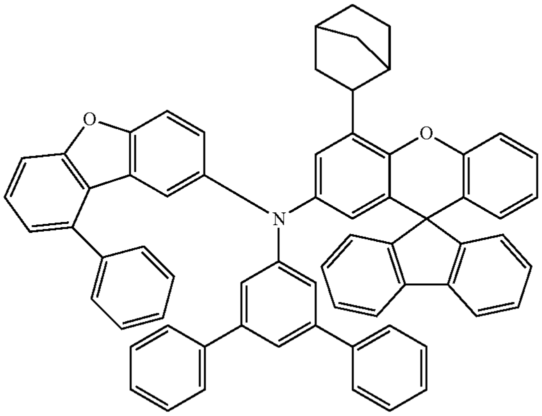
A-8
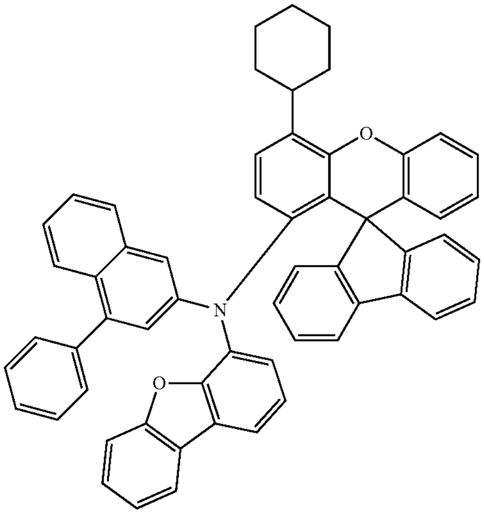
A-9
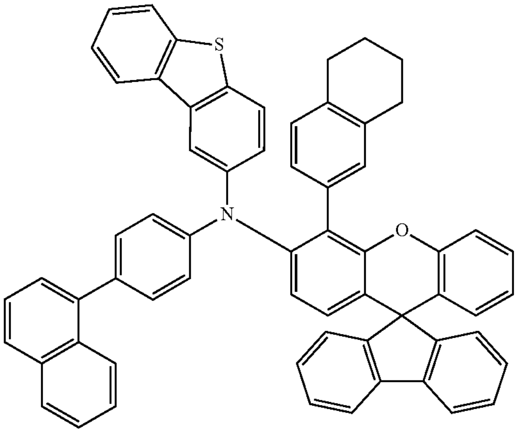
A-10
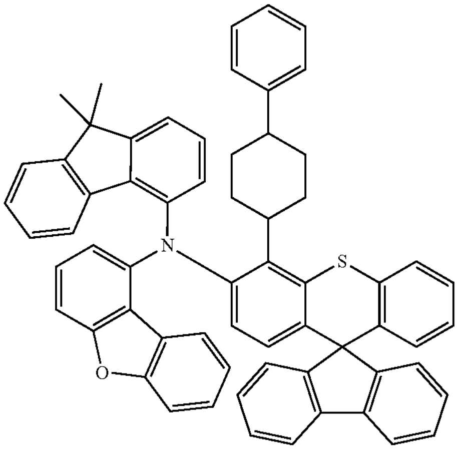
A-11
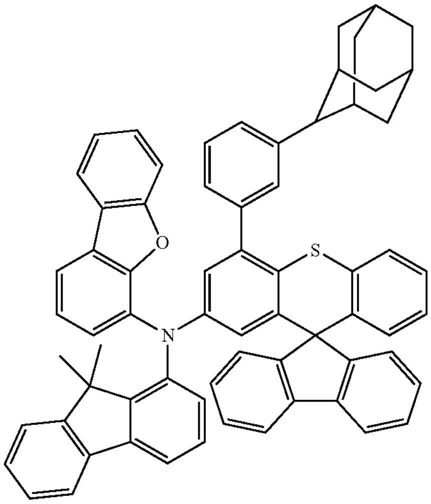

-continued
A-12
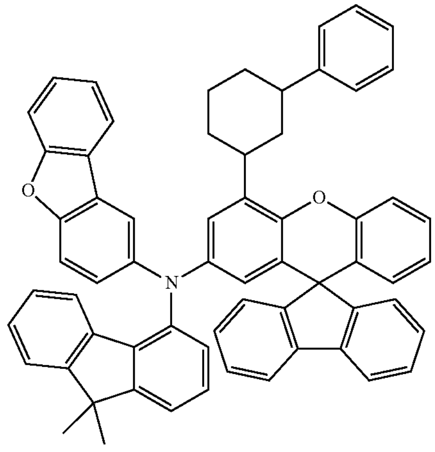
A-13
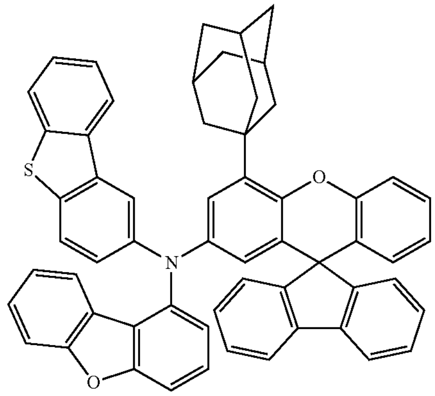
A-14
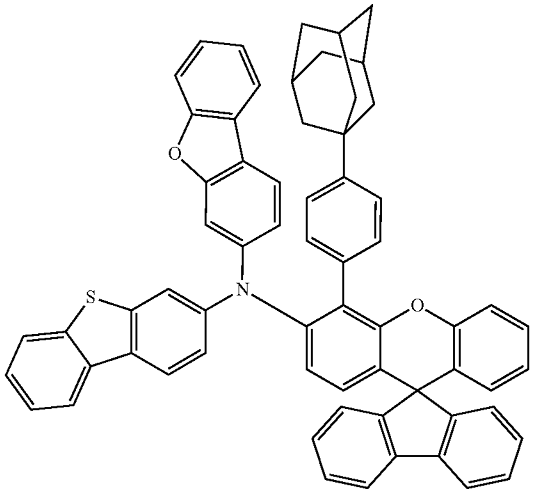
-continued
A-15
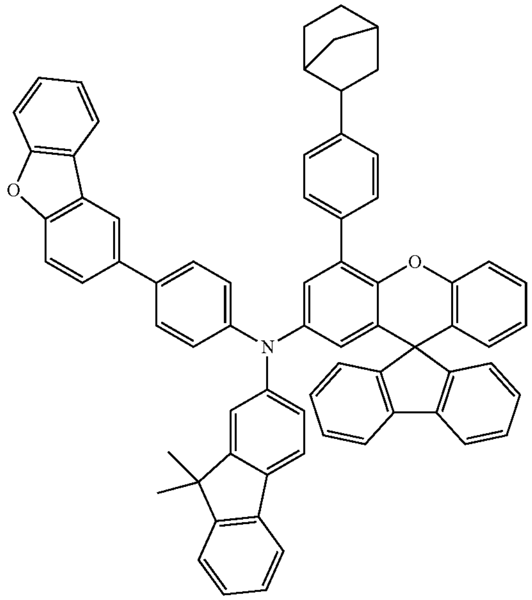
A-16
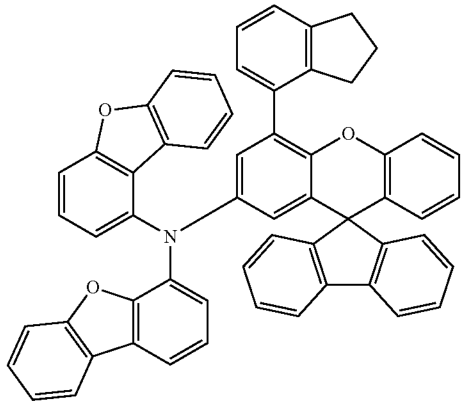
A-17
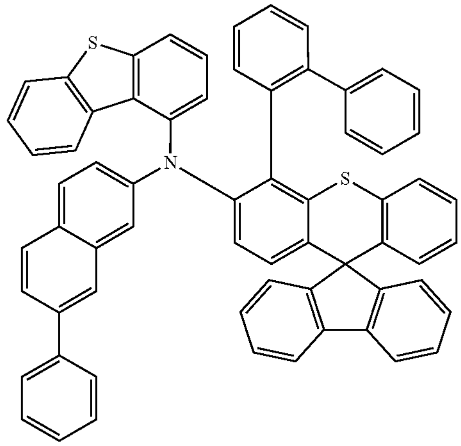

-continued
A-18
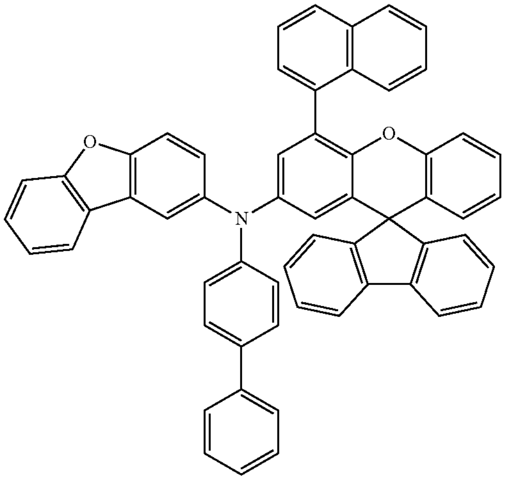
A-19
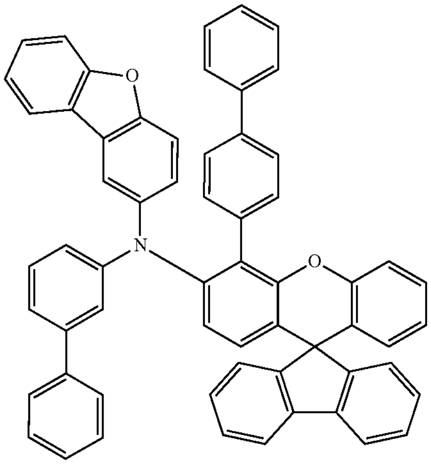
A-20
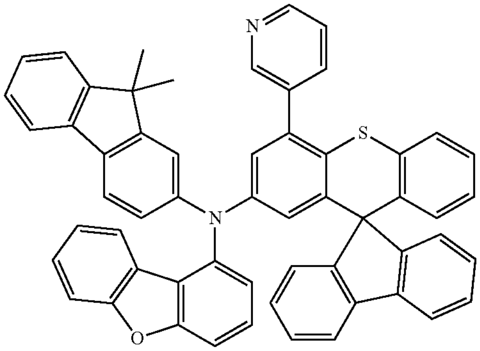
-continued
A-21
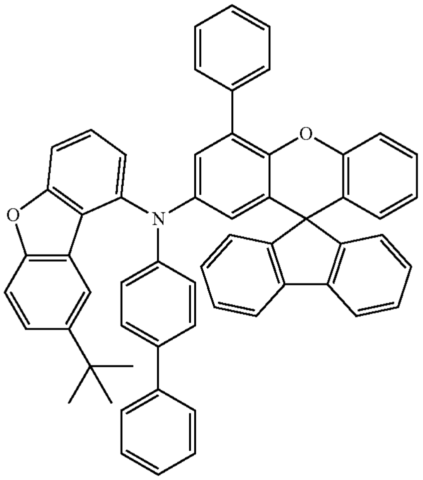
A-22
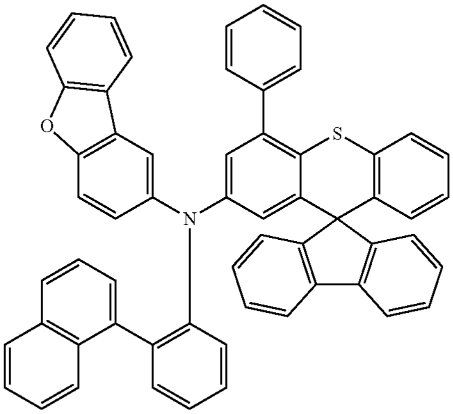
A-23
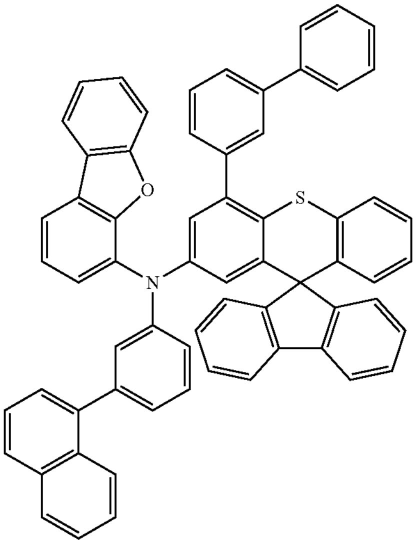

-continued
A-24
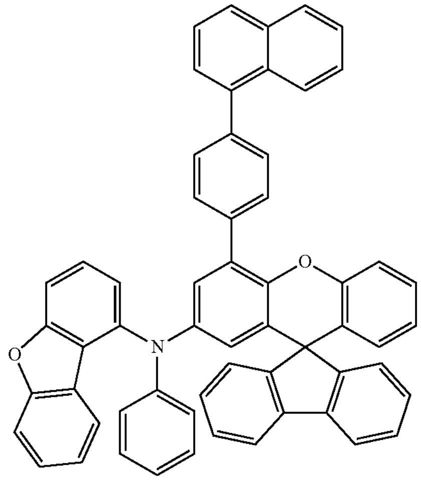
A-25
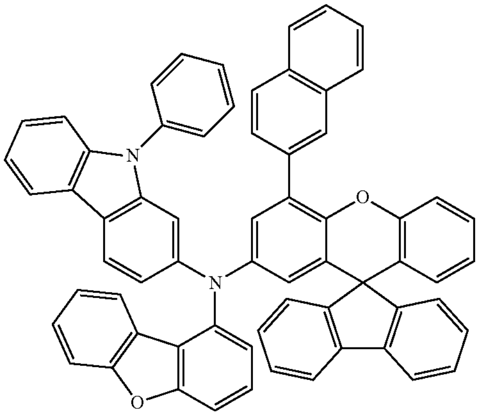
A-26
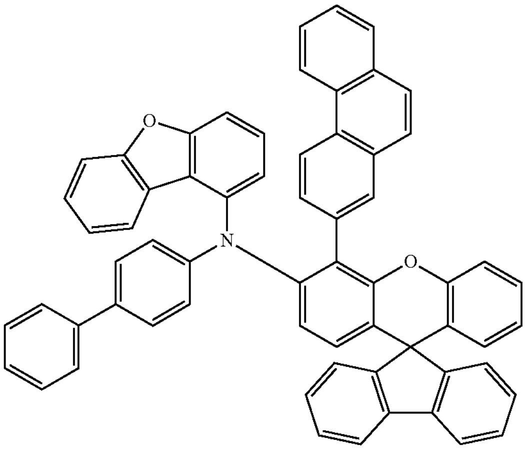
-continued
A-27
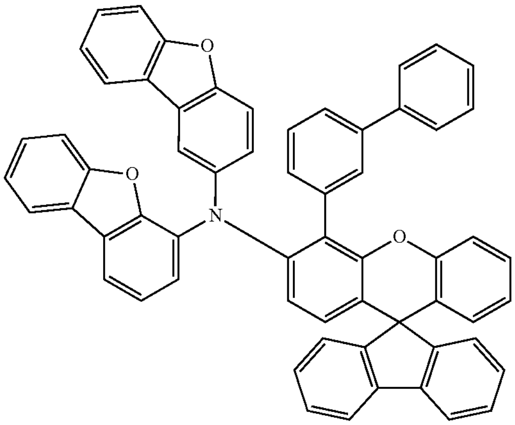
A-28
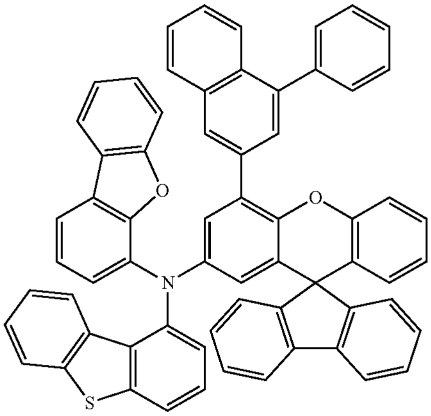
A-29
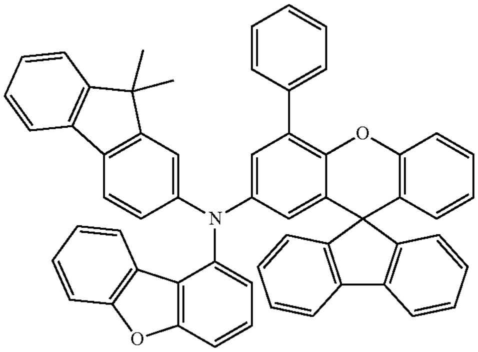
A-30
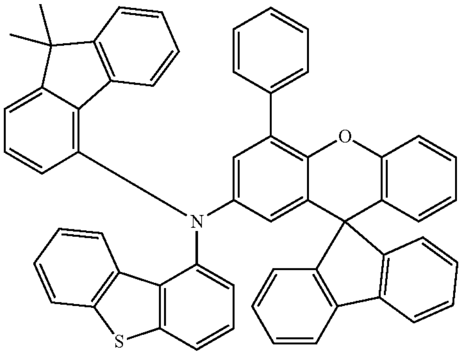

-continued
A-31
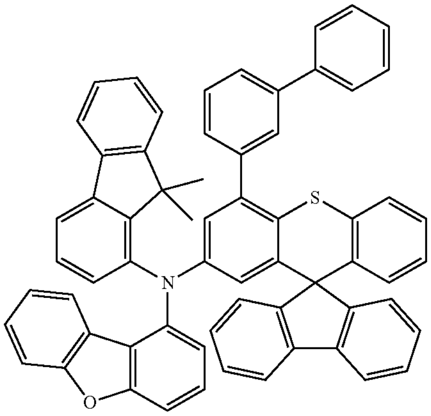
A-32
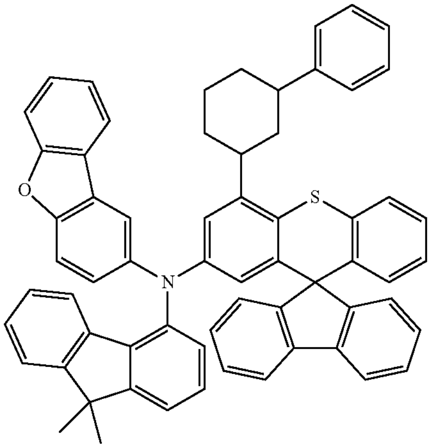
A-33
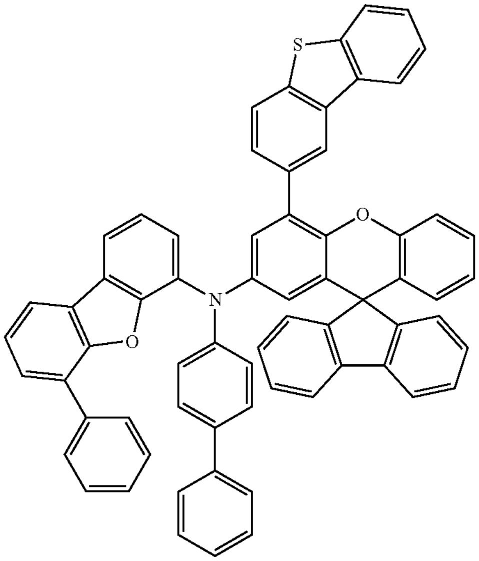
-continued
A-34
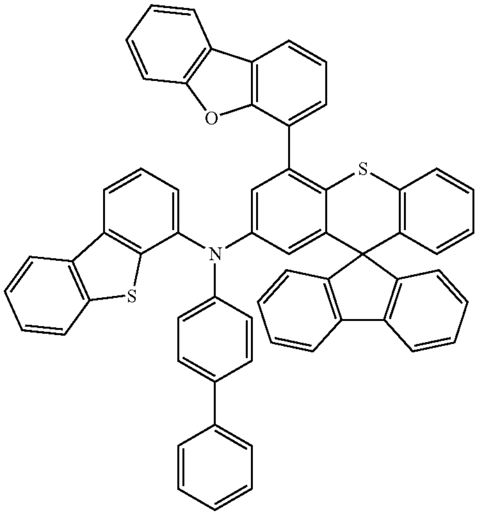
A-35
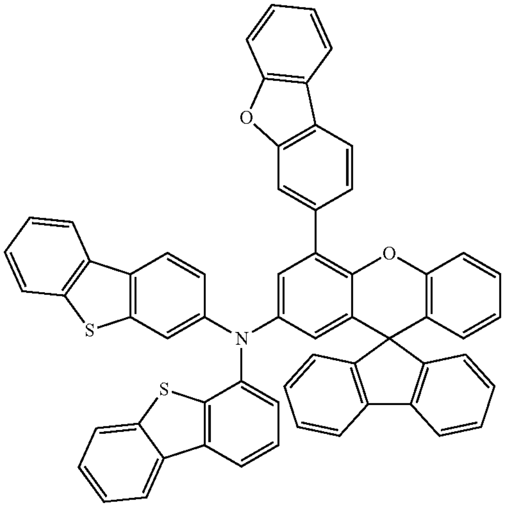
A-36
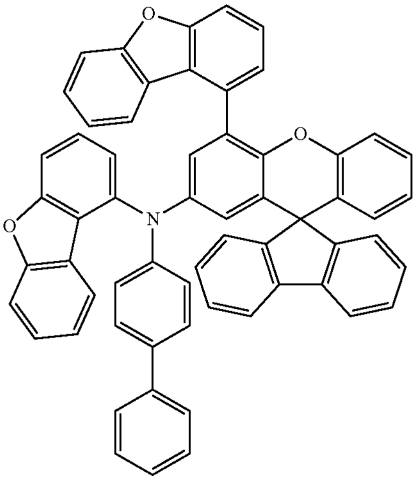

-continued
A-37
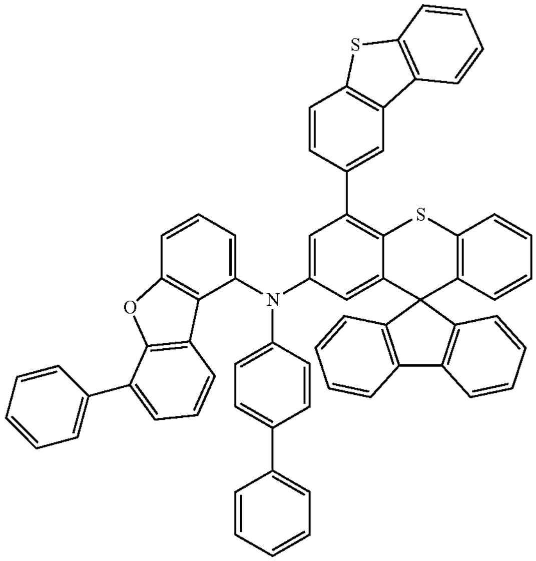
A-38
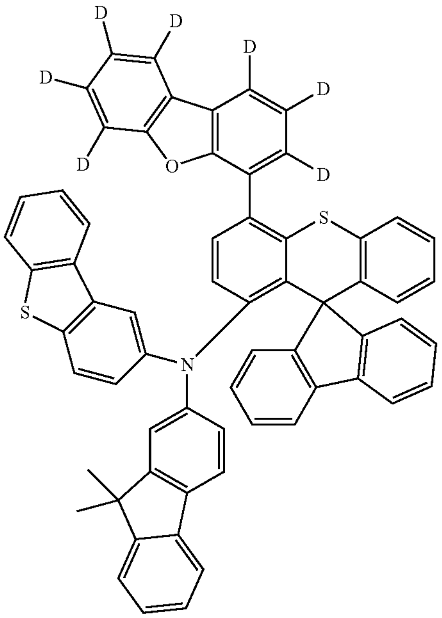
-continued
A-39
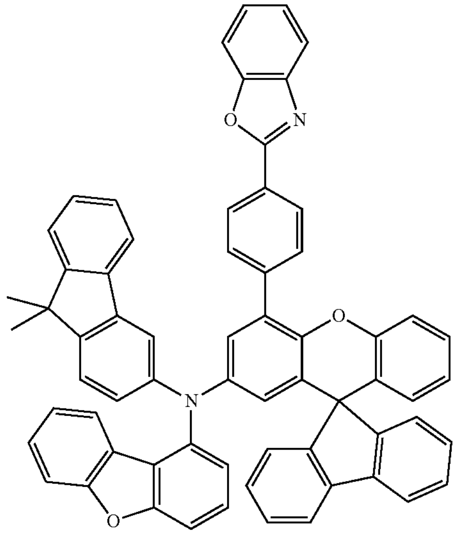
A-40
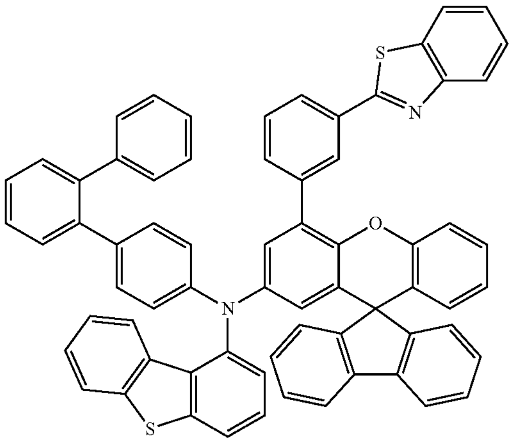
A-41
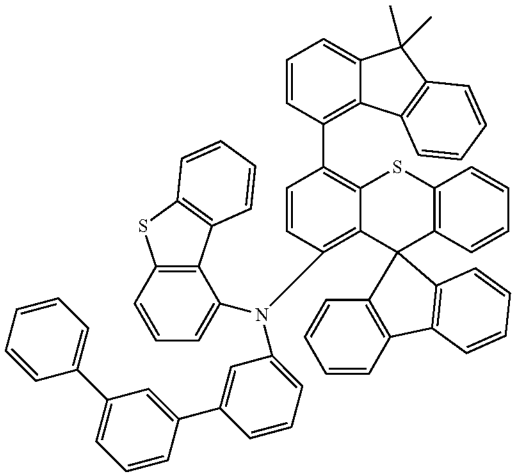

-continued
A-42
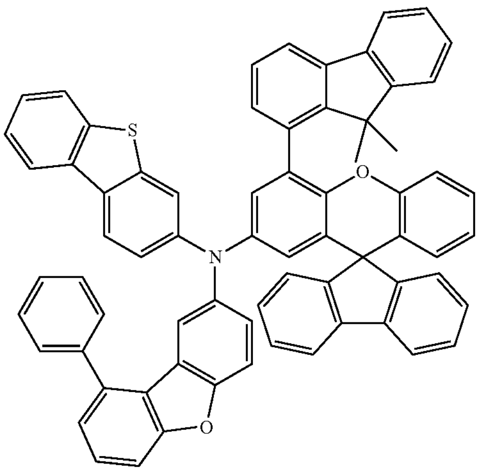
A-43
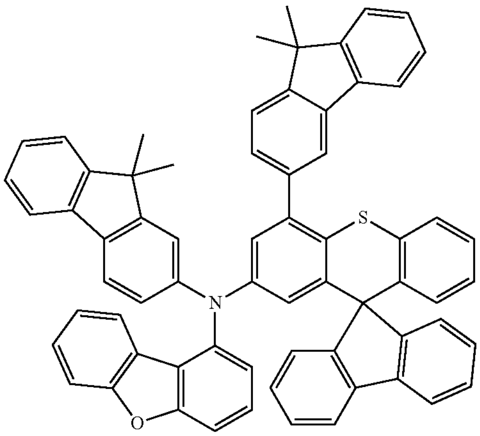
A-44
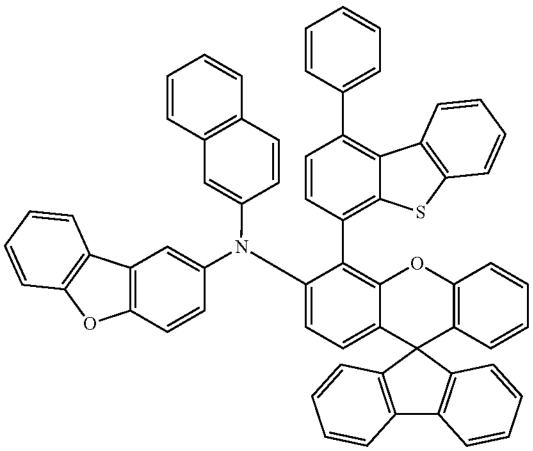
-continued
A-45
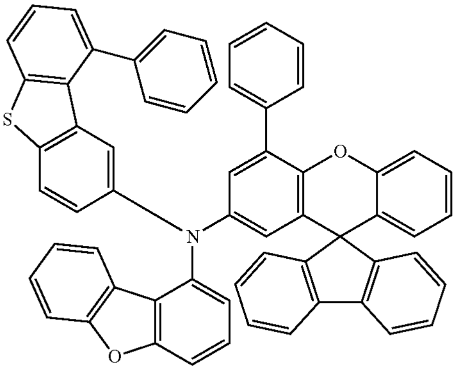
A-46
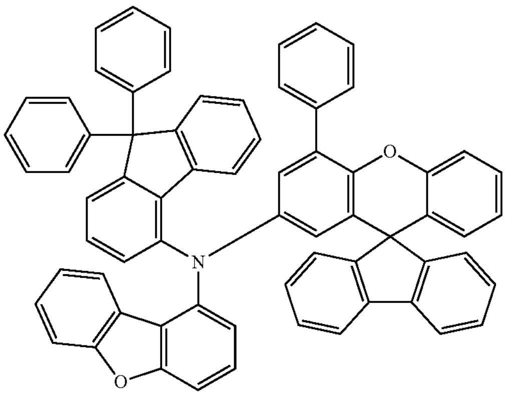
A-47
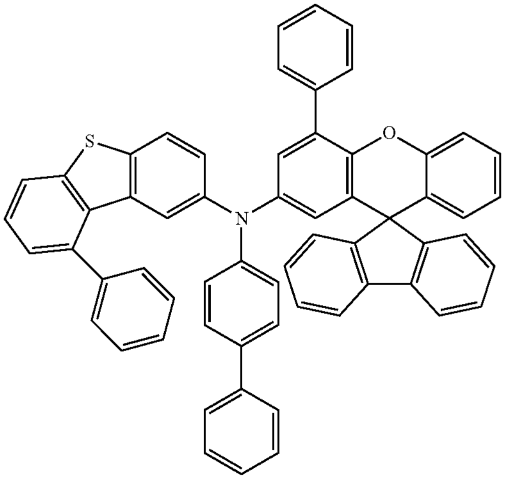

-continued
A-48
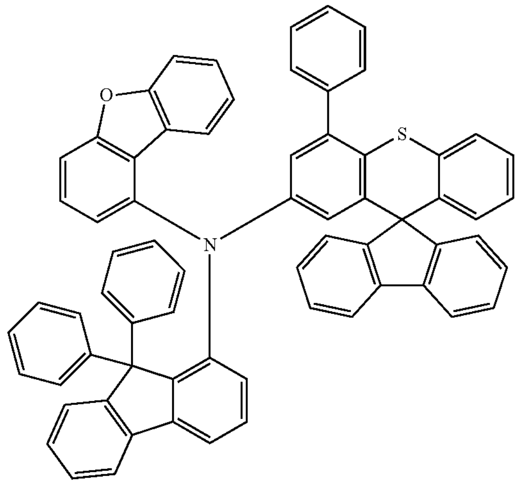
A-49
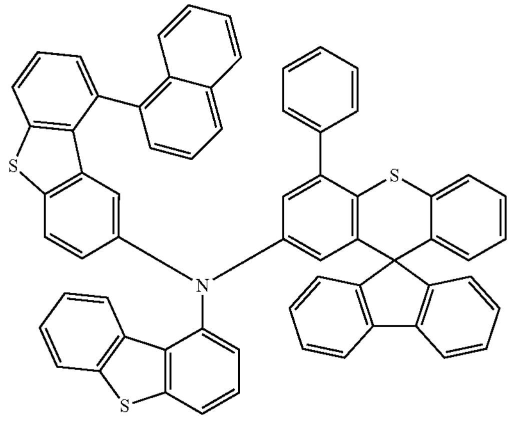
A-50
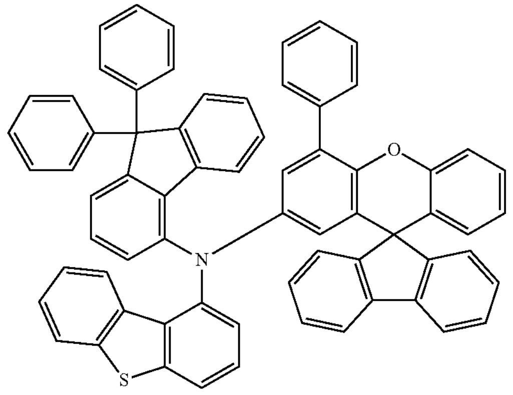
-continued
A-51
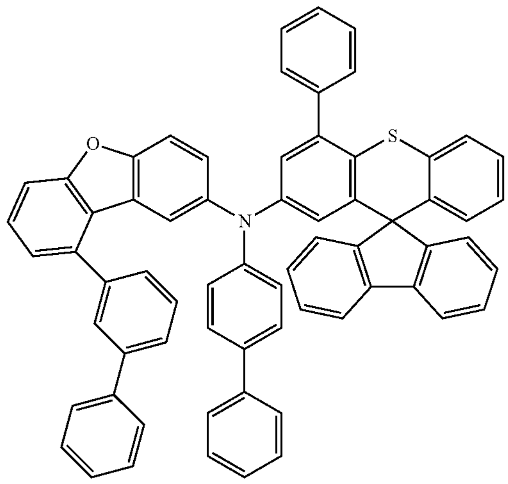
A-52
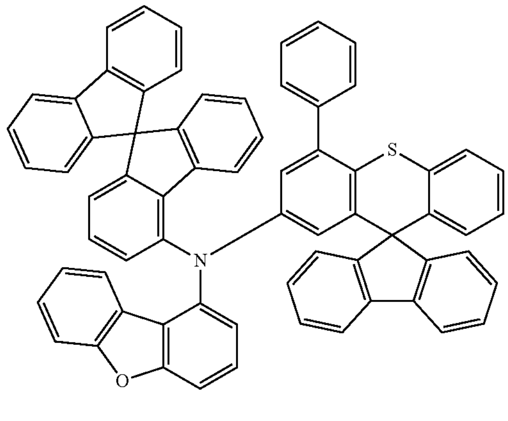
A-53
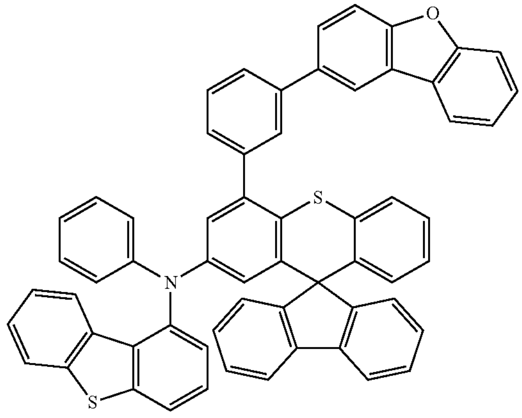

-continued
A-54
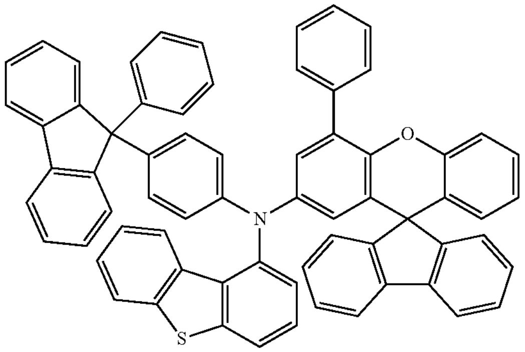
A-55
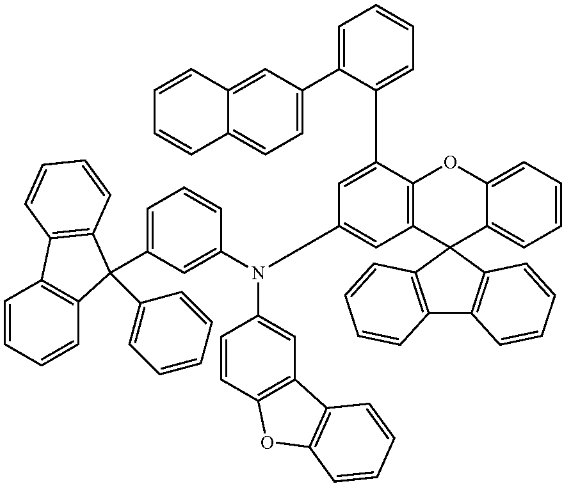
A-56
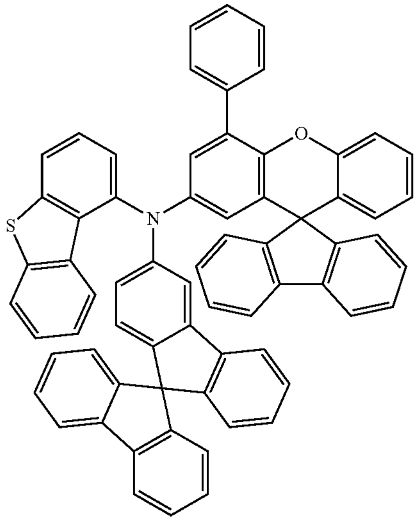
-continued
A-57
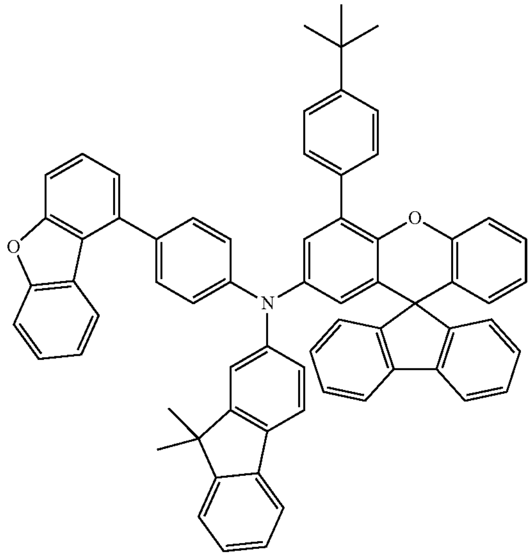
A-58
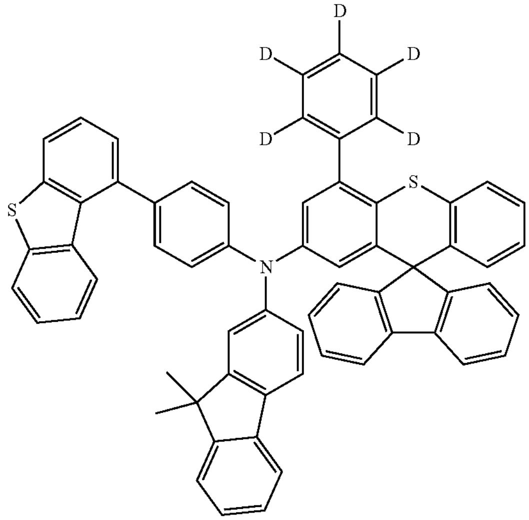

-continued
A-59
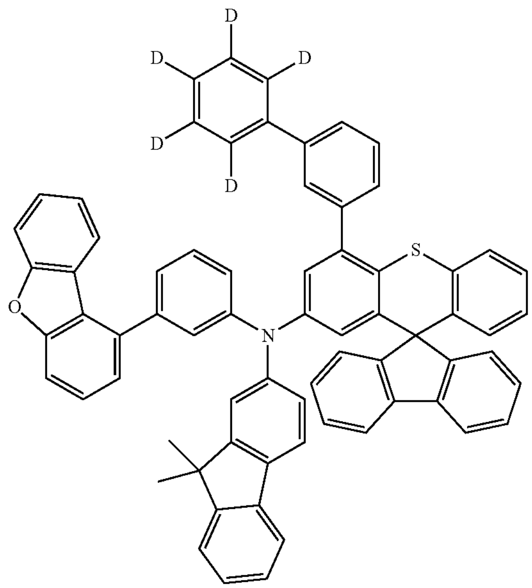
A-60
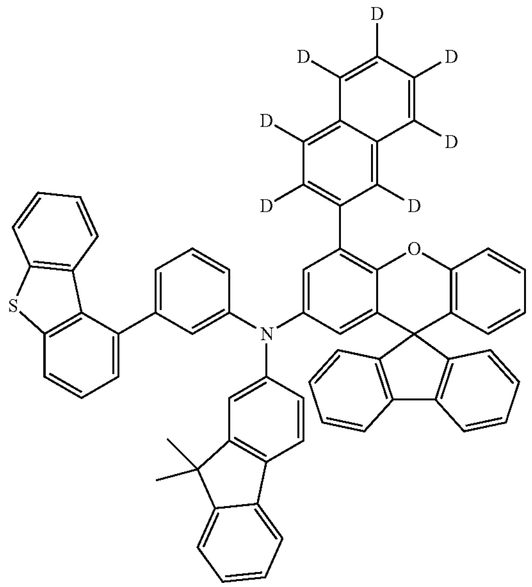
-continued
A-61
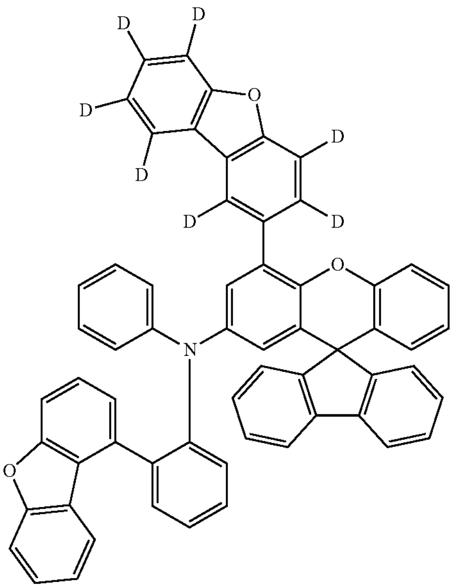
A-62
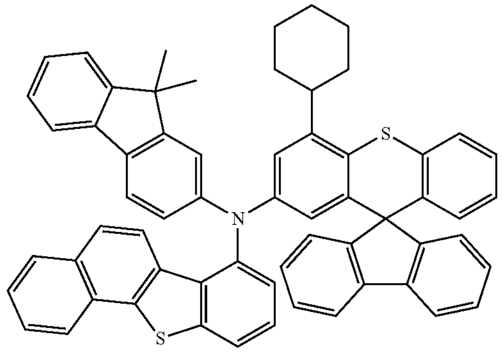
A-63
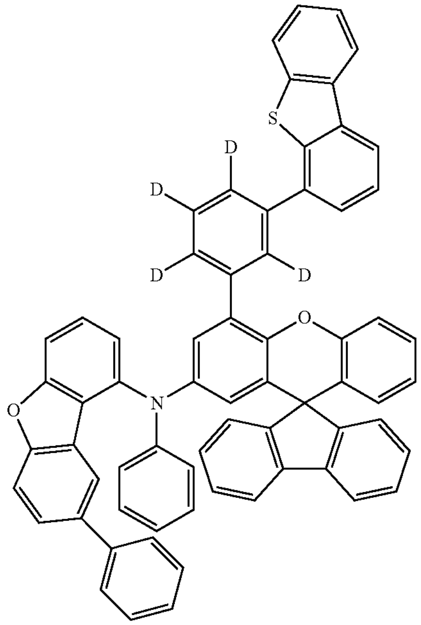

-continued
A-64
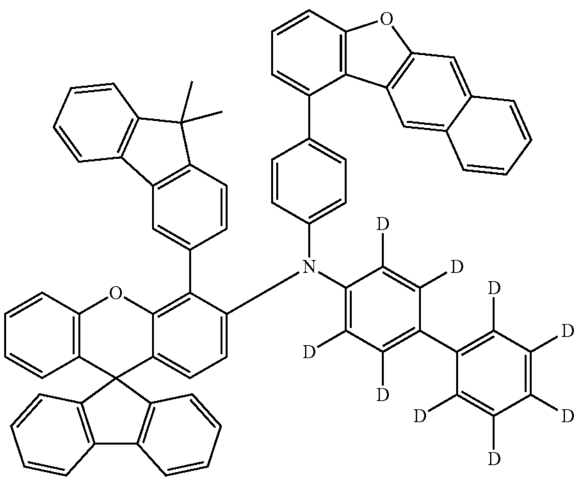
A-65
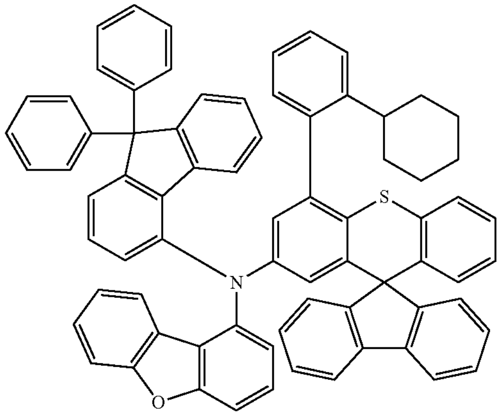
A-66
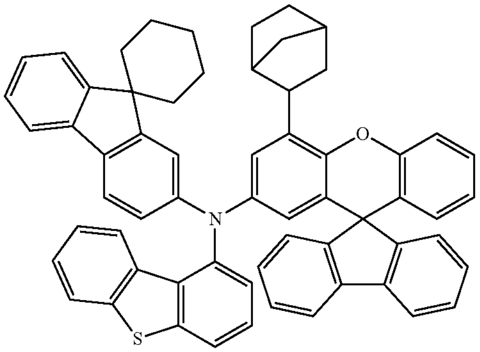
-continued
A-67
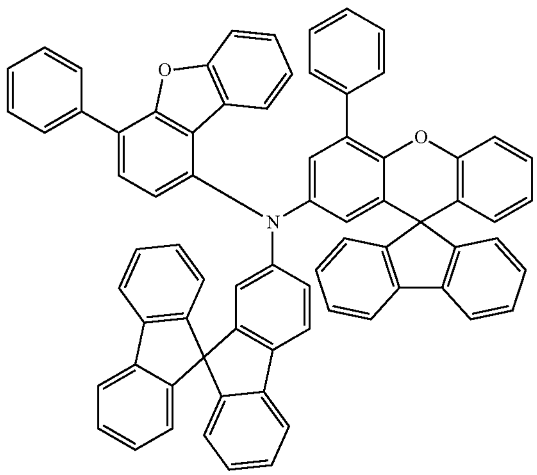
A-68
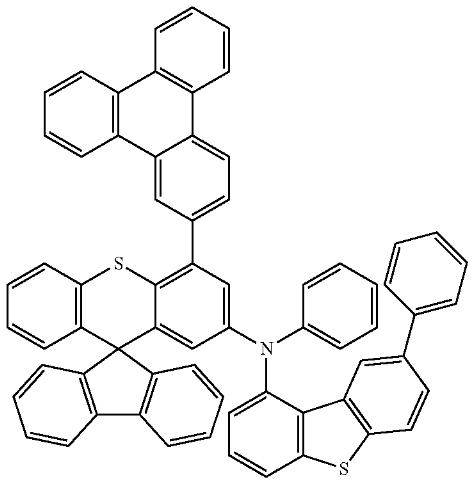
A-69
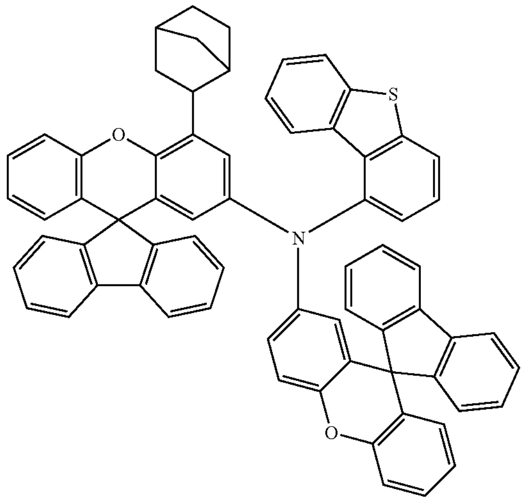

-continued
A-70
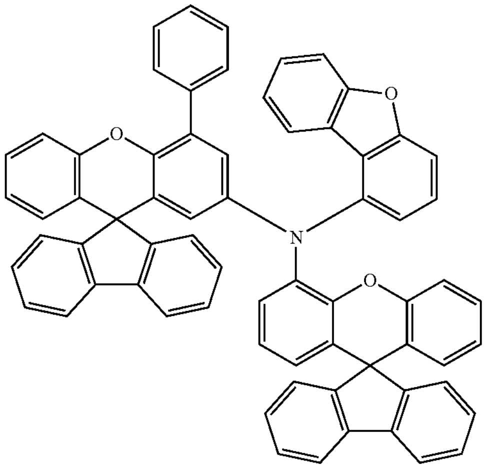
A-71
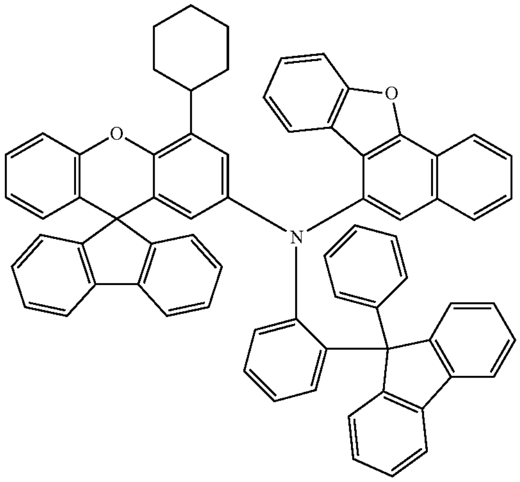
A-72
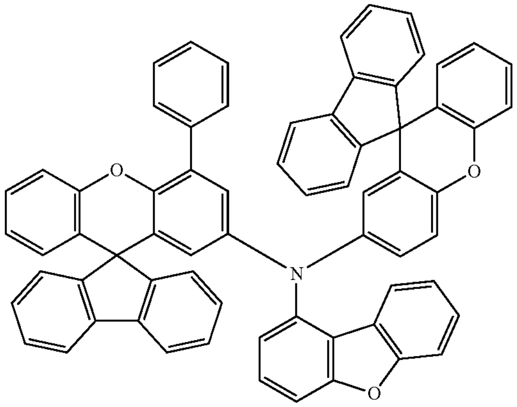
-continued
A-73
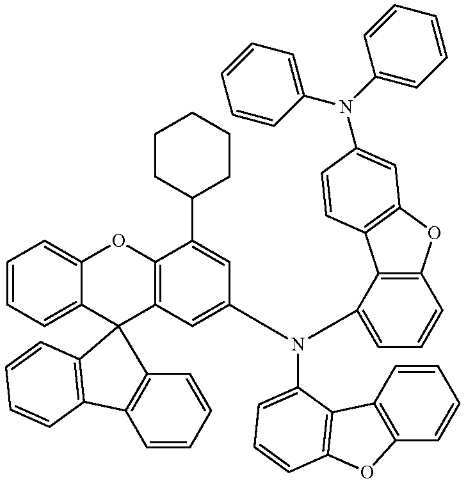
A-74
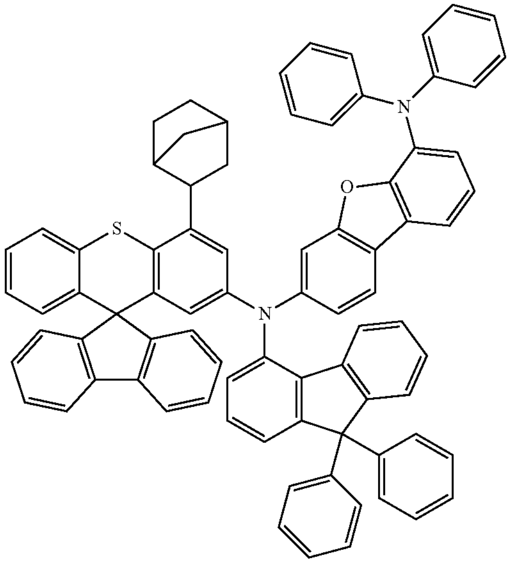

-continued
A-75
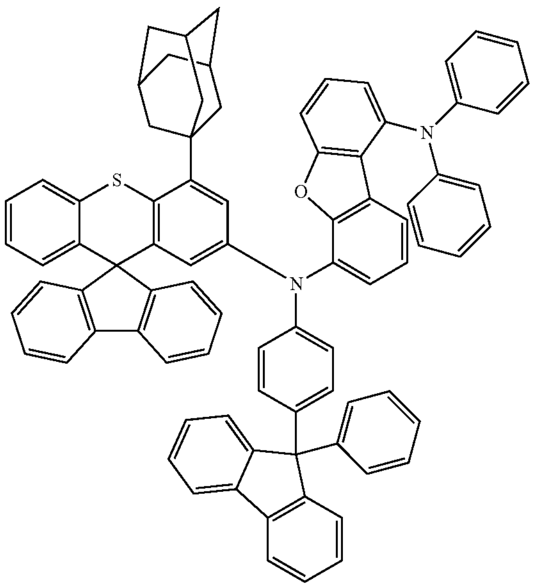
A-76
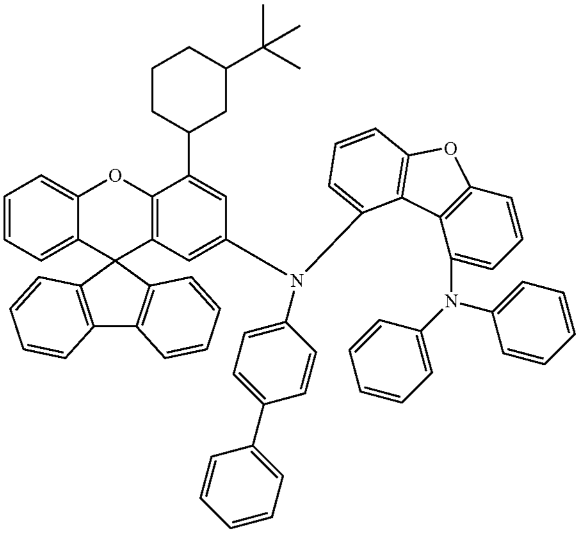
-continued
A-77
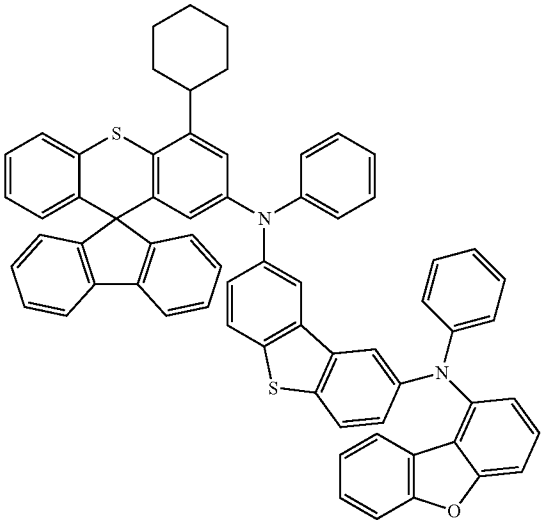
A-78
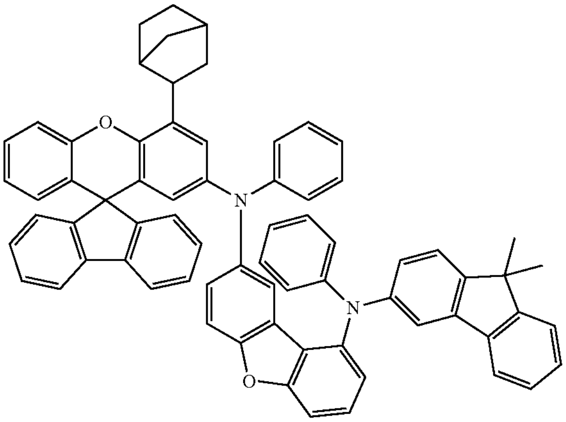
A-79
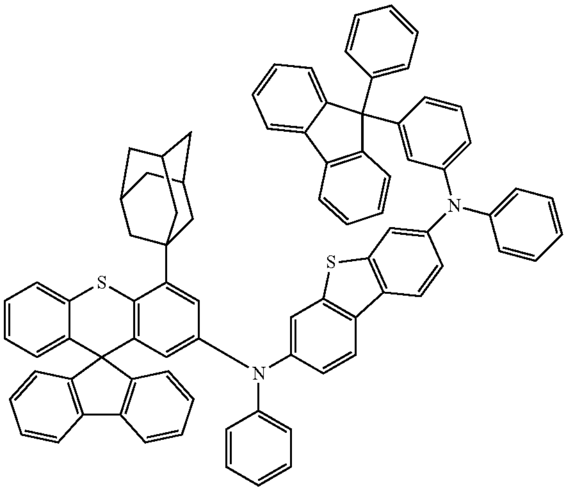

-continued
A-80
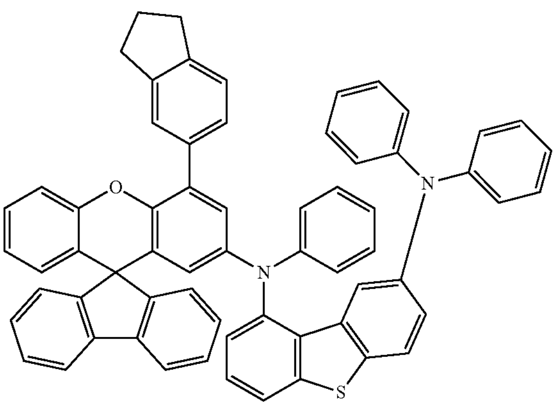
A-81
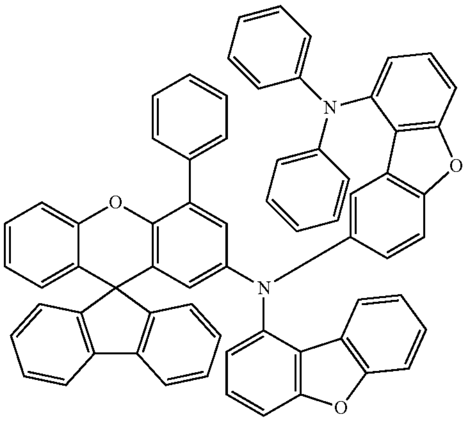
A-82
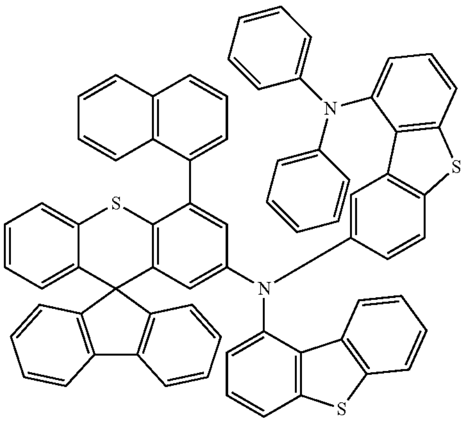
-continued
A-83
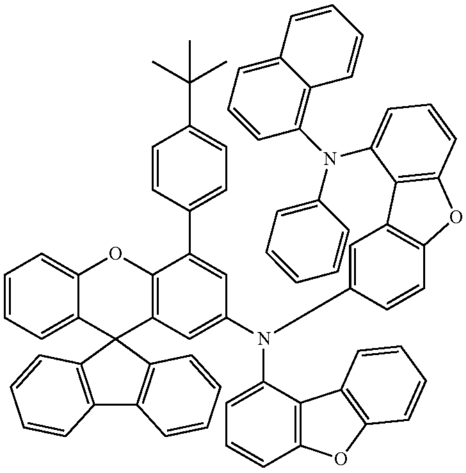
A-84
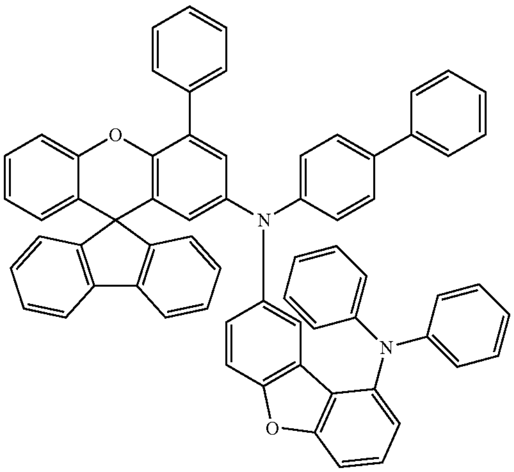
A-85
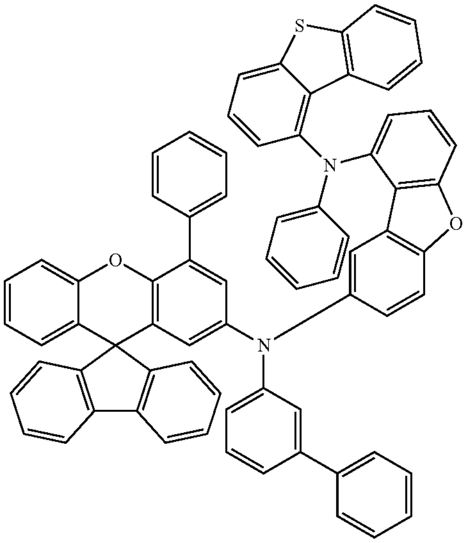

-continued
A-86
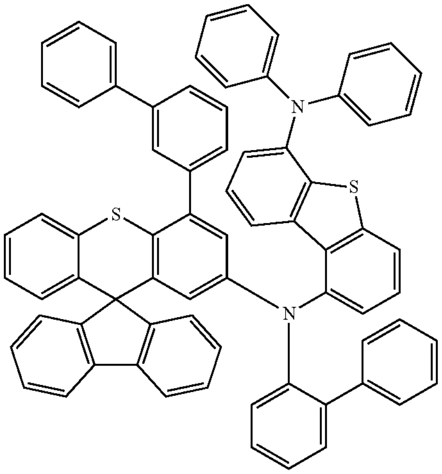
A-87
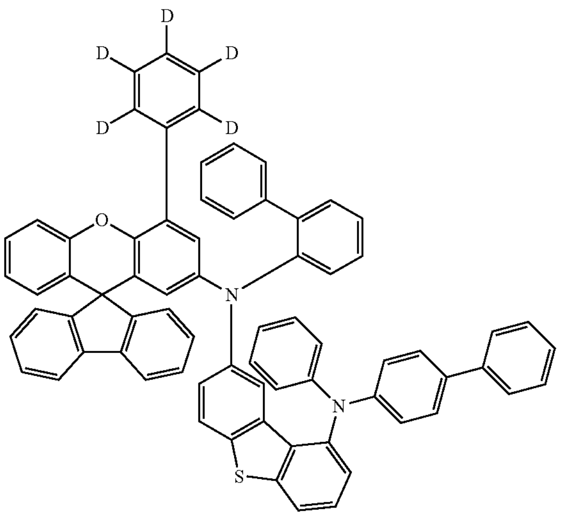
A-88
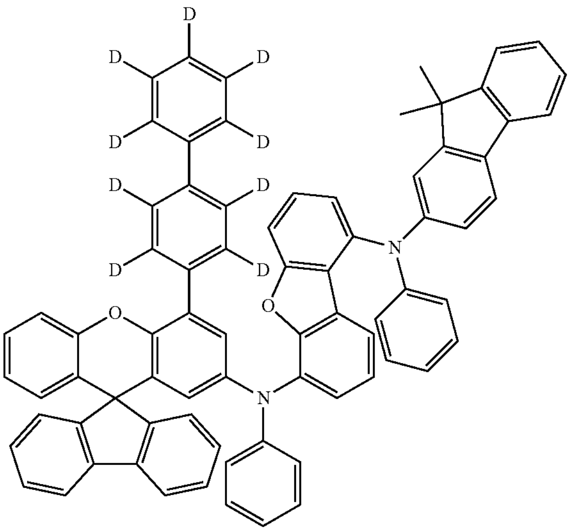
-continued
A-89
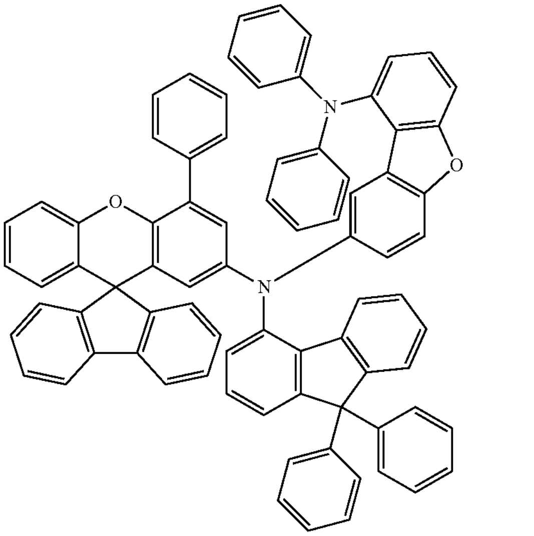
A-90
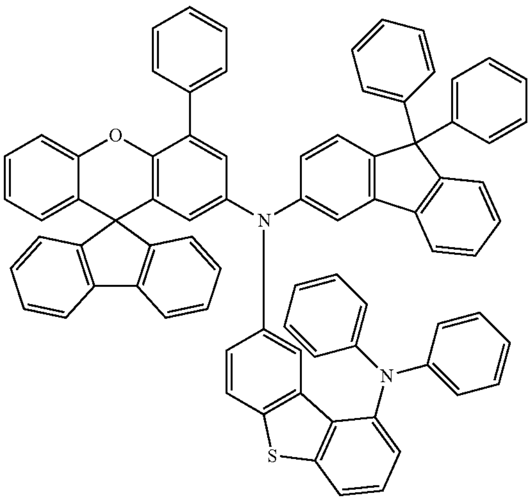
A-91
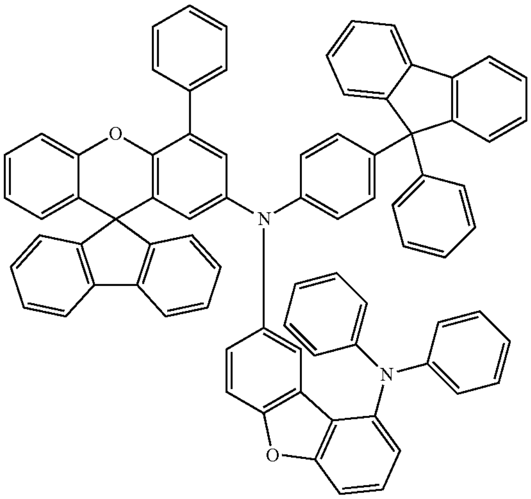

-continued
A-92
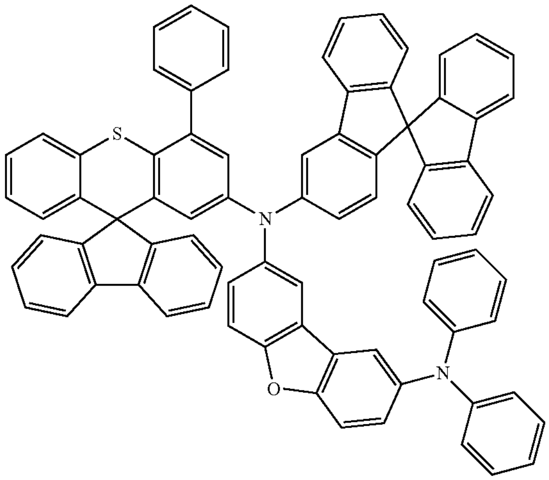
A-93
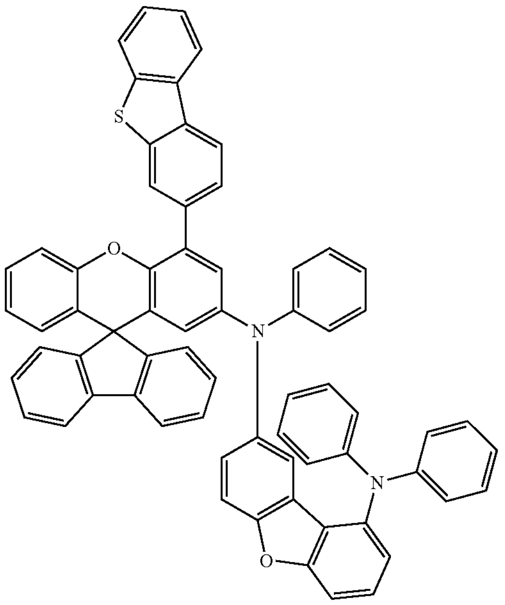
-continued
A-94
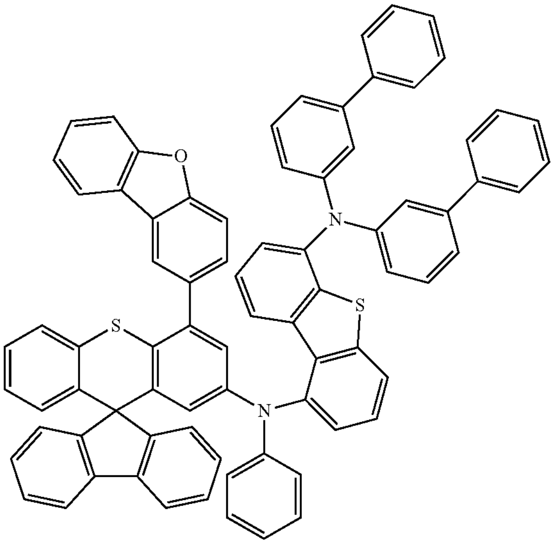
A-95
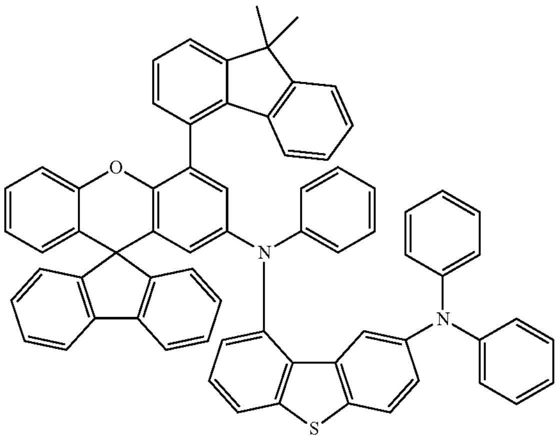
A-96
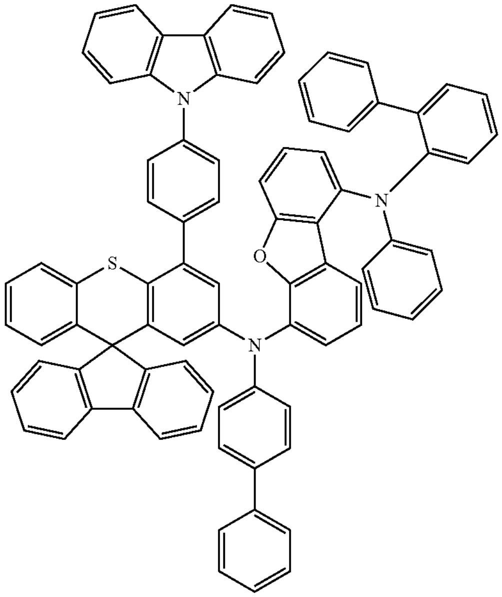

-continued
A-97
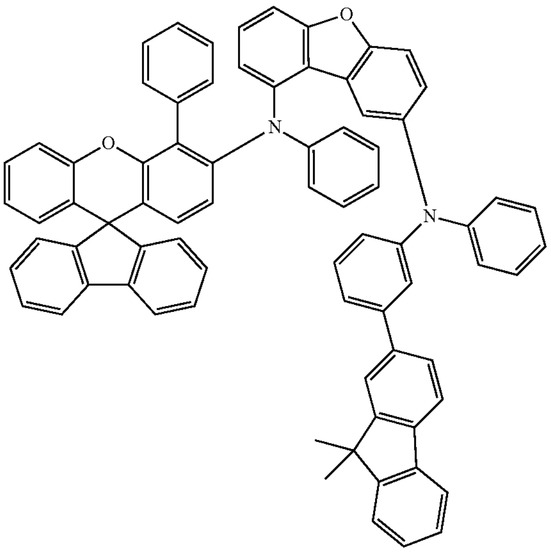
A-98
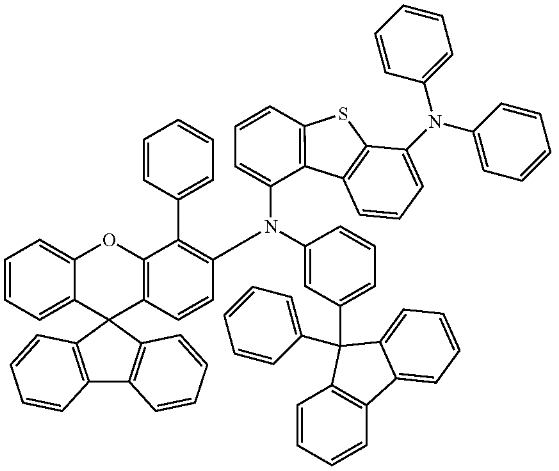
A-99
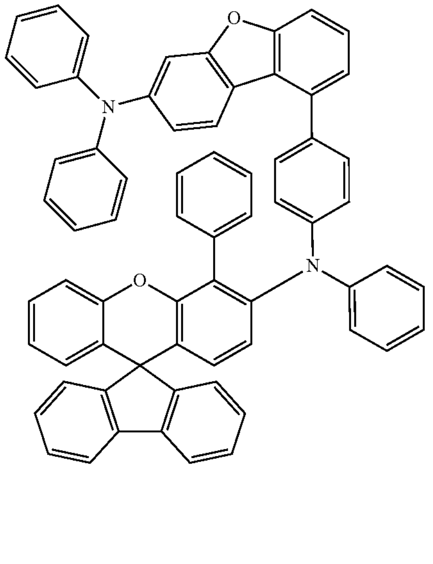
-continued
A-100
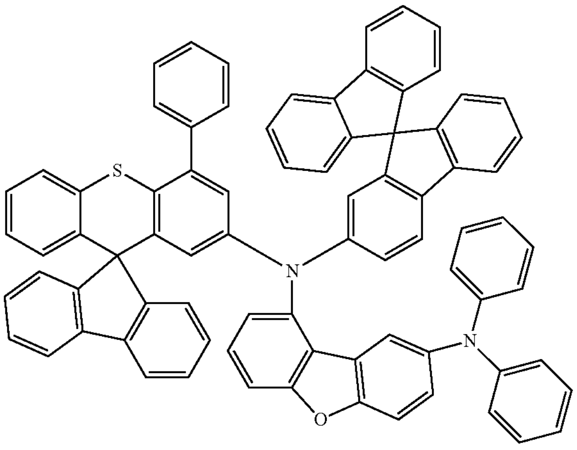
A-101
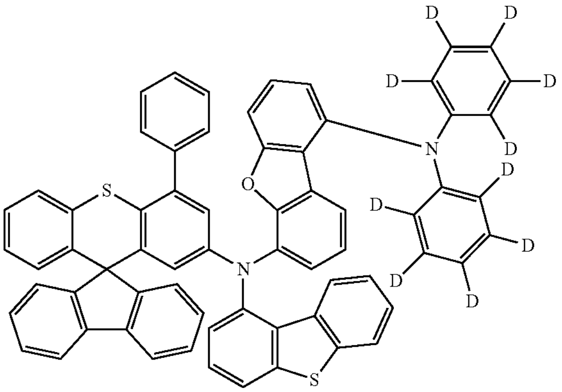
A-102
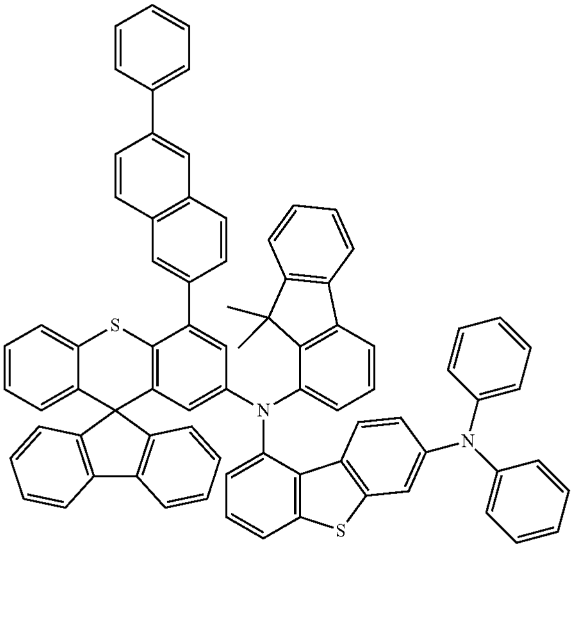

-continued
A-103
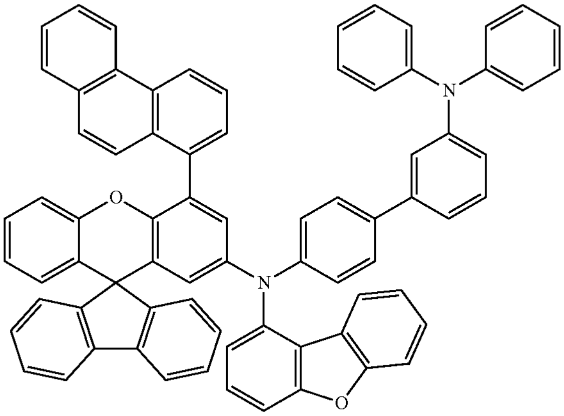
A-104
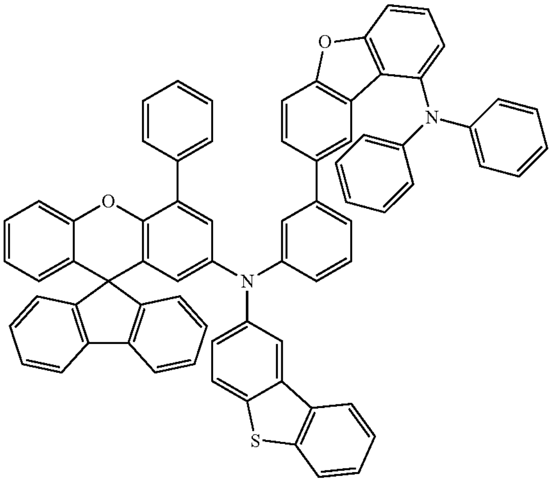
A-105
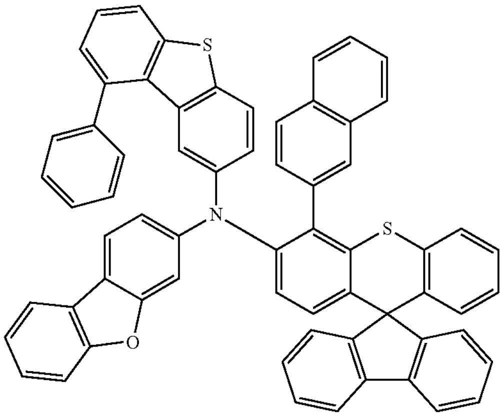
-continued
A-106
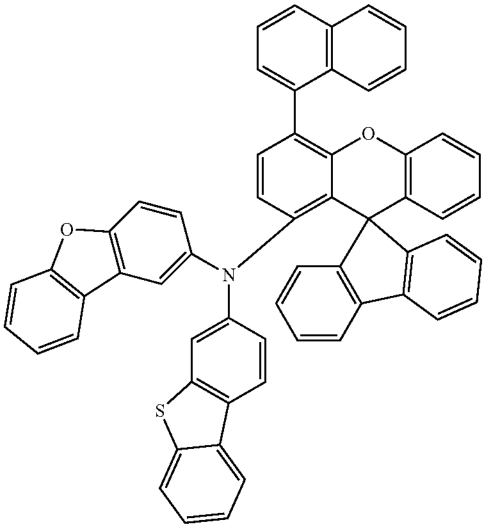
A-107
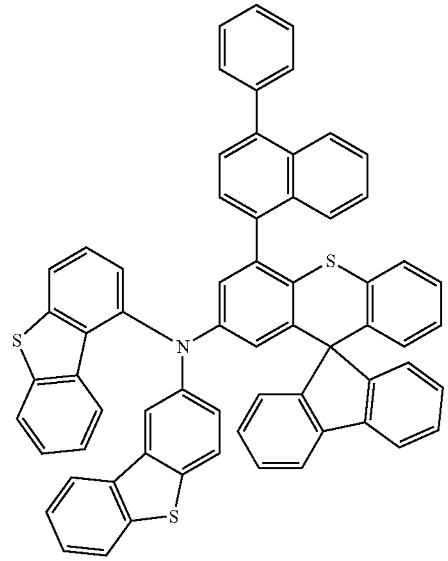
A-108
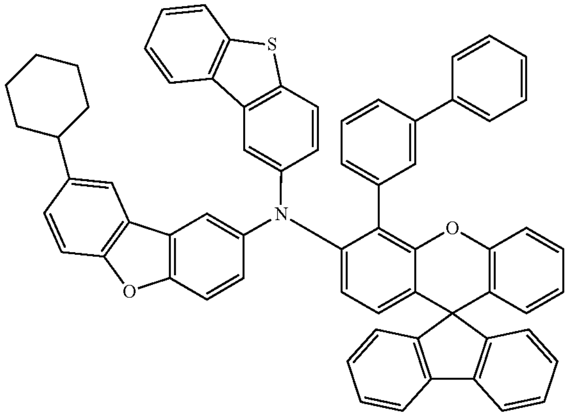

-continued

A-109

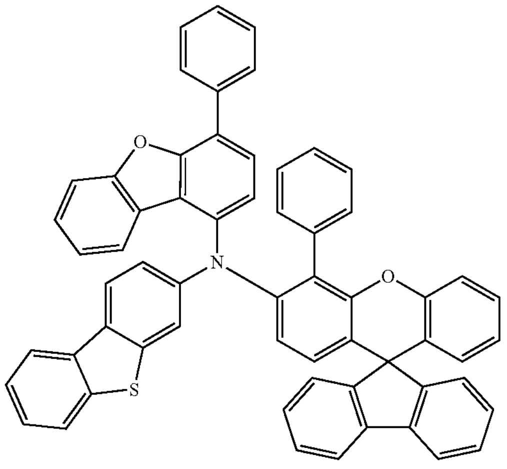

A-110

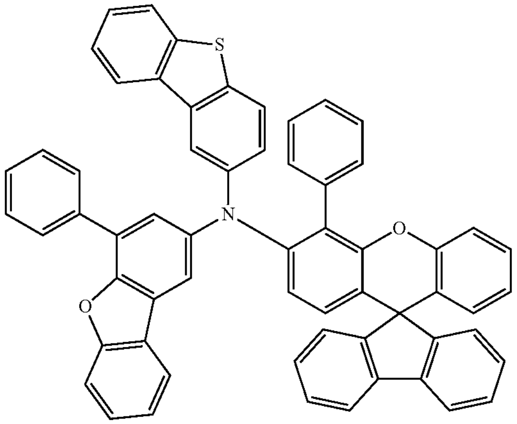

A-111

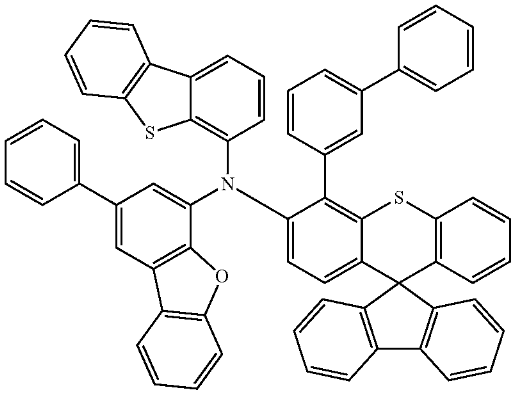

-continued

A-112

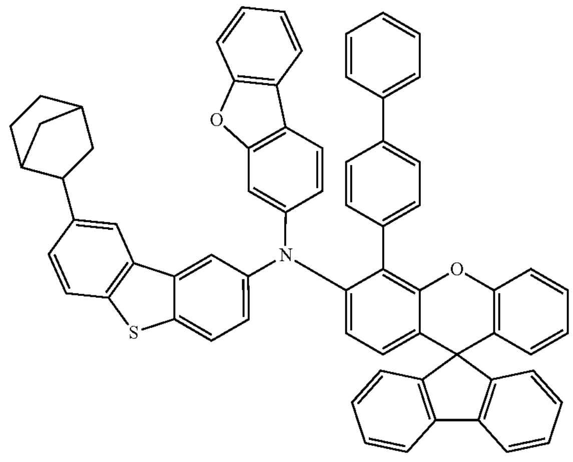

Also, in another aspect, in the manufacturing process of the organic light emitting device, the present invention provides a method of reusing the compound represented by Formula A comprising:

the step of depositing an organic light emitting material including the compound represented by Formula A;

the step of removing impurities of the crude organic light emitting material recovered from the deposition apparatus;

the step of recovering the removed impurities;

and the step of purifying the recovered impurities to a purity of 99.9% or more;

The step of removing impurities of the crude organic light emitting material recovered from the deposition apparatus may include performing a pre-refining process to obtain a purity of 98% or more by recrystallization preferably in a recrystallization solvent.

The recrystallization solvent may preferably be a polar solvent having a polarity index (PI) of 5.5 to 7.2.

Preferably, the recrystallization solvent may be used by mixing a polar solvent having a polarity value of 5.5 to 7.2 and a non-polar solvent having a polarity value of 2.0 to 4.7.

When the recrystallization solvent is used by mixing a polar solvent and a non-polar solvent, the non-polar solvent may be used in a ratio of 15% (v/v) or less compared to the polar solvent.

Wherein the recrystallization solvent may be used single; or a mixed non-polar solvent; or a mixture of a polar solvent and a non-polar solvent selected from the group consisting of N-Methylpyrrolidone (NMP) single solvent; or a mixed polar solvent in which any one selected from the group consisting of dimethyl imidazolidinone (1,3-Dimethyl-2-imidazolidinone), 2-pyrrolidone, dimethylformamide (N,N-dimethyl formamide), dimethyl acetamide and dimethyl sulfoxide is mixed to the methylpyrrolidone; or toluene, Dichloromethane (DCM), Dichloroethane (DCE), Tetrahydrofuran (THF), Chloroform, Ethyl acetate and Butanone.

The preliminary refining process may comprise the step of cooling to 0° C. to 5° C. to precipitate crystals, after dissolving the crude organic light emitting material recovered from the deposition apparatus in a polar solvent at 90° C. to 120° C.

The preliminary refining process may comprise the step of cooling to 35° C. to 40° C., adding a non-polar solvent, and then cooling to 0° C. to 5° C. to precipitate crystals, after dissolving the crude organic light emitting material recovered from the deposition apparatus in a polar solvent at 90° C. to 120° C.

The preliminary purification process may comprise the step of precipitating crystals while concentrating the solvent and removing the non-polar solvent, after dissolving the crude organic light emitting material recovered from the deposition apparatus in a non-polar solvent, The preliminary purification process may comprise the step of recrystallization again with a non-polar solvent, after recrystallization first with a polar solvent The step of purifying the recovered impurities to a purity of 99.9% or more may include the step of performing an adsorption separation process for adsorbing and removing impurities by adsorbing them to an adsorbent.

The adsorbent may be activated carbon, silica gel, alumina or a material for known adsorption applications.

The step of purifying the recovered impurities to a purity of 99.9% or more may include performing sublimation purification.

Referring to FIG. 1, the organic electronic element (100) according to the present invention includes a first electrode (110), a second electrode (170), an organic material layer comprising single compound represented by Formula A or 2 or more compounds between the first electrode (110) and the second electrode (170), Here, the first electrode (110) may be an anode or a positive electrode, and the second electrode (170) may be a cathode or a negative electrode.

In the case of an inverted organic electronic element, the first electrode may be a cathode, and the second electrode may be an anode.

Figure 2:
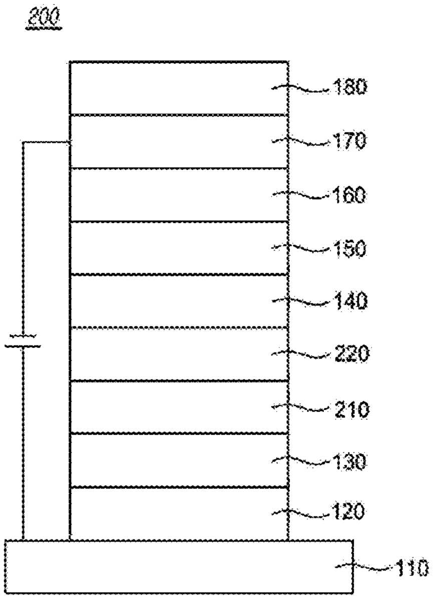

The organic material layer may sequentially include a hole injection layer (120), a hole transport layer (130), an emitting layer (140), an electron transport layer(150), and an electron injection layer (160) formed in sequence on the first electrode(110). Here, the remaining layers except the emitting layer (140) may not be formed. The organic material layer may further include a hole blocking layer, an electron blocking layer, an emitting-auxiliary layer (220), a buffer layer (210), etc., and the electron transport layer (150) and the like may serve as a hole blocking layer (see FIG. 2).

Also, the organic electronic element according to an embodiment of the present invention may further include a protective layer or a light efficiency enhancing layer (180). The light efficiency enhancing layer may be formed on a surface not in contact with the organic material layer among both surfaces of the first electrode or on a surface not in contact with the organic material layer among both surfaces of the second electrode. The compound according to an embodiment of the present invention applied to the organic material layer may be used as a material for a hole injection layer (120), a hole transport layer (130), an emitting-auxiliary layer (220), an electron transport auxiliary layer, an electron transport layer (150), an electron injection layer (160), a host or dopant of an emitting layer (140) or the light efficiency enhancing layer. Preferably, for example, the compound according to Formula A of the present invention may be used as a material for the emitting-auxiliary layer.

Figure 3:
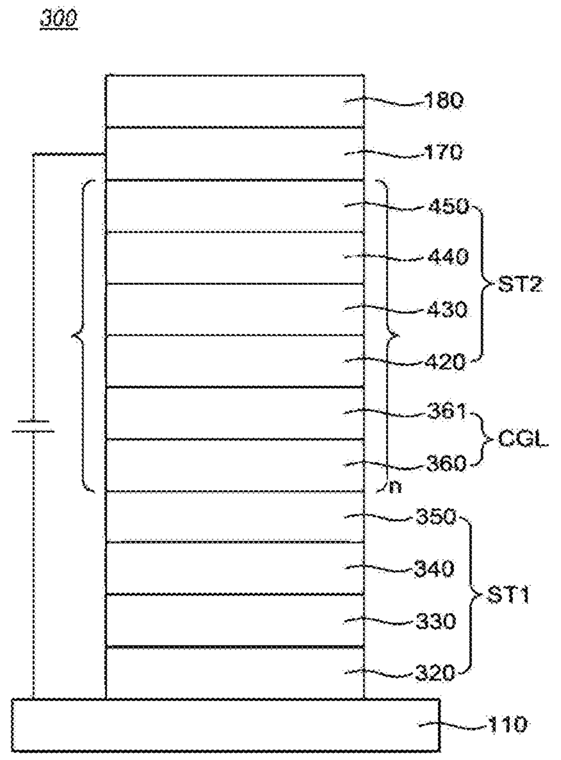

The organic material layer may include 2 or more stacks including a hole transport layer, an emitting layer, and an electron transport layer sequentially formed on the anode, and may further include a charge generation layer formed between the 2 or more stacks (see FIG. 3).

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials(mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer(120), the hole transport layer(130), the emitting layer (140), the electron transport layer(150), and the electron injection layer(160) is formed thereon, and then depositing a material usable as a cathode thereon can manufacture an organic electroluminescent device according to an embodiment of the present invention.

Also, the present invention provides the organic electronic element wherein the organic material layer is formed by one of a spin coating process, a nozzle printing process, an inkjet printing process, a slot coating process, a dip coating process or a roll-to-roll process, and the organic material layer provides an organic electronic element comprising the compound as an electron transport material.

As another specific example, the present invention provides an organic electronic element that is used by mixing the same or different compounds of the compound represented by Formula A to the organic material layer.

In another aspect, the present invention provides an emitting-auxiliary layer composition comprising a compound represented by Formula A, and provides an organic electronic element comprising the emitting-auxiliary layer.

Also, the present invention also provides an electronic device comprising a display device including the organic electronic element; and a control unit for driving the display device.

According to another aspect, the present invention provides an display device wherein the organic electronic element is at least one of an OLED, an organic solar cell, an organic photo conductor, an organic transistor(organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant(PDA), an electronic dictionary, a point-to-multipoint(PMP), a remote controller, a navigation unit, a game player, various kinds of TVs, and various kinds of computers.

Hereinafter, Synthesis Examples of the compound represented by Formula A of the present invention and preparation examples of the organic electronic element of the present invention will be described in detail by way of example, but are not limited to the following examples.

Synthesis Example

The compound (Final product) represented by Formula A according to the present invention may be prepared by reacting as in Reaction Scheme 1, but is not limited thereto. (Hal=Br or Cl)

<Reaction Scheme 1>
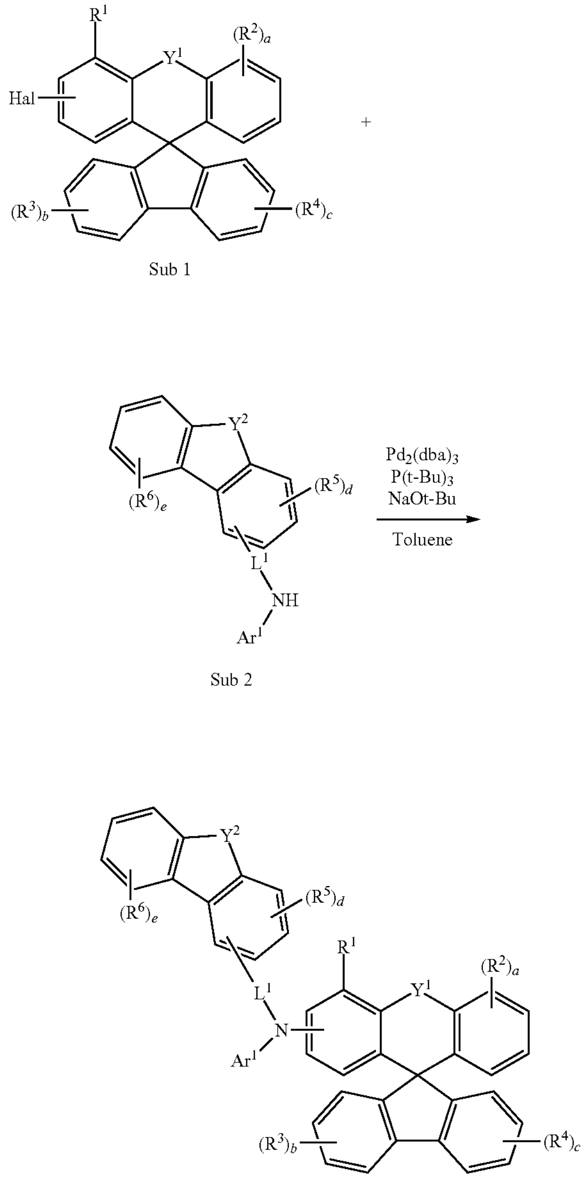
I. Synthesis of Sub 1
Sub 1 of Reaction Scheme 1 may be synthesized by the reaction route of Scheme 2, but is not limited thereto. When $X^1$ is —OH, Sub 1 of Reaction Scheme 1 is synthesized by the synthesis route of (1), and when $X^1$ is —SH, Sub 1 of Reaction Scheme 1 is synthesized by the synthesis route of (2).
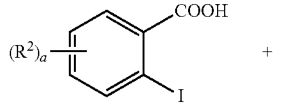
-continued
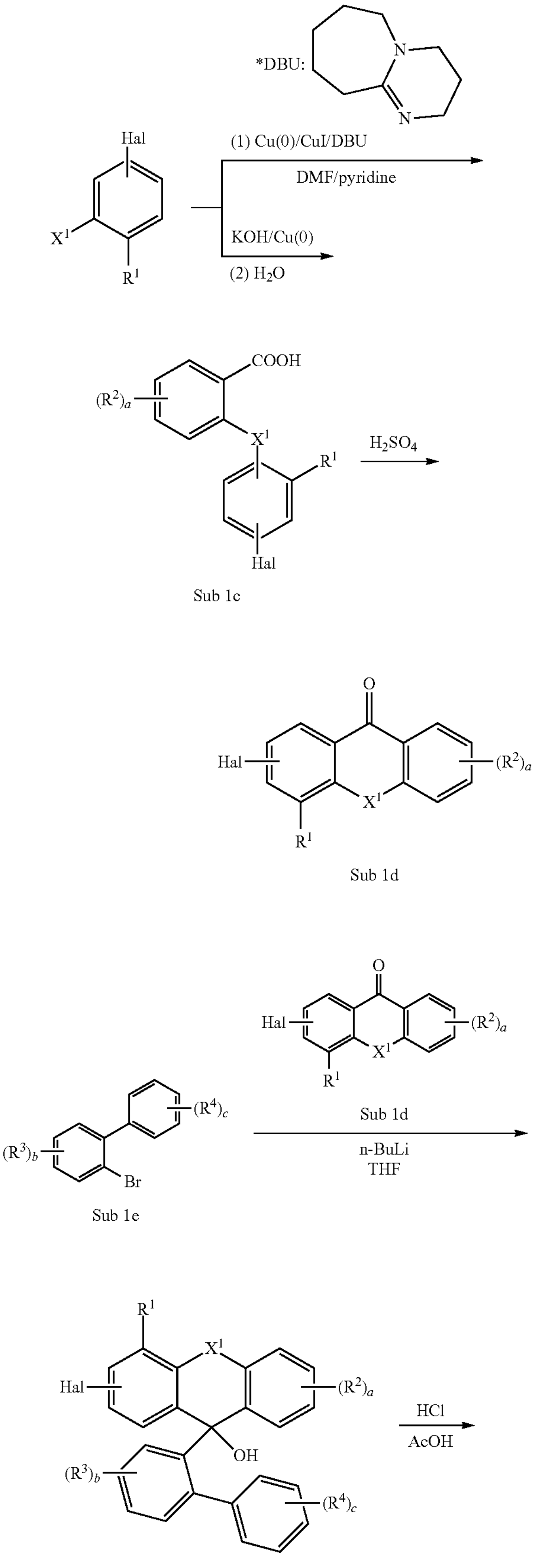

-continued

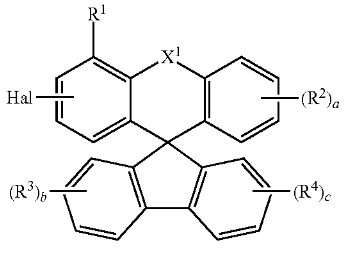

Sub 1

1. Synthesis Example of Sub1-1

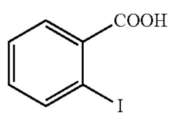

Sub 1a-1

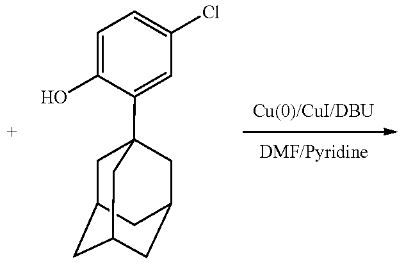

Sub 1b-1

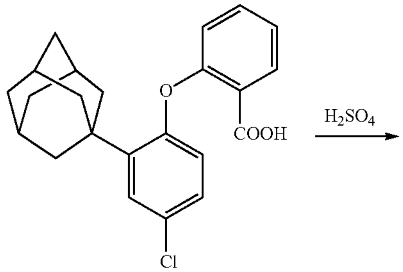

Sub 1c-1

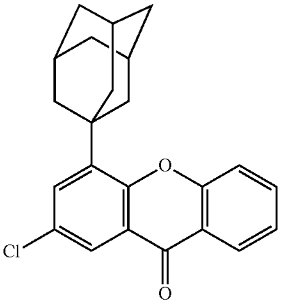

Sub 1d-1

-continued

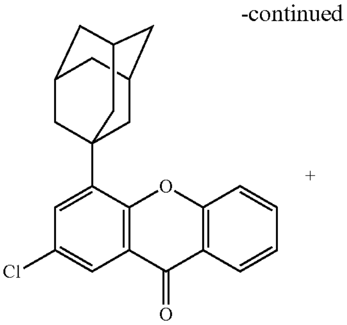

Sub 1d-1

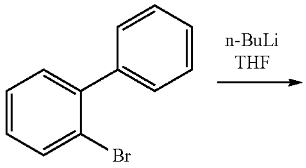

Sub 1e-1

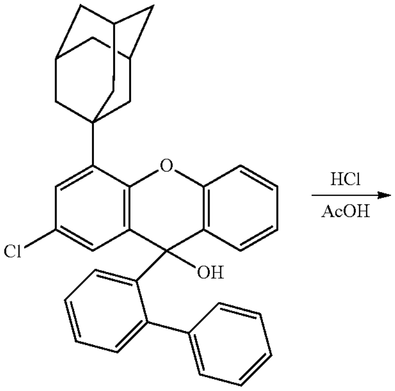

Sub 1f-1

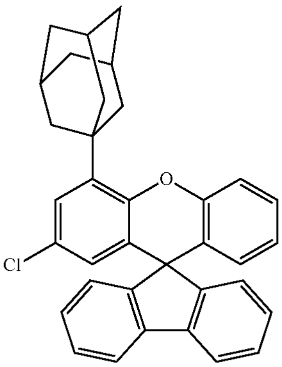

Sub 1-1

(1) Synthesis Example of Sub 1c-1

Sub 1a-1 (13.0 g, 52.4 mmol), Sub 1b-1 (27.6 g, 104.8 mmol), 1,8-diazabicyclo[5.4.0]undec-7-ene (DBU) (23.9 g, 157.3 mmol), pyridine (0.9 mL), Copper powder (0.4 g, 6.8 mmol), CuI (0.5 g, 2.4 mmol) were placed in a round flask, DMF (260 mL) was added, and refluxed for 3 hours. When the reaction is complete, after cooling to room temperature, 3M HCl is added until the precipitation is complete. Then, the precipitate was washed with water and dried to obtain 16.8 g (yield: 84%) of the product.

(2) Synthesis Example of Sub 1d-1

The obtained Sub 1c-1 (16.8 g, 43.9 mmol) was placed in a round-bottom flask, $H_2SO_4$ (0.3 mL, 6.1 mmol) was added, and refluxed until all the starting materials were dissolved. When all the starting materials were dissolved, cool to room temperature, and then add ice water to precipitate. Thereafter, the precipitate was washed with water, dried, dissolved in $CH_2Cl_2$, and recrystallized by silicagel column to obtain 10.9 g (yield: 68%) of the product.

(3) Synthesis Example of Sub 1f-1

Sub 1e-1 (7.0 g, 29.9 mmol) was dissolved in THF (100 mL) in a round-bottom flask under nitrogen atmosphere, and then cooled to −78° C. After that, n-BuLi (12.1 mL) is slowly titrated and the mixture is stirred for 30 minutes. Then, after dissolving Sub 1d-1 (10.9 g, 29.9 mmol) obtained in the above synthesis in THF (200 mL), and then slowly titrate to the reacting round-bottom flask. After stirring for an additional 1 hour at −78° C., slowly raise to room temperature.

When the reaction is complete, the mixture was extracted with ethyl acetate and water, the organic layer was dried over $MgSO_4$, concentrated, and the resulting compound was recrystallized by silicagel column to obtain 11.3 g (yield: 73%) of the product.

(4) Synthesis Example of Sub 1-1

The obtained Sub 1f-1 (11.3 g, 21.8 mmol), acetic acid (52 mL) and concentrated hydrochloric acid (8.7 mL) were put in a round-bottom flask and stirred at 60-80° C. under nitrogen atmosphere for 3 hours. When the reaction is complete, the mixture was extracted with $CH_2C_{12}$ and water, the organic layer was dried over $MgSO_4$, concentrated, and the resulting compound was recrystallized by silicagel column to obtain 27.7 g (yield: 91%) of the product.

2. Synthesis Example of Sub1-6

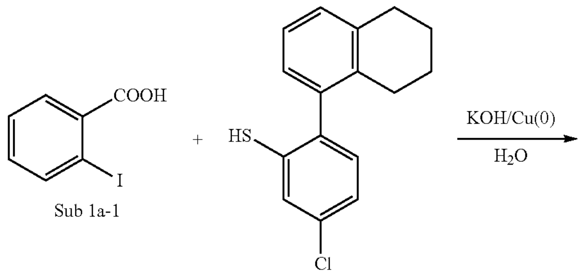

Sub 1a-1

Sub 1b-6

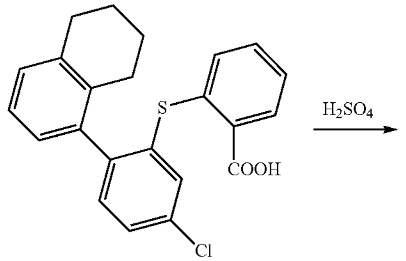

Sub 1c-6

-continued

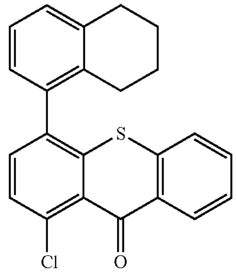

Sub 1d-6

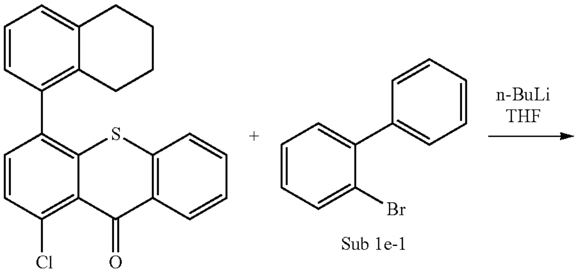

Sub 1d-6

Sub 1e-1

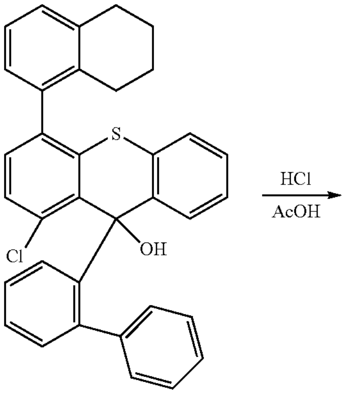

Sub 1f-6

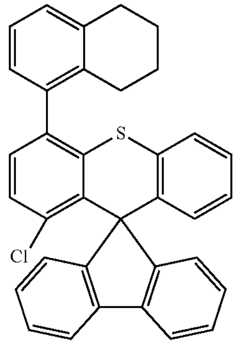

Sub 1-6

(1) Synthesis Example of Sub 1c-6

Sub 1a-1 (20.0 g, 80.6 mmol), Sub 1b-6 (22.2 g, 80.6 mmol), Potassium hydroxide (22.6 g, 403.2 mmol), Copper powder (0.5 g, 8.1 mmol) were placed in a round flask, water (400 mL) was added, and refluxed for 12 hours. When the reaction is complete, after cooling to room temperature, 3M HCl is added until the precipitation is complete. Then, the precipitate was washed with water and dried to obtain 25.1 g (yield: 79%) of the product.

(2) Synthesis Example of Sub 1d-6

The obtained Sub1c-6 (25.1 g, 63.6 mmol) and $H_2SO_4$ (0.5 mL) were used for the synthesis of Sub 1d-1 to obtain 16.7 g (70% yield) of a product.

(3) Synthesis Example of Sub 1f-6

Sub 1e-1 (10.3 g, 44.3 mmol), n-BuLi (17.9 mL), the obtained Sub 1d-6 (16.7 g, 44.3 mmol) were used for the synthesis of Sub 1f-1 to obtain 16.9 g (72% yield) of a product.

(4) Synthesis Example of Sub 1-6

The obtained Sub 1f-6 (16.9 g, 31.8 mmol), acetic acid (75.8 mL) and concentrated hydrochloric acid (12.7 mL) were used for the synthesis of Sub 1-1 to obtain 13.2 g (yield: 810%) of the product.

3. Synthesis Example of Sub1-10

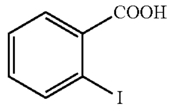

Sub 1a-1

+

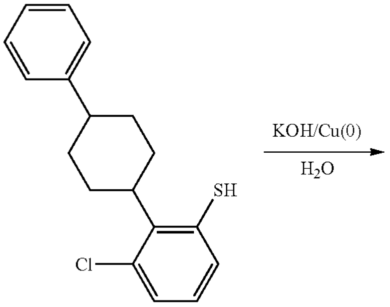

Sub 1b-10

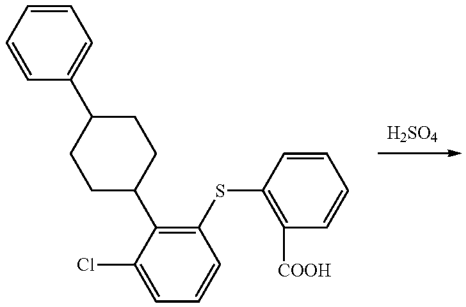

Sub 1c-10

-continued

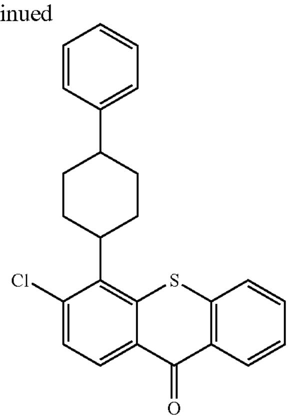

Sub 1d-10

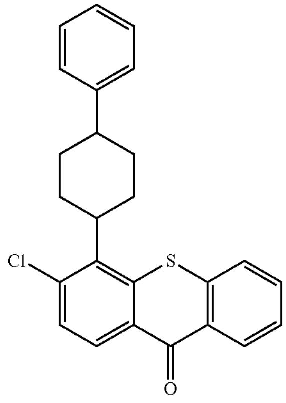

Sub 1d-10

+

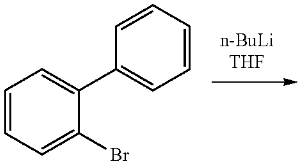

Sub 1e-1

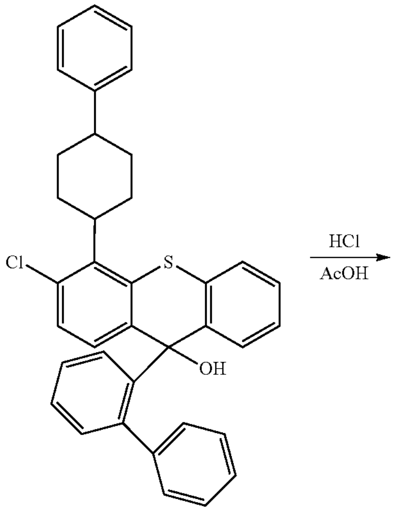

Sub 1f-10

-continued

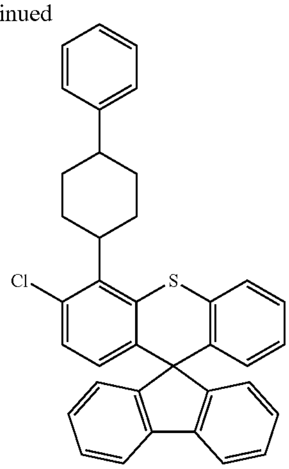

Sub 1-10

(1) Synthesis Example of Sub 1c-10

Sub 1a-1 (10.0 g, 40.3 mmol), Sub 1b-10 (12.2 g, 40.3 mmol), Potassium hydroxide (11.3 g, 201.6 mmol), Copper powder (0.26 g, 4.0 mmol) were used for the synthesis of Sub 1c-6 to obtain 13.6 g (yield: 80%) of the product.

(2) Synthesis Example of Sub 1d-10

The obtained Sub 1c-10 (13.6 g, 32.2 mmol), $H_2SO_4$ (0.24 mL) were used for the synthesis of Sub 1d-1 to obtain 8.9 g (yield: 69%) of the product.

(3) Synthesis Example of Sub 1f-10

Sub 1e-1 (5.1 g, 22.0 mmol), n-BuLi (8.9 mL), the obtained Sub 1d-10 (8.9 g, 22.0 mmol) were used for the synthesis of Sub 1f-1 to obtain 9.2 g (yield: 75%) of the product.

(4) Synthesis Example of Sub 1-10

The obtained Sub 1f-10 (9.2 g, 16.5 mmol), acetic acid (39.2 mL), and concentrated hydrochloric acid (6.6 mL) were used for the synthesis of Sub 1-1 to obtain 7.6 g (yield: 86%) of the product.

4. Synthesis Example of Sub 1-20

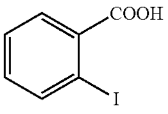

+

Sub 1a-1

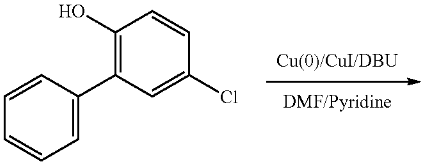

Sub 1b-20

-continued

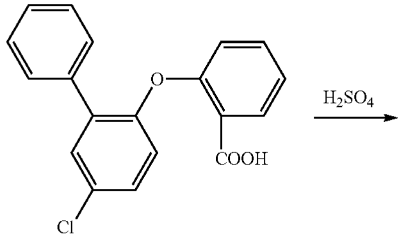

Sub 1c-20

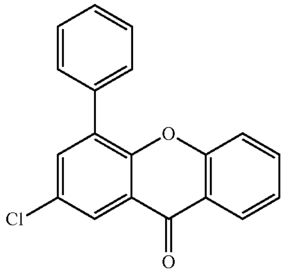

Sub 1d-20

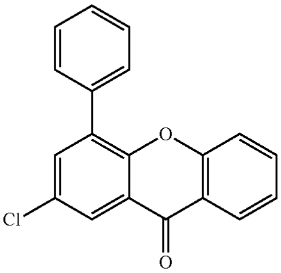

+

Sub 1d-20

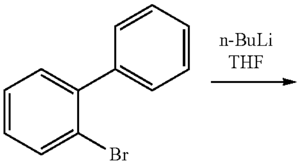

Sub 1e-1

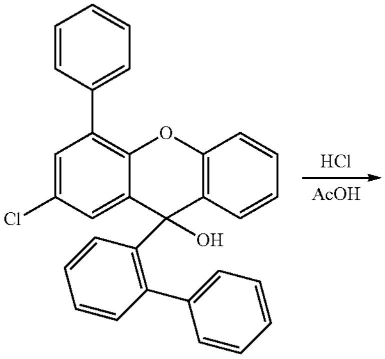

Sub 1f-20

-continued

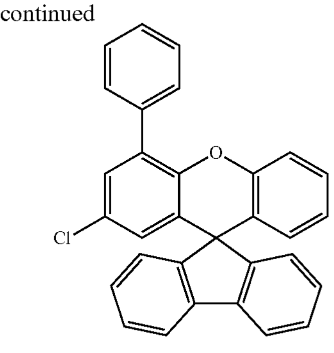

Sub 1-20

(1) Synthesis Example of Sub 1c-20

Sub 1a-1 (15.0 g, 60.5 mmol), Sub 1b-20 (24.8 g, 121.0 mmol), 1,8-diazabicyclo[5.4.0]undec-7-ene (DBU) (27.6 g, 181.4 mmol), pyridine (0.98 mL), Copper powder (0.5 g, 7.9 mmol), CuI (0.5 g, 2.7 mmol) were used for the synthesis of Sub 1c-1 to obtain 16.1 g (yield: 82%) of the product.

(2) Synthesis Example of Sub 1d-20

The obtained Sub 1c-20 (16.1 g, 49.6 mmol) and $H_2SO_4$ (0.37 mL) were used for the synthesis of Sub 1d-1 to obtain 10.8 g (yield: 71%) of the product.

(3) Synthesis Example of Sub 1f-20

Sub 1e-1 (8.2 g, 35.2 mmol), n-BuLi (14.2 mL), the obtained Sub 1d-20 (10.8 g, 35.2 mmol) were used for the synthesis of Sub 1f-1 to obtain 12.5 g (yield: 77%) of the product.

(4) Synthesis Example of Sub 1-20

The obtained Sub 1f-20 (12.5 g, 27.1 mmol), acetic acid (64.6 mL), and concentrated hydrochloric acid (10.8 mL) were used for the synthesis of Sub 1-1 to obtain 10.8 g (yield: 90%) of the product.

5. Synthesis Example of Sub 1-33

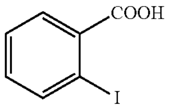

Sub 1a-1

+

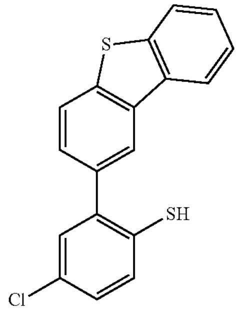

Sub 1b-33

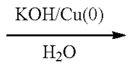

-continued

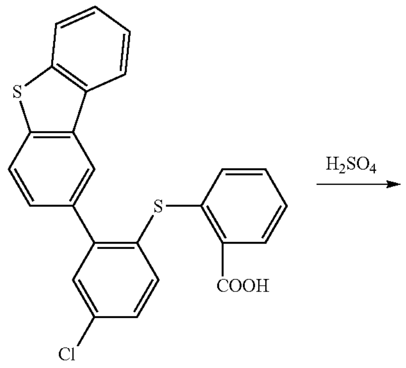

Sub 1c-33

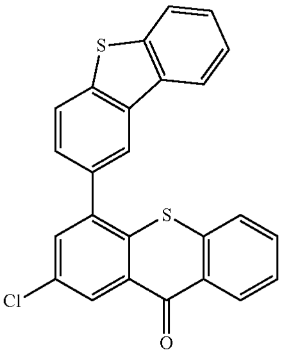

Sub 1d-33

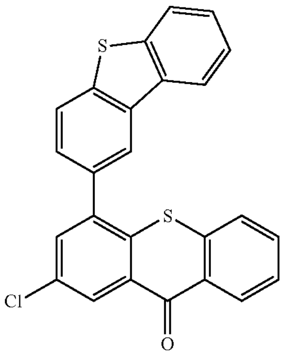

Sub 1d-33

+

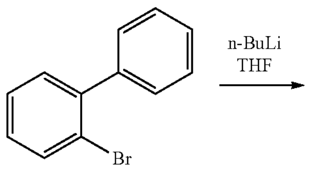

Sub 1e-1

-continued

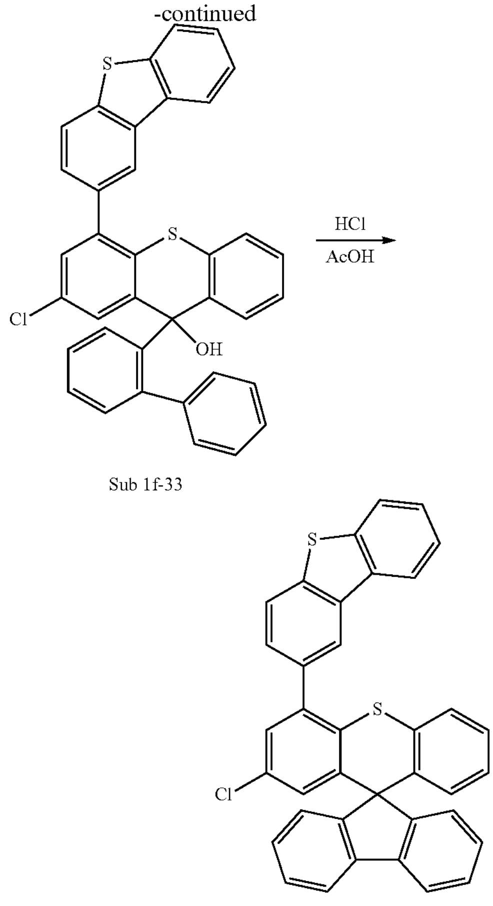

Sub 1f-33

Sub 1-33

(1) Synthesis Example of Sub 1c-33

Sub 1a-1 (13.0 g, 52.4 mmol), Sub 1b-33 (17.1 g, 52.4 mmol), Potassium hydroxide (14.7 g, 262.1 mmol), Copper powder (0.3 g, 5.2 mmol) were used for the synthesis of Sub 1c-6 to obtain 19.4 g (yield: 83%) of the product.

(2) Synthesis Example of Sub 1d-33

Sub 1c-33 (19.4 g, 43.4 mmol) and $H_2SO_4$ (0.32 mL) were used for the synthesis of Sub 1d-1 to obtain 13.4 g (yield: 72%) of the product.

(3) Synthesis Example of Sub Lf-33

Sub 1e-1 (7.3 g, 31.2 mmol), n-BuLi (12.6 mL), the obtained Sub 1d-33 (13.4 g, 31.2 mmol) were used for the synthesis of Sub 1f-1 to obtain 13.8 g (yield: 76%) of the product.

(4) Synthesis Example of Sub 1-33

The obtained Sub 1f-33 (13.8 g, 23.7 mmol), acetic acid (56.3 mL), and concentrated hydrochloric acid (9.5 mL) were used for the synthesis of Sub 1-1 to obtain 11.7 g (yield: 88%) of the product.

Meanwhile, the compound belonging to Sub 1 may be a compound as follows, but is not limited thereto, and Table 1 shows FD-MS (Field Desorption-Mass Spectrometry) values of the compound belonging to Sub 1.

Sub 1-1

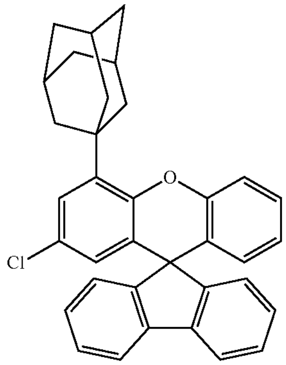

Sub 1-2

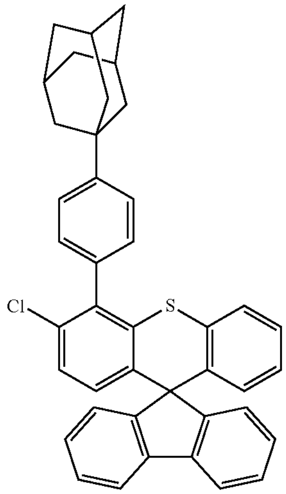

Sub 1-3

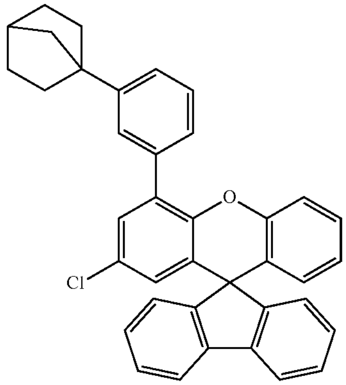

Sub 1-4

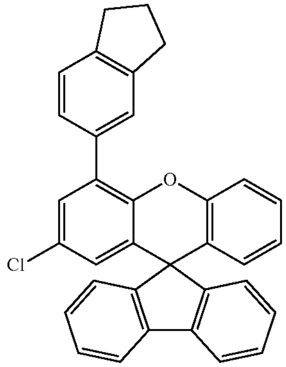

-continued
Sub 1-5
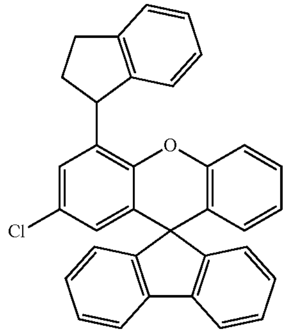
Sub 1-6
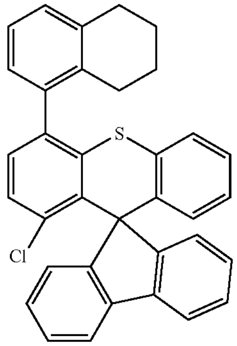
Sub 1-7
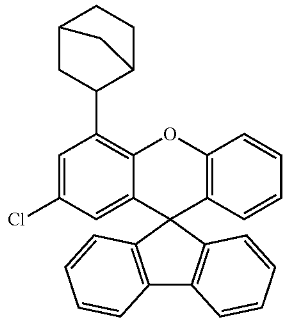
Sub 1-8
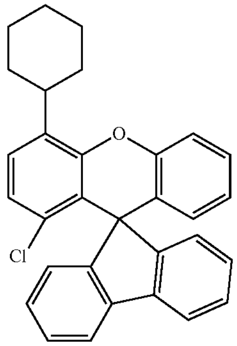
-continued
Sub 1-9
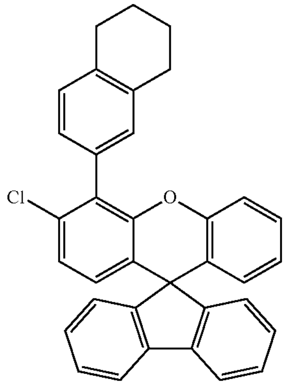
Sub 1-10
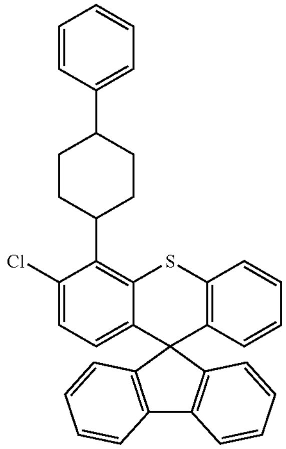
Sub 1-11
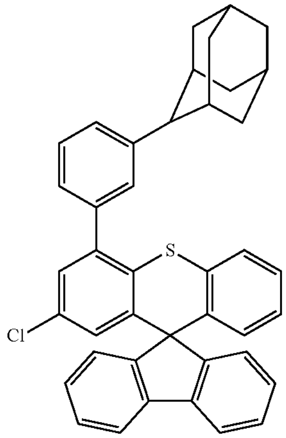

-continued
Sub 1-12
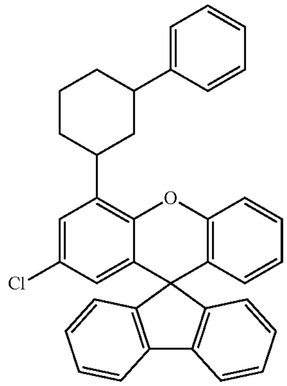
Sub 1-13
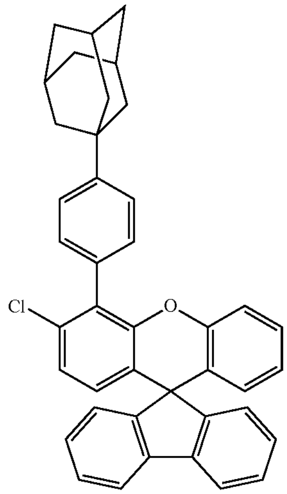
Sub 1-14
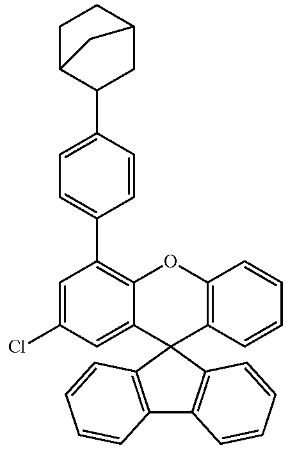
-continued
Sub 1-15
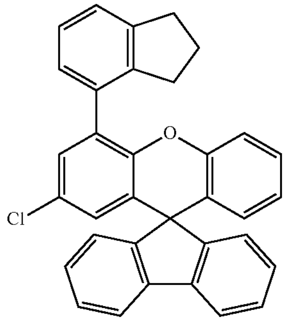
Sub 1-16
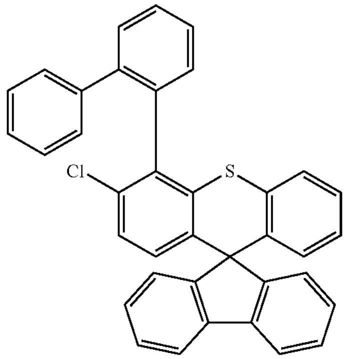
Sub 1-17
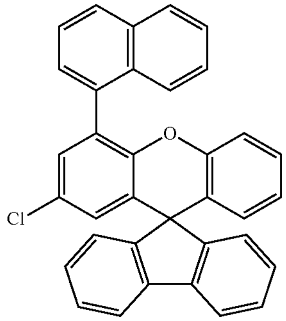
Sub 1-18
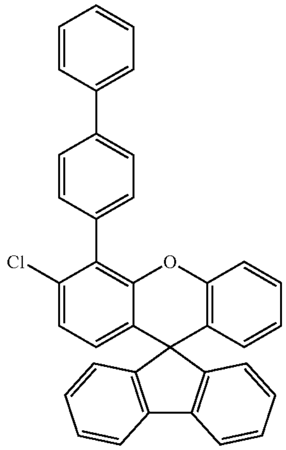

-continued
Sub 1-19
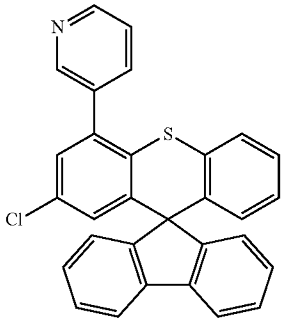
Sub 1-20
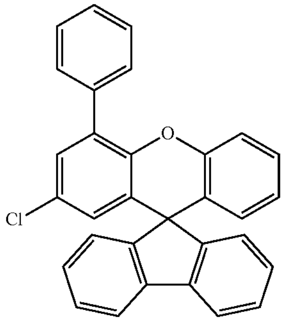
Sub 1-21
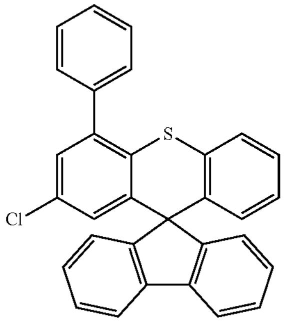
Sub 1-22
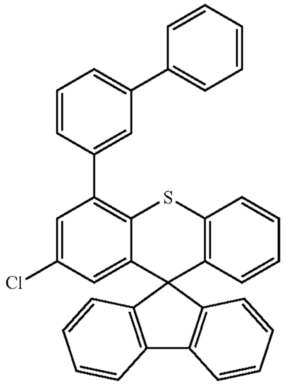
-continued
Sub 1-23
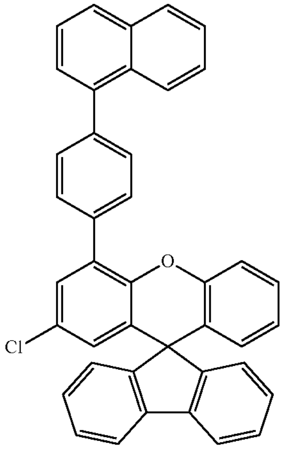
Sub 1-24
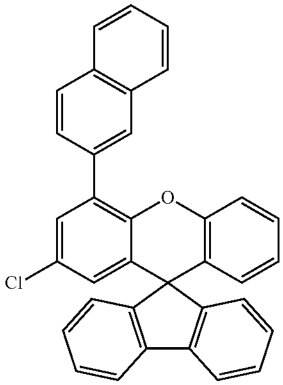
Sub 1-25
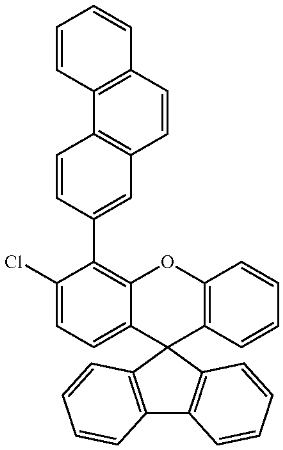

-continued
Sub 1-26
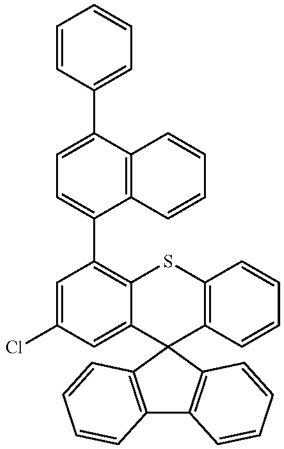
Sub 1-27
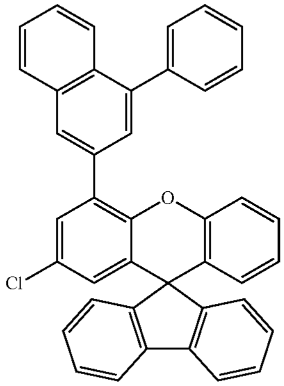
Sub 1-28
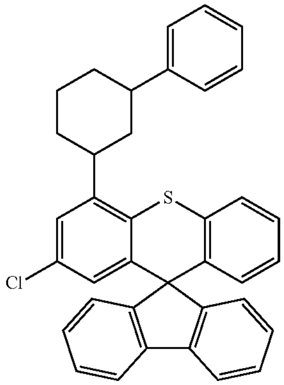
Sub 1-29
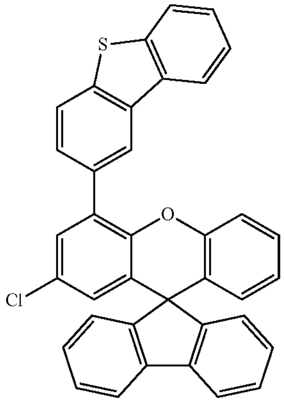
-continued
Sub 1-30
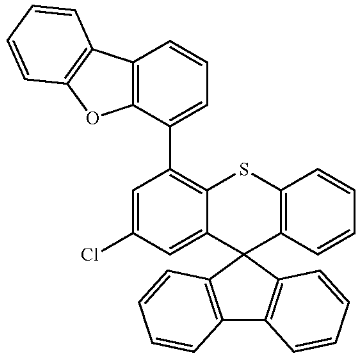
Sub 1-31
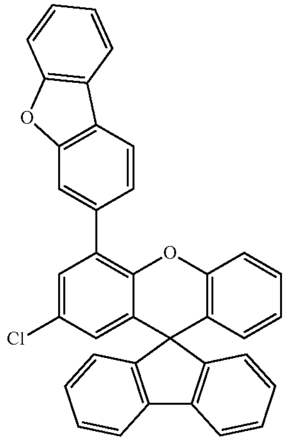
Sub 1-32
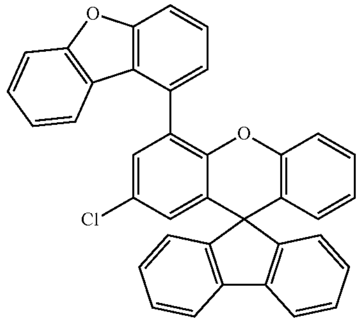
Sub 1-33
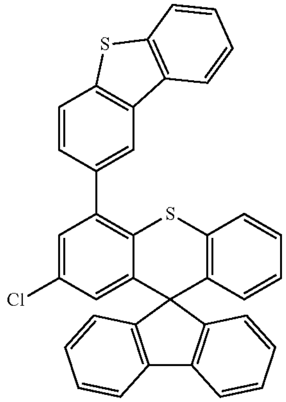

-continued
Sub 1-34
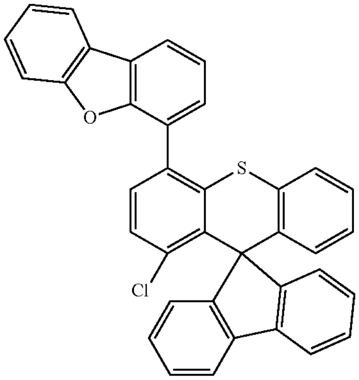
Sub 1-35
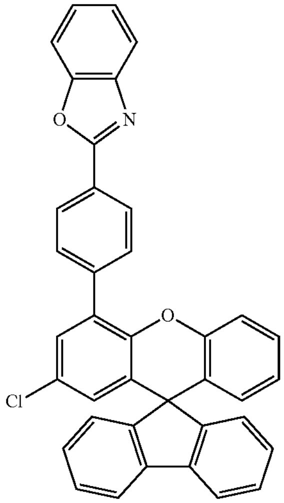
Sub 1-36
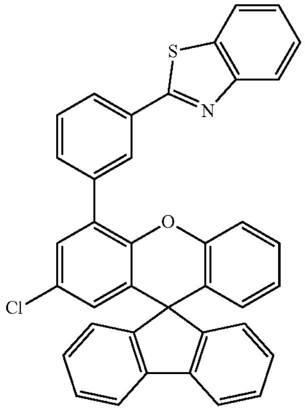
-continued
Sub 1-37
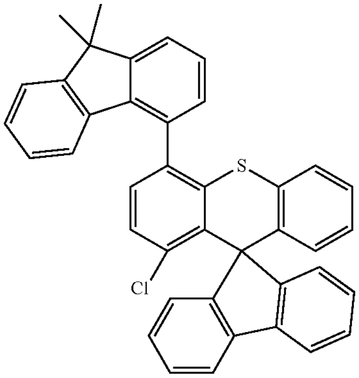
Sub 1-38
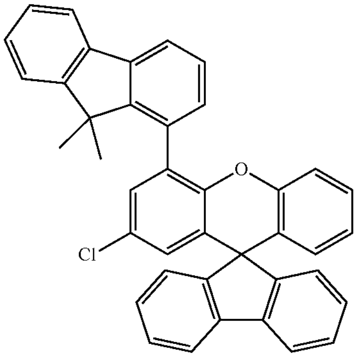
Sub 1-39
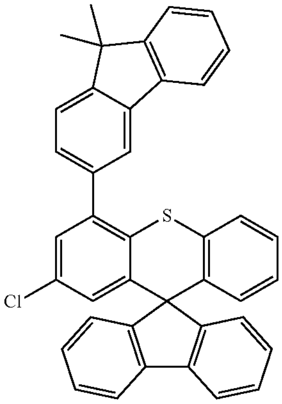
Sub 1-40
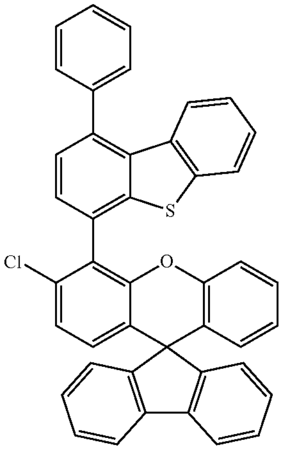

-continued
Sub 1-41
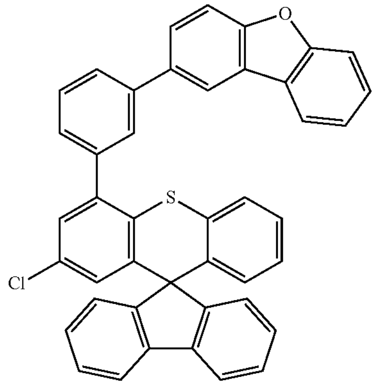
Sub 1-42
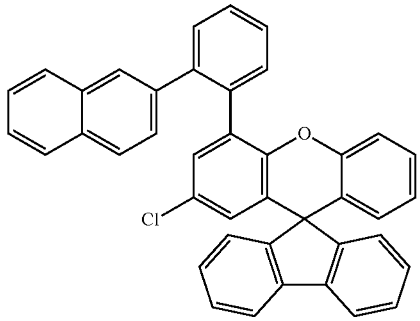
Sub 1-43
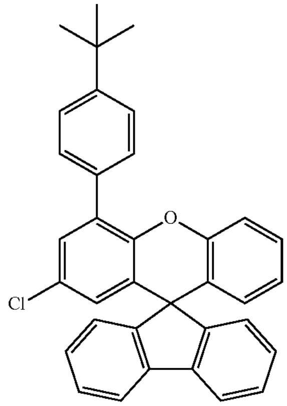
Sub 1-44
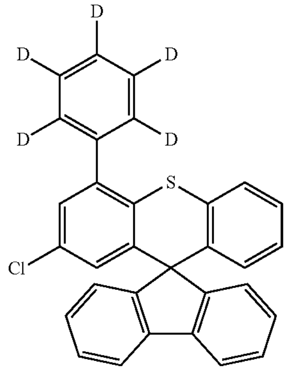
-continued
Sub 1-45
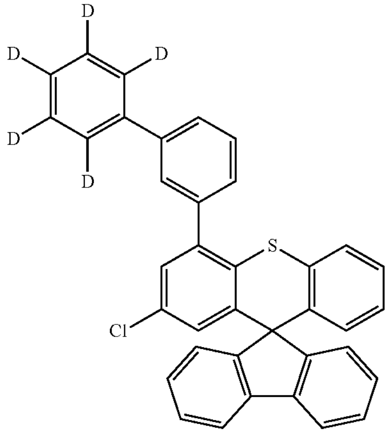
Sub 1-46
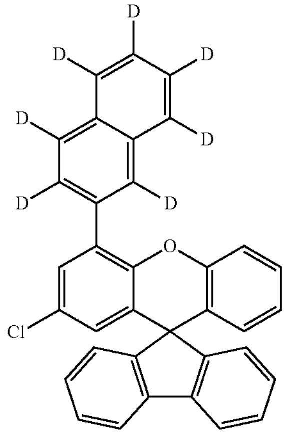
Sub 1-47
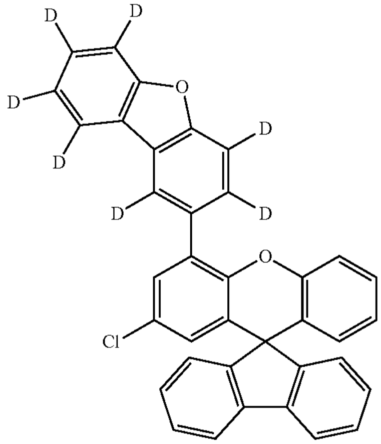
Sub 1-48
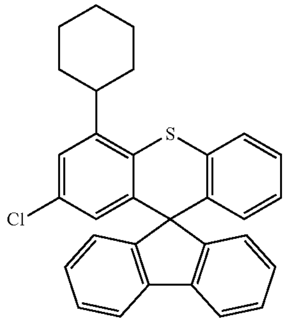

-continued
Sub 1-49
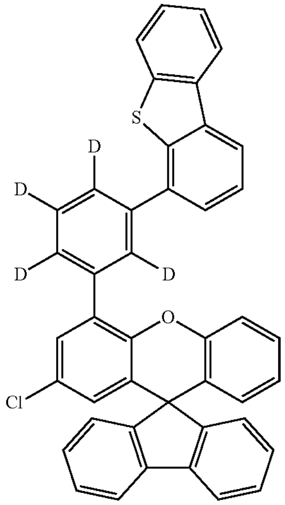
Sub 1-50
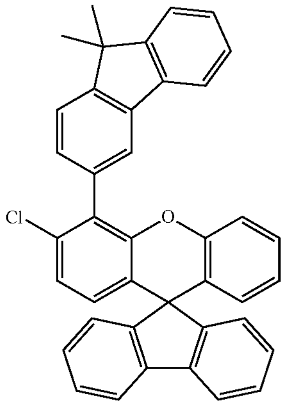
Sub 1-51
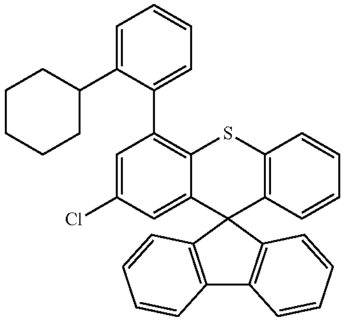
-continued
Sub 1-52
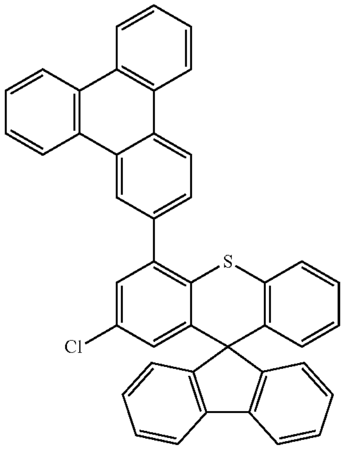
Sub 1-53
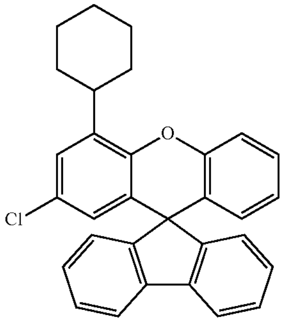
Sub 1-54
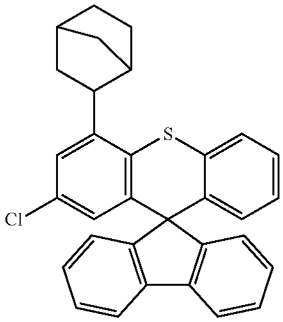
Sub 1-55
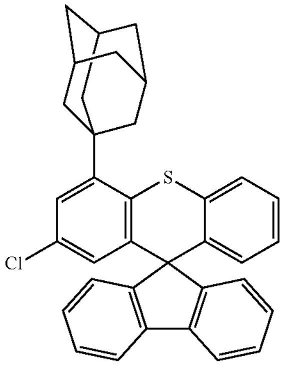

-continued
Sub 1-56
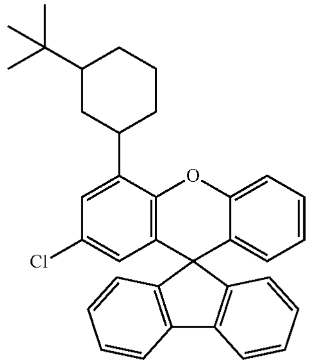
Sub 1-57
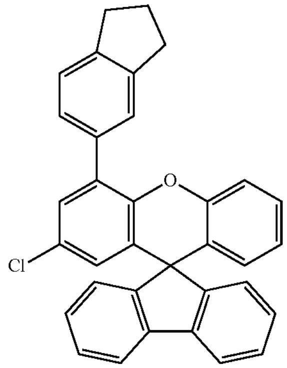
Sub 1-58
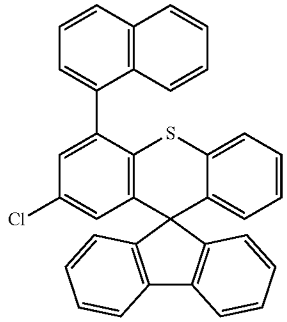
Sub 1-59
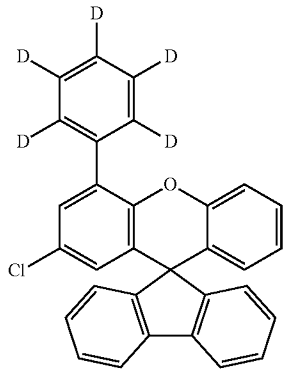
-continued
Sub 1-60
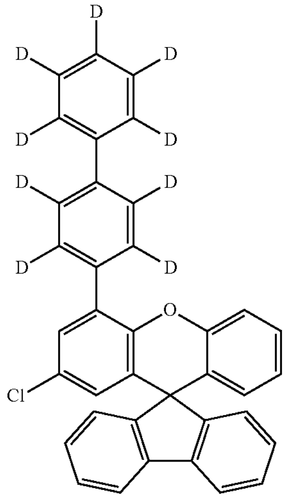
Sub 1-61
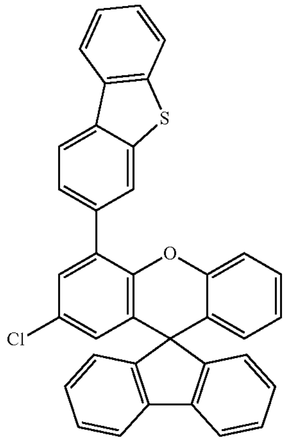
Sub 1-62
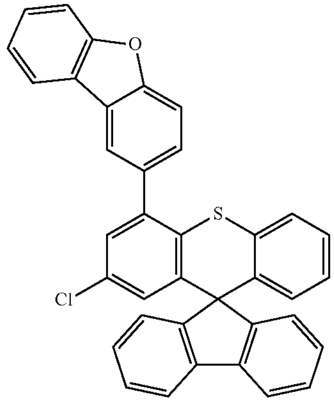

-continued
Sub 1-63
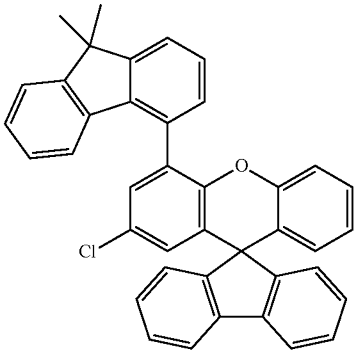
Sub 1-64
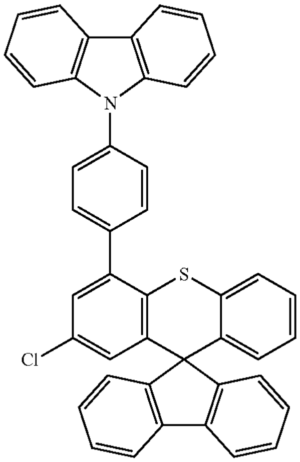
Sub 1-65
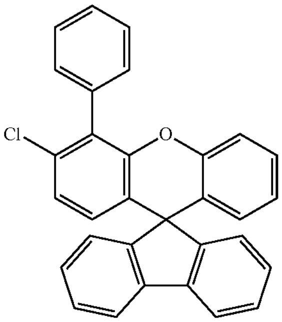
-continued
Sub 1-66
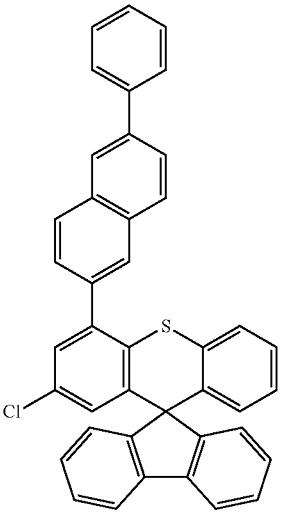
Sub 1-67
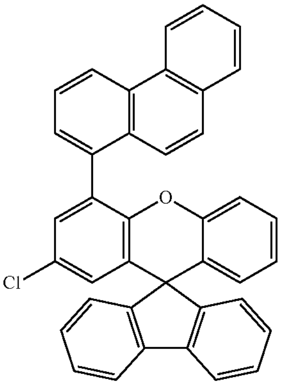
Sub 1-68
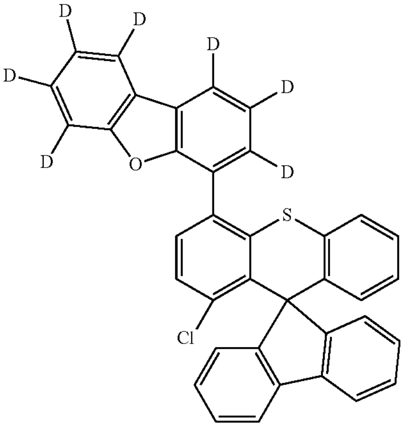

-continued

Sub 1-69

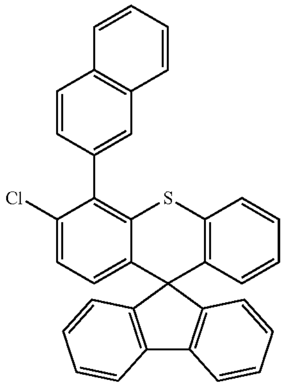

Sub 1-70

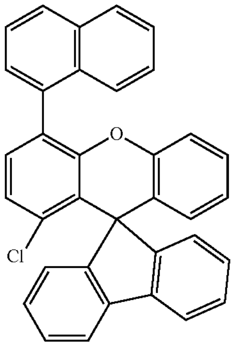

Sub 1-71

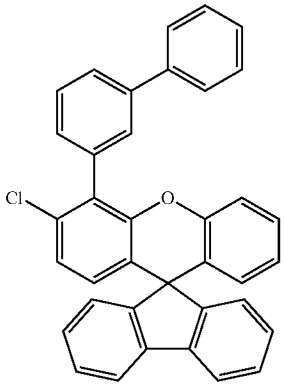

Sub 1-72

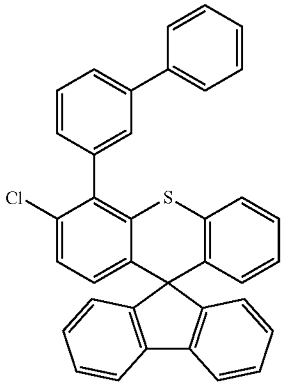

TABLE 1

| compound | FD-MS |
|---|---|
| Sub 1-1 | m/z = 500.19($C_{35}H_{29}ClO$ = 501.07) |
| Sub 1-2 | m/z = 592.20($C_{41}H_{33}ClS$ = 593.22) |
| Sub 1-3 | m/z = 536.19($C_{38}H_{29}ClO$ = 537.10) |
| Sub 1-4 | m/z = 482.14($C_{34}H_{23}ClO$ = 483.01) |
| Sub 1-5 | m/z = 482.14($C_{34}H_{23}ClO$ = 483.01) |
| Sub 1-6 | m/z = 512.14($C_{35}H_{25}ClS$ = 513.10) |
| Sub 1-7 | m/z = 460.16($C_{32}H_{25}ClO$ = 461.00) |
| Sub 1-8 | m/z = 448.16($C_{31}H_{25}ClO$ = 448.99) |
| Sub 1-9 | m/z = 496.16($C_{35}H_{25}ClO$ = 497.03) |
| Sub 1-10 | m/z = 540.17($C_{37}H_{29}ClS$ = 541.15) |
| Sub 1-11 | m/z = 592.20($C_{41}H_{33}ClS$ = 593.22) |
| Sub 1-12 | m/z = 524.19($C_{37}H_{29}ClO$ = 525.09) |
| Sub 1-13 | m/z = 576.22($C_{41}H_{33}ClO$ = 577.16) |
| Sub 1-14 | m/z = 536.19($C_{38}H_{29}ClO$ = 537.10) |
| Sub 1-15 | m/z = 482.14($C_{34}H_{23}ClO$ = 483.01) |
| Sub 1-16 | m/z = 534.12($C_{37}H_{23}ClS$ = 535.10) |
| Sub 1-17 | m/z = 492.13($C_{35}H_{21}ClO$ = 493.00) |
| Sub 1-18 | m/z = 518.14($C_{37}H_{23}ClO$ = 519.04) |
| Sub 1-19 | m/z = 459.08($C_{30}H_{18}ClNS$ = 459.99) |
| Sub 1-20 | m/z = 442.11($C_{31}H_{19}ClO$ = 442.94) |
| Sub 1-21 | m/z = 458.09($C_{31}H_{19}ClS$ = 459.00) |
| Sub 1-22 | m/z = 534.12($C_{37}H_{23}ClS$ = 535.10) |
| Sub 1-23 | m/z = 568.16($C_{41}H_{25}ClO$ = 569.10) |
| Sub 1-24 | m/z = 492.13($C_{35}H_{21}ClO$ = 493.00) |
| Sub 1-25 | m/z = 542.14($C_{39}H_{23}ClO$ = 543.06) |
| Sub 1-26 | m/z = 584.14($C_{41}H_{25}ClS$ = 585.16) |
| Sub 1-27 | m/z = 568.16($C_{41}H_{25}ClO$ = 569.10) |
| Sub 1-28 | m/z = 540.17($C_{37}H_{29}ClS$ = 541.15) |
| Sub 1-29 | m/z = 548.10($C_{37}H_{21}ClOS$ = 549.08) |
| Sub 1-30 | m/z = 548.10($C_{37}H_{21}ClOS$ = 549.08) |
| Sub 1-31 | m/z = 532.12($C_{37}H_{21}ClO_2$ = 533.02) |
| Sub 1-32 | m/z = 532.12($C_{37}H_{21}ClO_2$ = 533.02) |
| Sub 1-33 | m/z = 564.08($C_{37}H_{21}ClS_2$ = 565.14) |
| Sub 1-34 | m/z = 548.10($C_{37}H_{21}ClOS$ = 549.08) |
| Sub 1-35 | m/z = 559.13($C_{38}H_{22}ClNO_2$ = 560.05) |
| Sub 1-36 | m/z = 575.11($C_{38}H_{22}ClNOS$ = 576.11) |
| Sub 1-37 | m/z = 574.15($C_{40}H_{27}ClS$ = 575.17) |
| Sub 1-38 | m/z = 558.18($C_{40}H_{27}ClO$ = 559.11) |
| Sub 1-39 | m/z = 574.15($C_{40}H_{27}ClS$ = 575.17) |
| Sub 1-40 | m/z = 624.13($C_{43}H_{25}ClOS$ = 625.18) |
| Sub 1-41 | m/z = 624.13($C_{43}H_{25}ClOS$ = 625.18) |
| Sub 1-42 | m/z = 568.16($C_{41}H_{25}ClO$ = 569.10) |
| Sub 1-43 | m/z = 498.18($C_{35}H_{27}ClO$ = 499.05) |
| Sub 1-44 | m/z = 463.12($C_{31}H_{14}D_5ClS$ = 464.03) |
| Sub 1-45 | m/z = 539.15($C_{37}H_{18}D_5ClS$ = 540.13) |
| Sub 1-46 | m/z = 499.17($C_{35}H_{14}D_7ClO$ = 500.04) |
| Sub 1-47 | m/z = 539.17($C_{37}H_{14}D_7ClO_2$ = 540.07) |
| Sub 1-48 | m/z = 464.14($C_{31}H_{25}ClS$ = 465.05) |
| Sub 1-49 | m/z = 628.16($C_{43}H_{21}D_4ClOS$ = 629.21) |
| Sub 1-50 | m/z = 558.18($C_{40}H_{27}ClO$ = 559.11) |
| Sub 1-51 | m/z = 540.17($C_{37}H_{29}ClS$ = 541.15) |
| Sub 1-52 | m/z = 608.14($C_{43}H_{25}ClS$ = 609.18) |
| Sub 1-53 | m/z = 448.16($C_{31}H_{25}ClO$ = 448.99) |
| Sub 1-54 | m/z = 476.14($C_{32}H_{25}ClS$ = 477.06) |
| Sub 1-55 | m/z = 516.17($C_{35}H_{29}ClS$ = 517.13) |
| Sub 1-56 | m/z = 504.22($C_{35}H_{33}ClO$ = 505.10) |
| Sub 1-57 | m/z = 482.14($C_{34}H_{23}ClO$ = 483.01) |
| Sub 1-58 | m/z = 508.11($C_{35}H_{21}ClS$ = 509.06) |
| Sub 1-59 | m/z = 447.14($C_{31}H_{14}D_5ClO$ = 447.97) |
| Sub 1-60 | m/z = 527.20($C_{37}H_{14}D_9ClO$ = 528.09) |
| Sub 1-61 | m/z = 548.10($C_{37}H_{21}ClOS$ = 549.08) |
| Sub 1-62 | m/z = 548.10($C_{37}H_{21}ClOS$ = 549.08) |
| Sub 1-63 | m/z = 558.18($C_{40}H_{27}ClO$ = 559.11) |
| Sub 1-64 | m/z = 623.15($C_{43}H_{26}ClNS$ = 624.20) |
| Sub 1-65 | m/z = 442.11($C_{31}H_{19}ClO$ = 442.94) |
| Sub 1-66 | m/z = 584.14($C_{41}H_{25}ClS$ = 585.16) |
| Sub 1-67 | m/z = 542.14($C_{39}H_{23}ClO$ = 543.06) |
| Sub 1-68 | m/z = 555.14($C_{37}H_{14}D_7ClOS$ = 556.13) |
| Sub 1-69 | m/z = 508.11($C_{35}H_{21}ClS$ = 509.06) |
| Sub 1-70 | m/z = 492.13($C_{35}H_{21}ClO$ = 493.00) |
| Sub 1-71 | m/z = 518.14($C_{37}H_{23}ClO$ = 519.04) |
| Sub 1-72 | m/z = 534.12($C_{37}H_{23}ClS$ = 535.10) |

II. Synthesis of Sub 2

Sub 2 of Reaction Scheme 1 may be synthesized by the reaction route of Scheme 2, but is not limited thereto.

<Reaction Scheme 2>

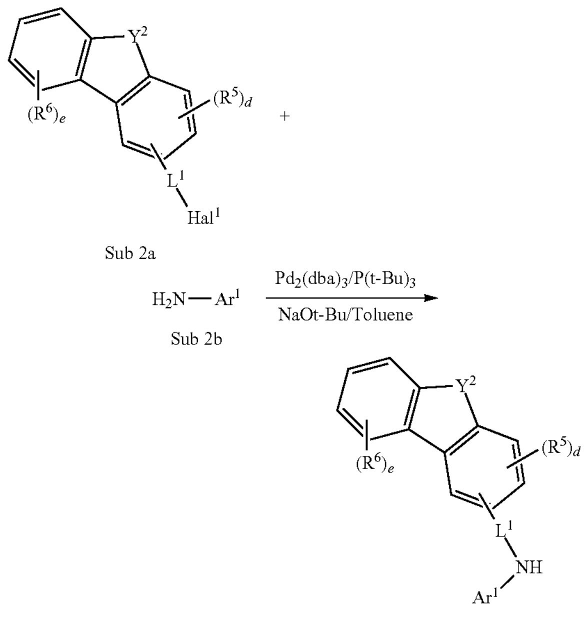

Sub 2a

Sub 2b

Sub 2

(Hal$^1$ is Br or Cl)

Synthesis examples of specific compounds belonging to Sub 2 are as follows.

1. Synthesis Example of Sub 2-1

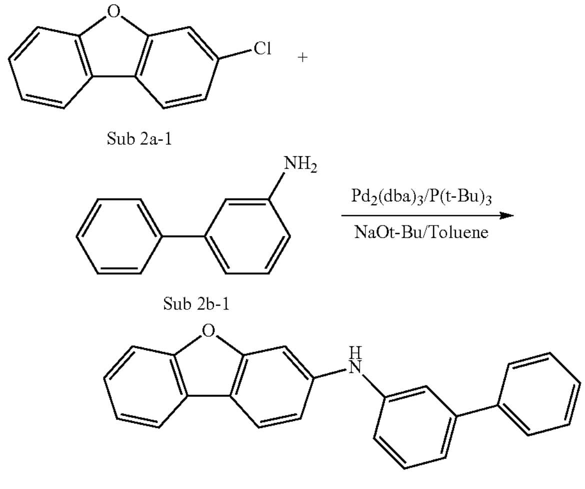

Sub 2a-1

Sub 2b-1

Sub 2-1

Sub 2b-1 (10.0 g, 59.2 mmol), $Pd_2(dba)_3$ (1.6 g, 1.8 mmol), NaOt-Bu (17.1 g, 177.7 mmol), 50 wt % $P(t-Bu)_3$ (1.4 ml, 3.6 mmol), Toluene (250 ml) were added to Sub 2a-1 (12.0 g, 59.2 mmol) and stirred at 100° C. When the reaction is complete, the mixture was extracted with $CH_2Cl_2$ and water, the organic layer was dried over $MgSO_4$, concentrated, and the resulting compound was recrystallized by silicagel column to obtain 17.6 g (yield: 89%) of the product.

2. Synthesis example of Sub 2-29

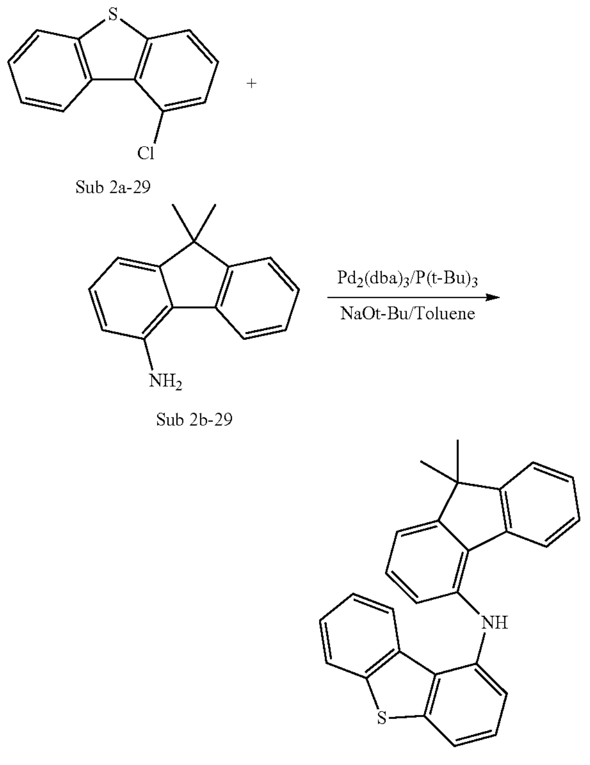

Sub 2a-29

Sub 2b-29

Sub 2-29

Sub 2b-29 (9.6 g, 45.7 mmol), $Pd_2(dba)_3$ (1.3 g, 1.4 mmol), NaOt-Bu (13.2 g, 137.2 mmol), 50 wt % $P(t-Bu)_3$ (1.1 ml, 2.7 mmol), Toluene (230 ml) were added to Sub 2a-29 (10.0 g, 45.7 mmol) and 15.2 g (yield: 85%) of the product was obtained by using the synthesis method of Sub 2-1.

3. Synthesis Example of Sub 2-72

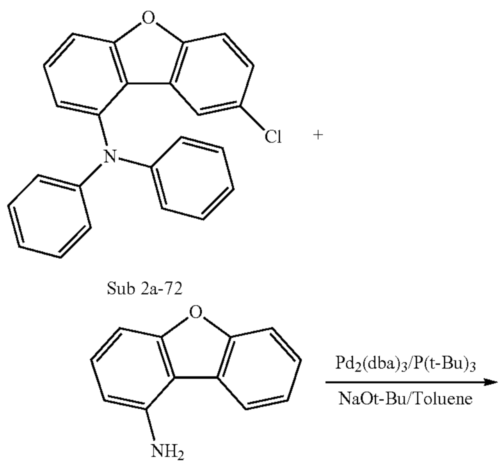

Sub 2a-72

Sub 2b-72

-continued

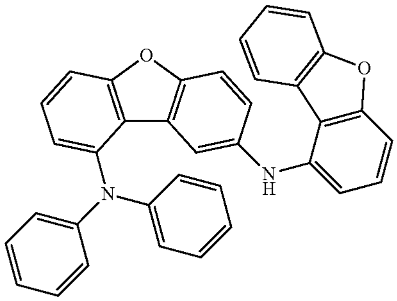

Sub 2-72

Sub 2b-72 (5.0 g, 27.0 mmol), $Pd_2(dba)_3$ (0.7 g, 0.8 mmol), NaOt-Bu (7.8 g, 81.1 mmol), 50 wt % $P(t\text{-}Bu)_3$ (0.66 ml, 1.6 mmol), Toluene (230 ml) were added to Sub 2a-72 (10.0 g, 27.0 mmol) and 12.1 g (yield: 87%) of the product was obtained by using the synthesis method of Sub 2-1.

Meanwhile, the compound belonging to Sub 2 may be the following compounds, but is not limited thereto, and Table 2 shows FD-MS values of the compounds belonging to Sub 2.

Sub 2-1

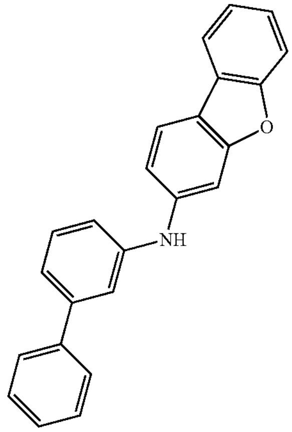

Sub 2-2

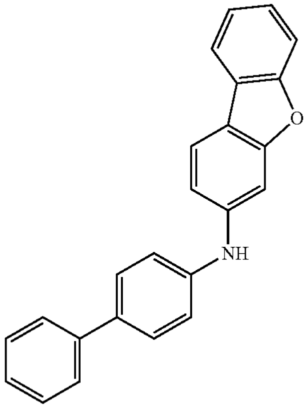

-continued

Sub 2-3

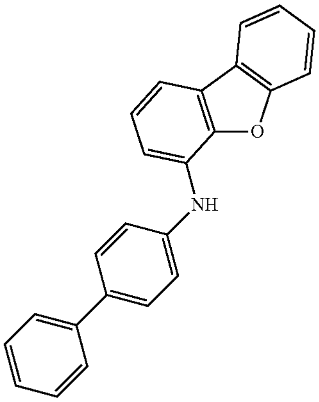

Sub 2-4

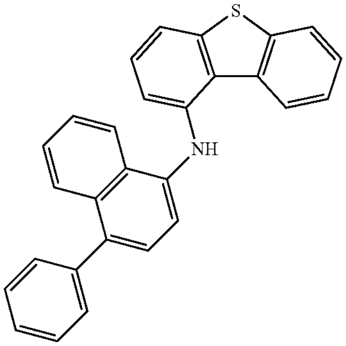

Sub 2-5

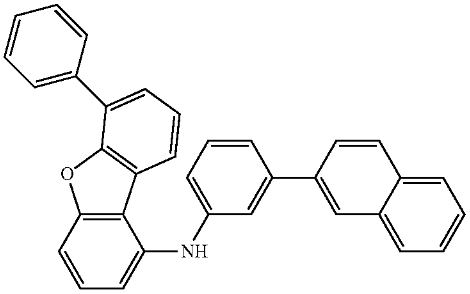

Sub 2-6

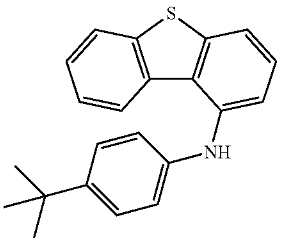

-continued
Sub 2-7
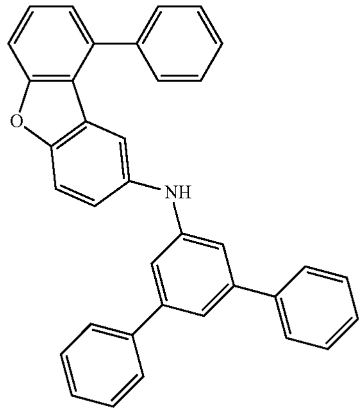
Sub 2-8
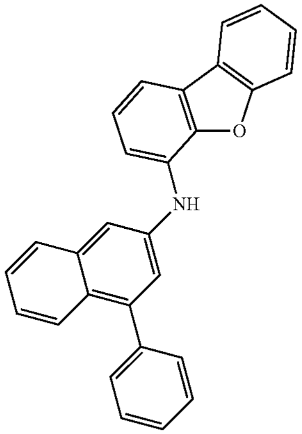
Sub 2-9
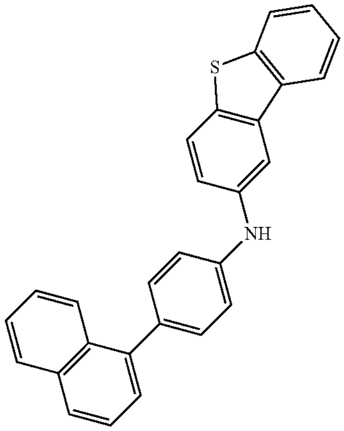
Sub 2-10
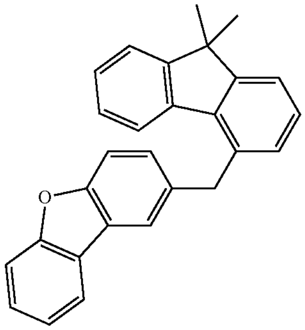
-continued
Sub 2-11
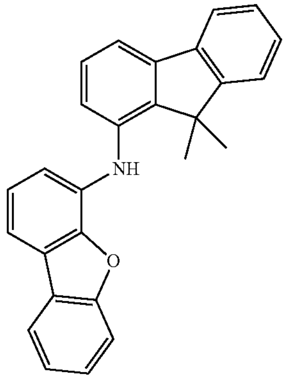
Sub 2-12
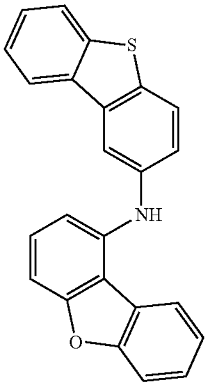
Sub 2-13
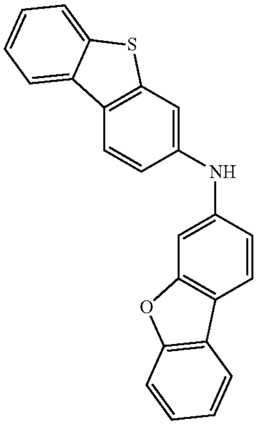
Sub 2-14
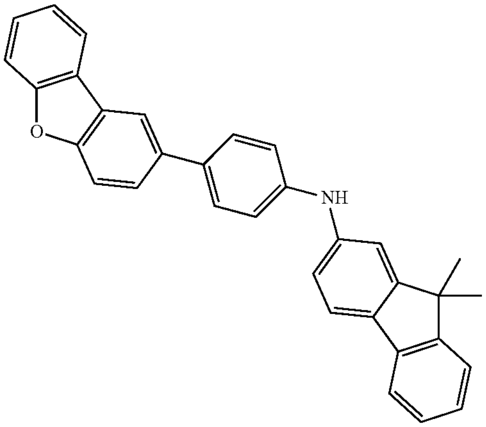

-continued
Sub 2-15
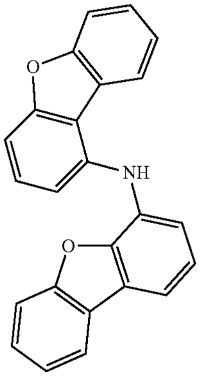
Sub 2-16
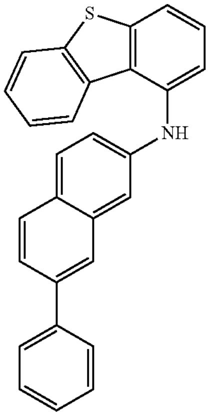
Sub 2-17
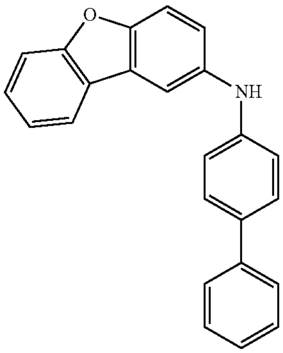
Sub 2-18
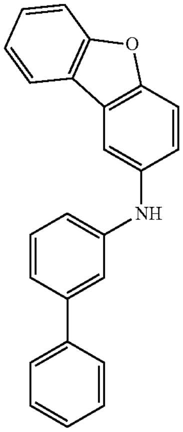
-continued
Sub 2-19
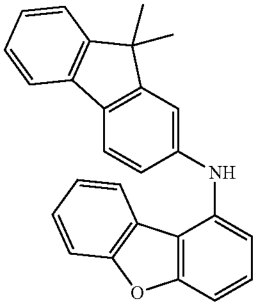
Sub 2-20
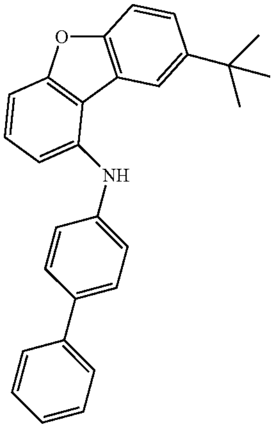
Sub 2-21
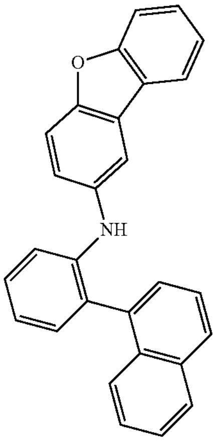
Sub 2-22
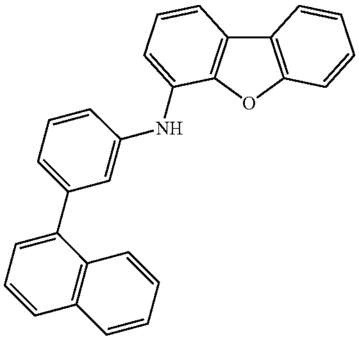

-continued
Sub 2-23
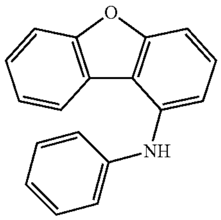
Sub 2-24
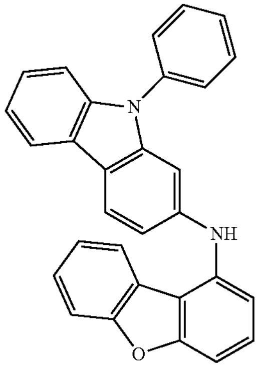
Sub 2-25
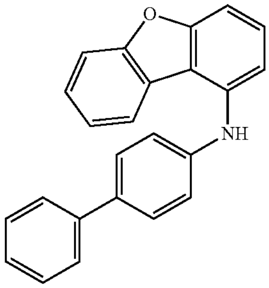
Sub 2-26
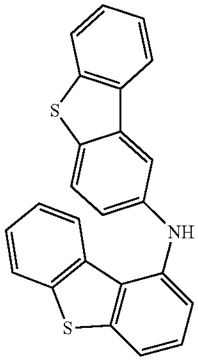
Sub 2-27
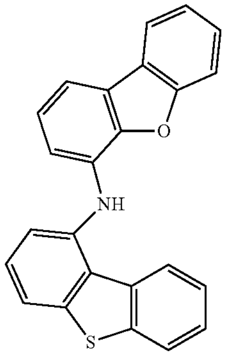
-continued
Sub 2-28
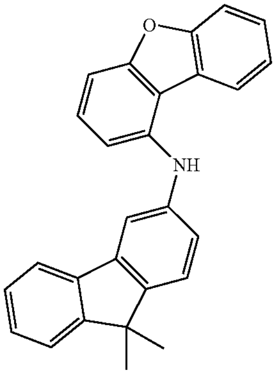
Sub 2-29
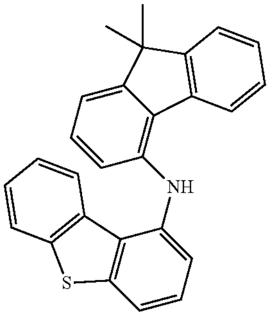
Sub 2-30
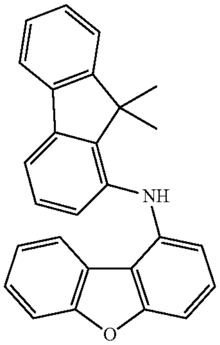
Sub 2-31
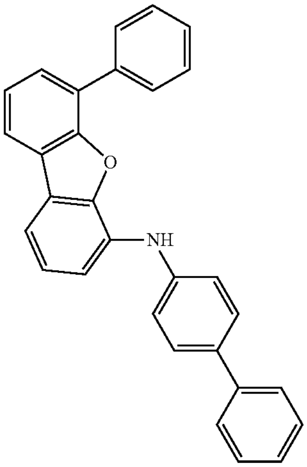

-continued
Sub 2-32
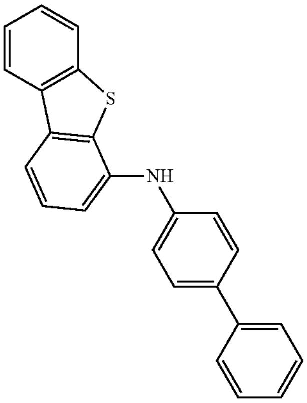
Sub 2-33
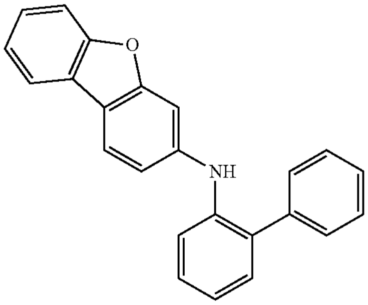
Sub 2-34
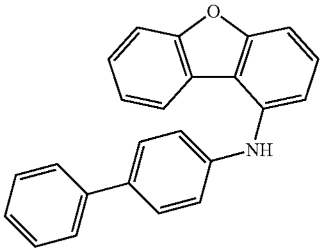
Sub 2-35
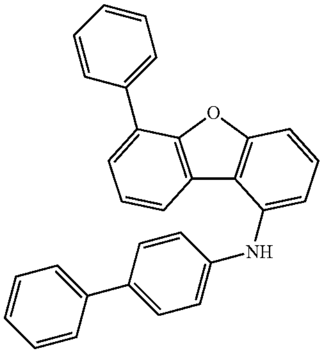
-continued
Sub 2-36
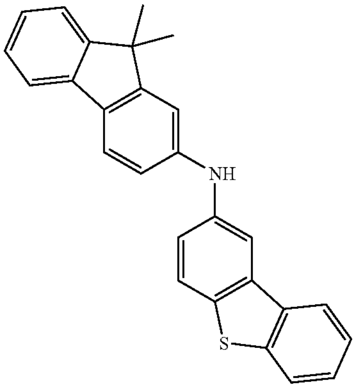
Sub 2-37
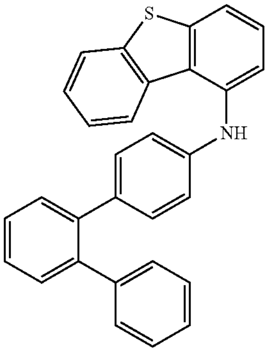
Sub 2-38
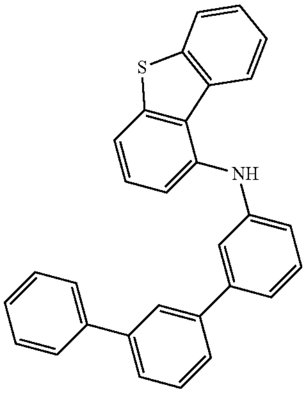
Sub 2-39
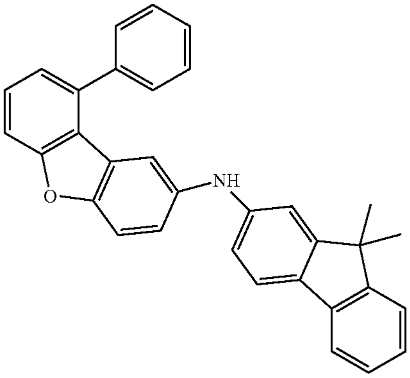

-continued
Sub 2-40
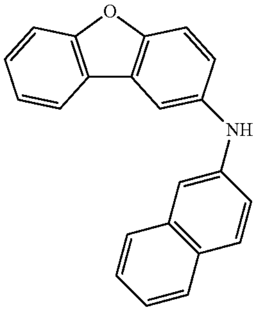
Sub 2-41
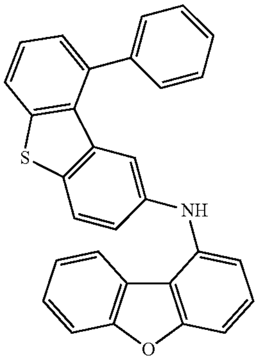
Sub 2-42
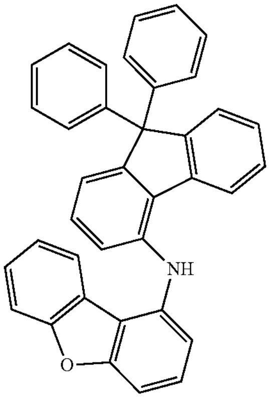
Sub 2-43
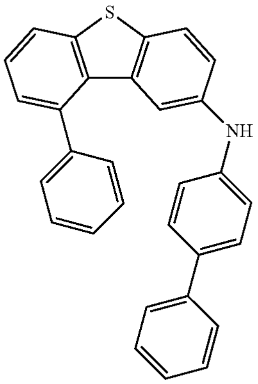
-continued
Sub 2-44
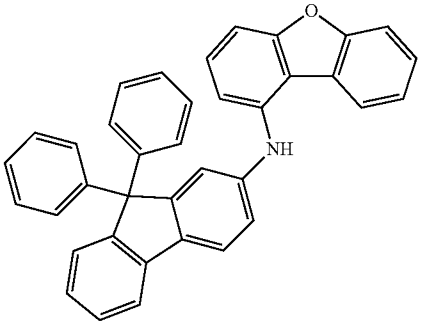
Sub 2-45
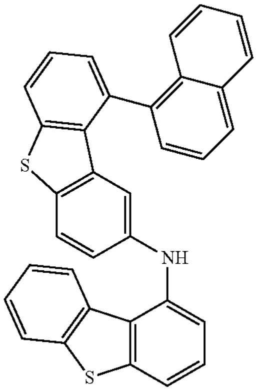
Sub 2-46
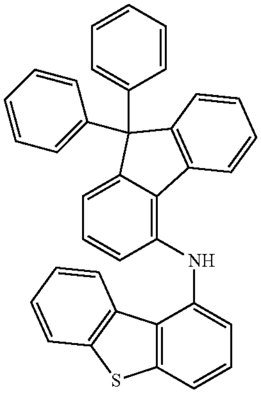
Sub 2-47
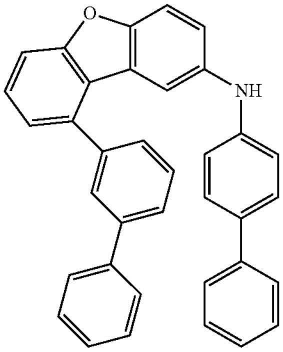

-continued
Sub 2-48
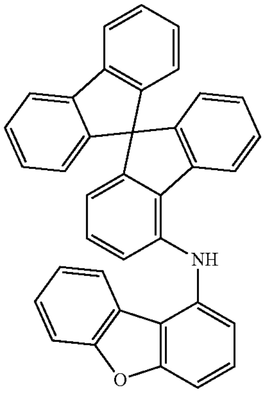
Sub 2-49
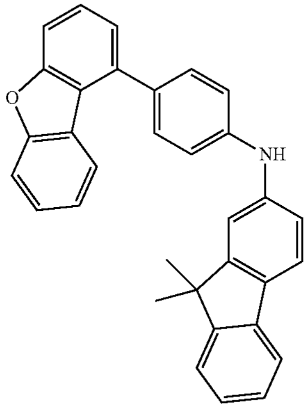
Sub 2-50
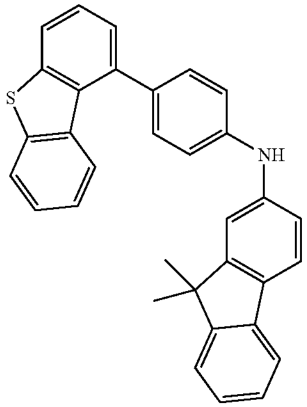
Sub 2-51
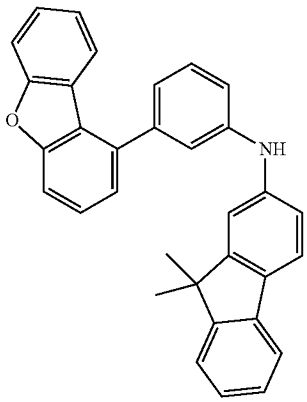
-continued
Sub 2-52
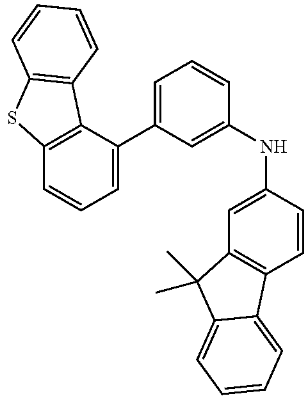
Sub 2-53
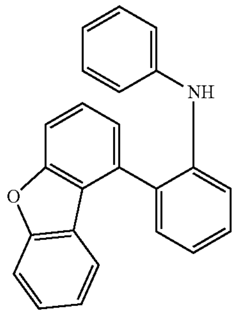
Sub 2-54
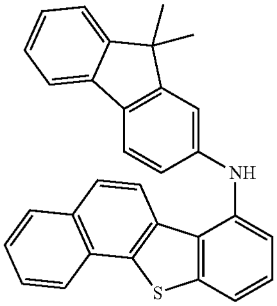
Sub 2-55
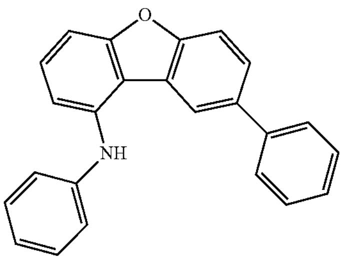

-continued
Sub 2-56
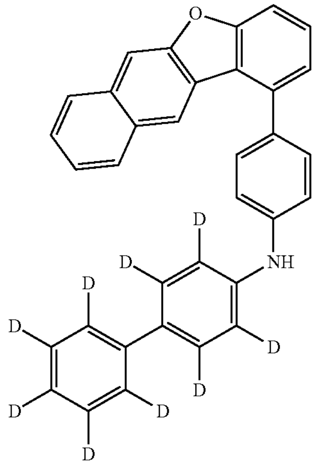
Sub 2-57
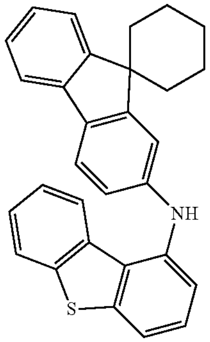
Sub 2-58
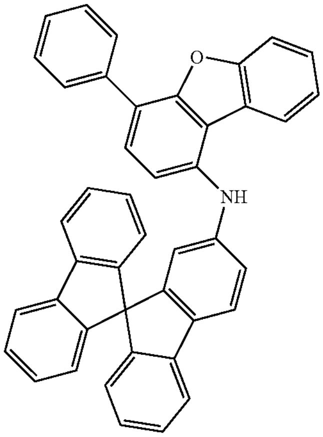
Sub 2-59
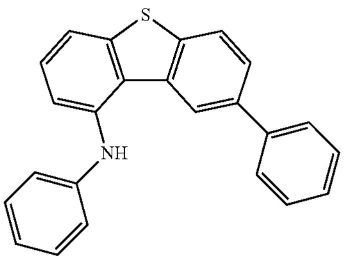
-continued
Sub 2-60
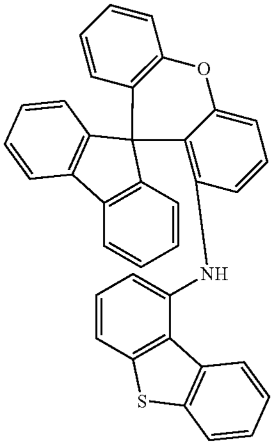
Sub 2-61
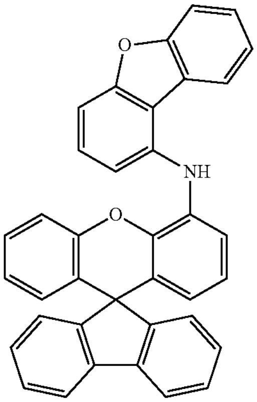
Sub 2-62
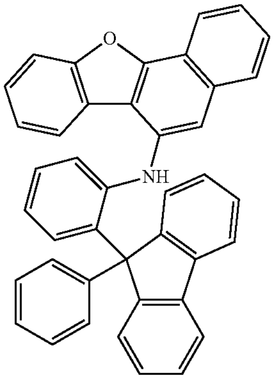
Sub 2-63
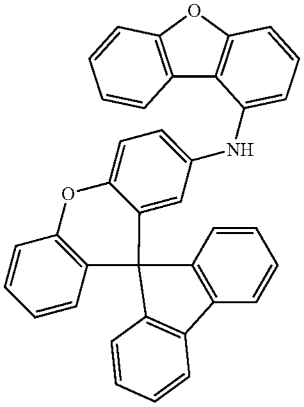

-continued
Sub 2-64
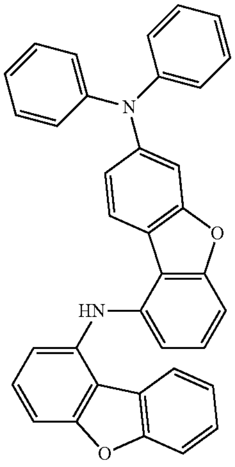
Sub 2-65
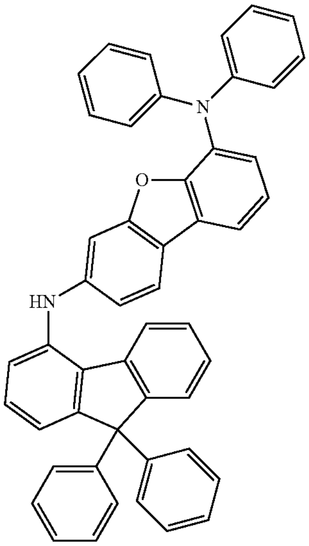
Sub 2-66
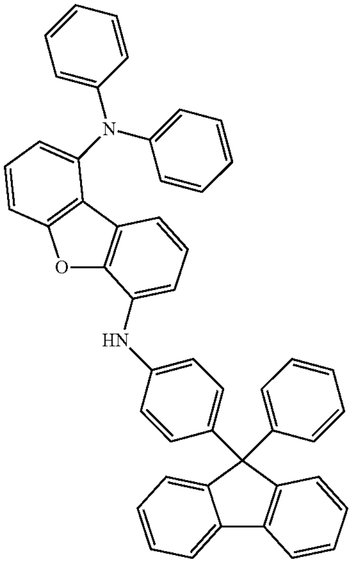
-continued
Sub 2-67
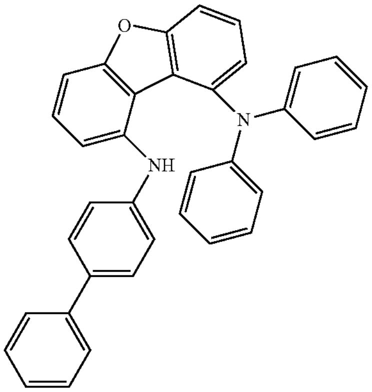
Sub 2-68
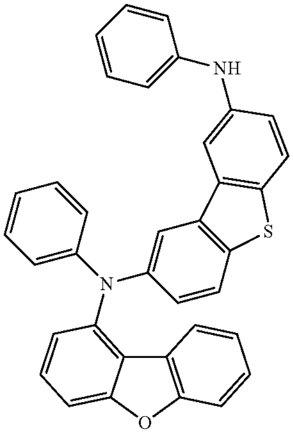
Sub 2-69
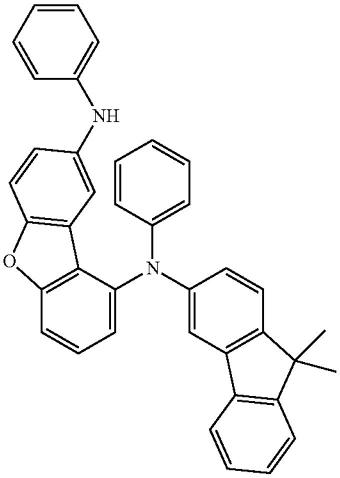

-continued
Sub 2-70
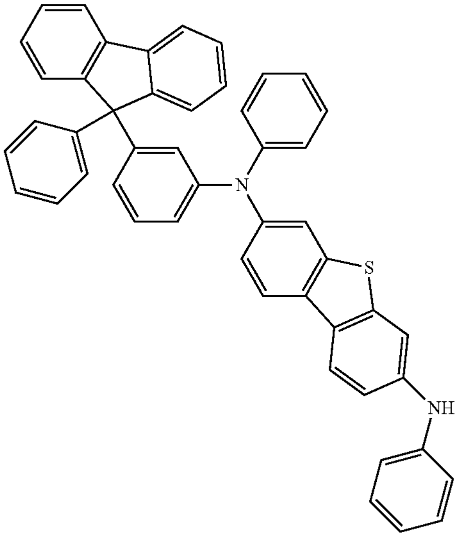
Sub 2-71
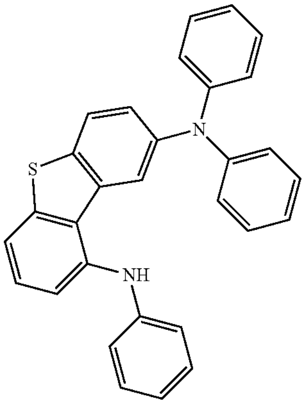
Sub 2-72
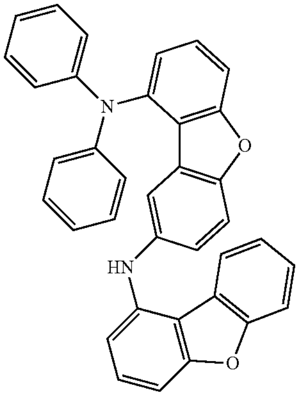
-continued
Sub 2-73
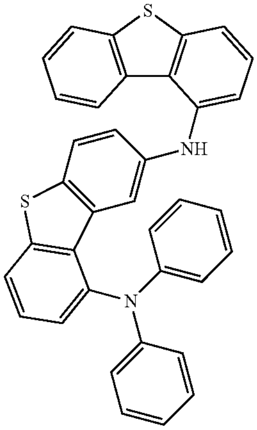
Sub 2-74
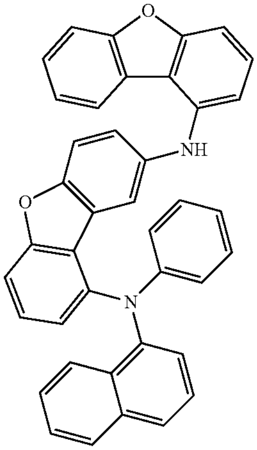
Sub 2-75
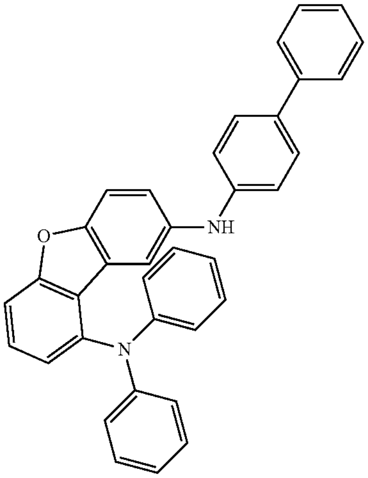

-continued
Sub 2-76
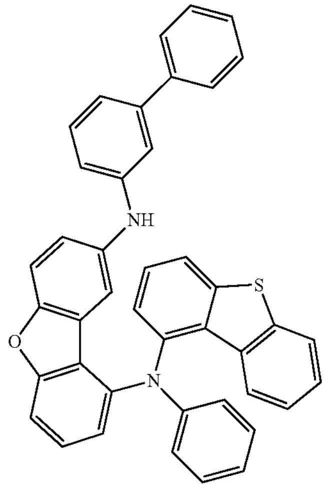
Sub 2-77
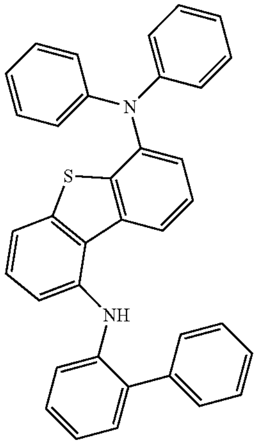
Sub 2-78
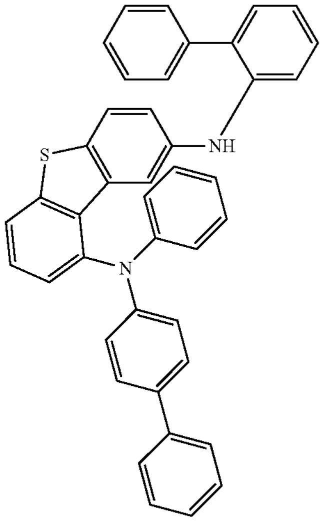
-continued
Sub 2-79
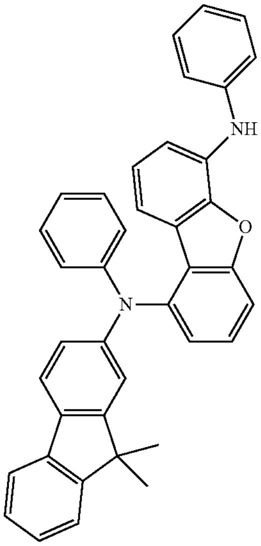
Sub 2-80
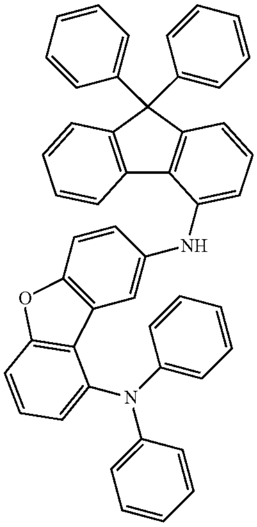
Sub 2-81
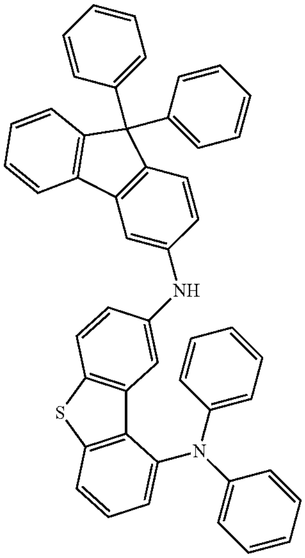

-continued
Sub 2-82
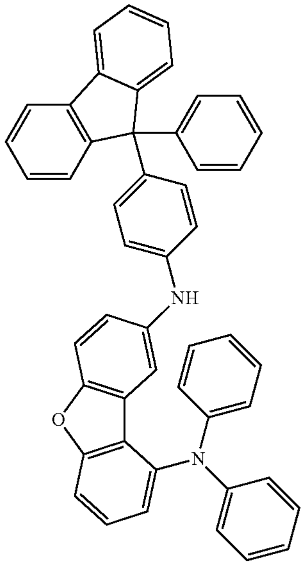
Sub 2-83
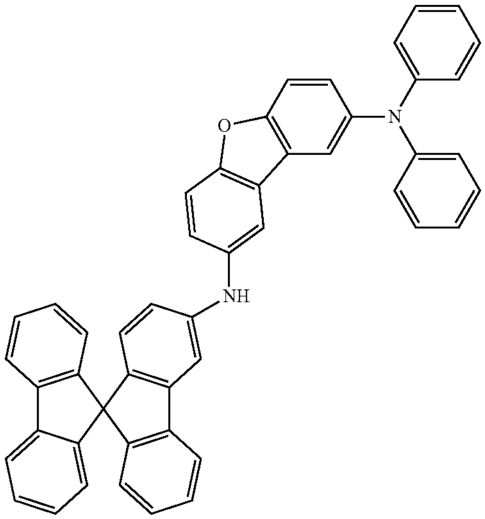
Sub 2-84
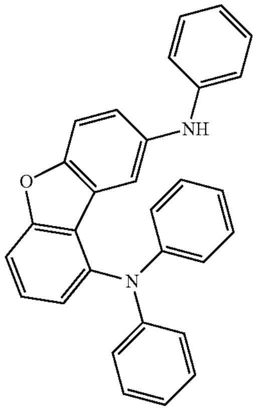
-continued
Sub 2-85
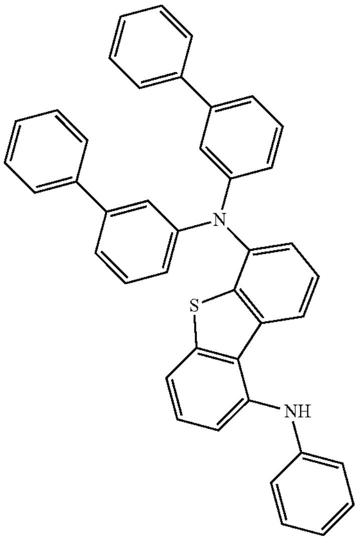
Sub 2-86
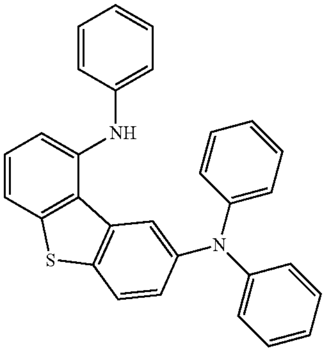
Sub 2-87
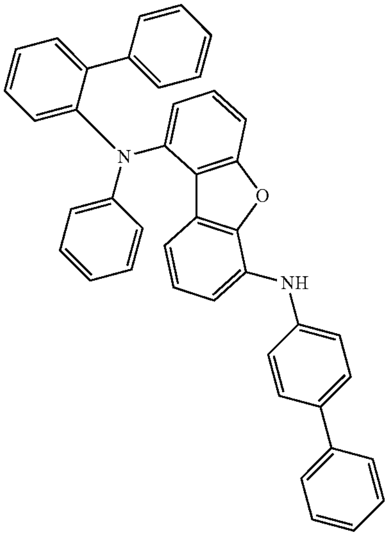

-continued
Sub 2-88
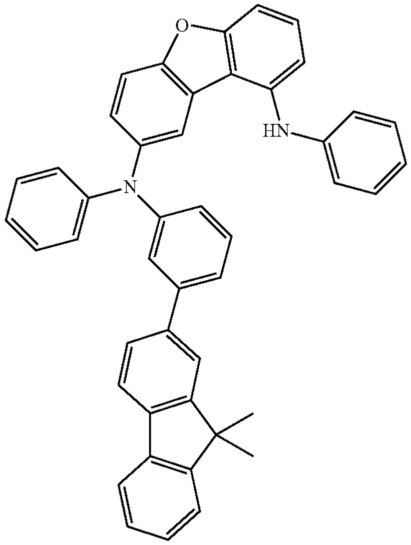
Sub 2-89
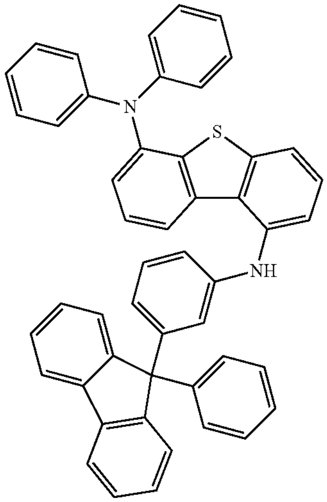
Sub 2-90
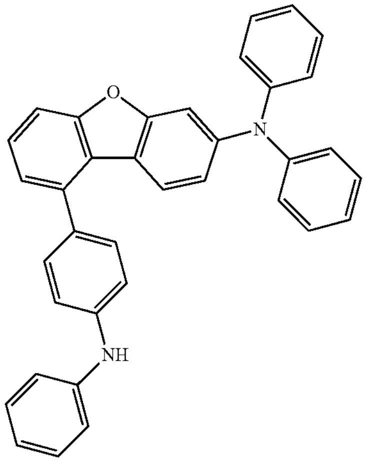
-continued
Sub 2-91
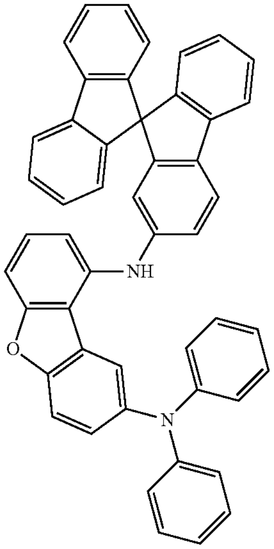
Sub 2-92
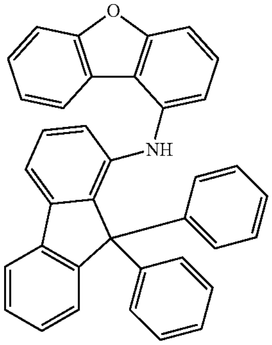
Sub 2-93
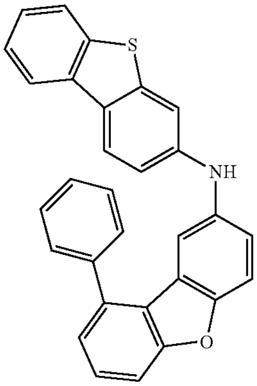
Sub 2-94
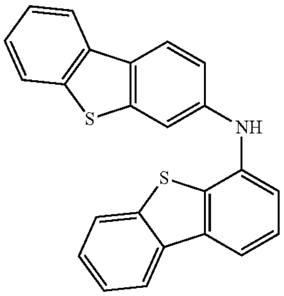

-continued
Sub 2-95
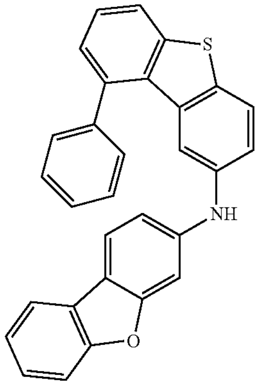
Sub 2-96
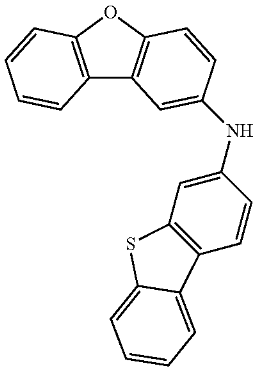
Sub 2-97
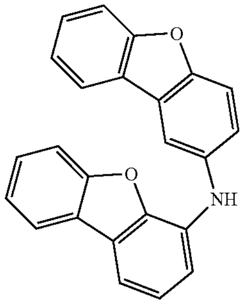
Sub 2-98
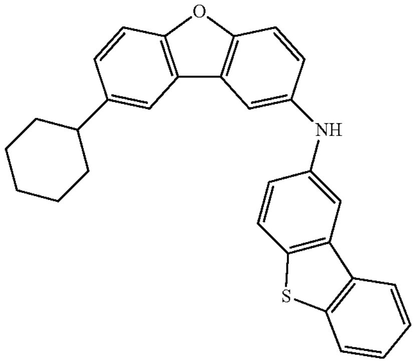
-continued
Sub 2-99
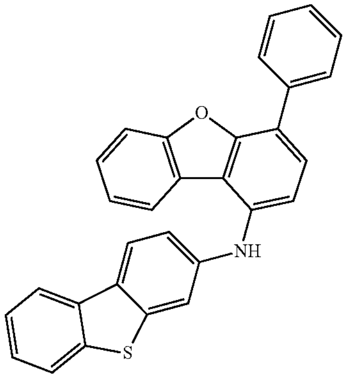
Sub 2-100
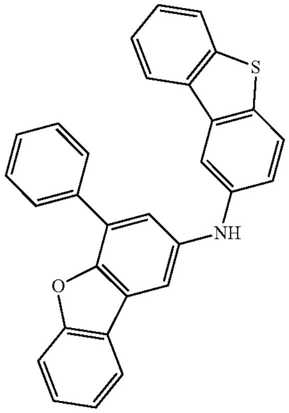
Sub 2-101
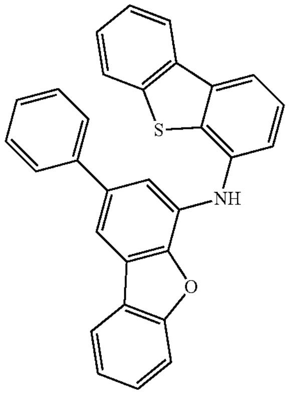
Sub 2-102
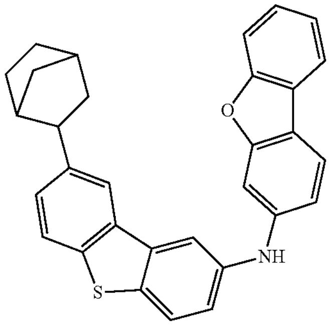

TABLE 2

| compound | FD-MS |
|---|---|
| Sub 2-1 | m/z = 335.13($C_{24}H_{17}NO$ = 335.41) |
| Sub 2-2 | m/z = 335.13($C_{24}H_{17}NO$ = 335.41) |
| Sub 2-3 | m/z = 335.13($C_{24}H_{17}NO$ = 335.41) |
| Sub 2-4 | m/z = 401.12($C_{28}H_{19}NS$ = 401.53) |
| Sub 2-5 | m/z = 461.18($C_{34}H_{23}NO$ = 461.56) |
| Sub 2-6 | m/z = 331.14($C_{22}H_{21}NS$ = 331.48) |
| Sub 2-7 | m/z = 487.19($C_{36}H_{25}NO$ = 487.60) |
| Sub 2-8 | m/z = 385.15($C_{28}H_{19}NO$ = 385.47) |
| Sub 2-9 | m/z = 401.12($C_{28}H_{19}NS$ = 401.53) |
| Sub 2-10 | m/z = 375.16($C_{27}H_{21}NO$ = 375.47) |
| Sub 2-11 | m/z = 375.16($C_{27}H_{21}NO$ = 375.47) |
| Sub 2-12 | m/z = 365.09($C_{24}H_{15}NOS$ = 365.45) |
| Sub 2-13 | m/z = 365.09($C_{24}H_{15}NOS$ = 365.45) |
| Sub 2-14 | m/z = 451.19($C_{33}H_{25}NO$ = 451.57) |
| Sub 2-15 | m/z = 349.11($C_{24}H_{15}NO_2$ = 349.39) |
| Sub 2-16 | m/z = 401.12($C_{28}H_{19}NS$ = 401.53) |
| Sub 2-17 | m/z = 335.13($C_{24}H_{17}NO$ = 335.41) |
| Sub 2-18 | m/z = 335.13($C_{24}H_{17}NO$ = 335.41) |
| Sub 2-19 | m/z = 375.16($C_{27}H_{21}NO$ = 375.47) |
| Sub 2-20 | m/z = 391.19($C_{28}H_{25}NO$ = 391.51) |
| Sub 2-21 | m/z = 385.15($C_{28}H_{19}NO$ = 385.47) |
| Sub 2-22 | m/z = 385.15($C_{28}H_{19}NO$ = 385.47) |
| Sub 2-23 | m/z = 259.10($C_{18}H_{13}NO$ = 259.31) |
| Sub 2-24 | m/z = 424.16($C_{30}H_{20}N_2O$ = 424.5) |
| Sub 2-25 | m/z = 335.13($C_{24}H_{17}NO$ = 335.41) |
| Sub 2-26 | m/z = 381.06($C_{24}H_{15}NS_2$= 381.51) |
| Sub 2-27 | m/z = 365.09($C_{24}H_{15}NOS$ = 365.45) |
| Sub 2-28 | m/z = 375.16($C_{27}H_{21}NO$ = 375.47) |
| Sub 2-29 | m/z = 391.14($C_{27}H_{21}NS$ = 391.53) |
| Sub 2-30 | m/z = 375.16($C_{27}H_{21}NO$ = 375.47) |
| Sub 2-31 | m/z = 411.16($C_{30}H_{21}NO$ = 411.50) |
| Sub 2-32 | m/z = 351.11($C_{24}H_{17}NS$ = 351.47) |
| Sub 2-33 | m/z = 335.13($C_{24}H_{17}NO$ = 335.41) |
| Sub 2-34 | m/z = 335.13($C_{24}H_{17}NO$ = 335.41) |
| Sub 2-35 | m/z = 411.16($C_{30}H_{21}NO$ = 411.50) |
| Sub 2-36 | m/z = 391.14($C_{27}H_{21}NS$ = 391.53) |
| Sub 2-37 | m/z = 427.14($C_{30}H_{21}NS$ = 427.56) |
| Sub 2-38 | m/z = 427.14($C_{30}H_{21}NS$ = 427.56) |
| Sub 2-39 | m/z = 451.19($C_{33}H_{25}NO$ = 451.57) |
| Sub 2-40 | m/z = 309.12($C_{22}H_{15}NO$ = 309.37) |
| Sub 2-41 | m/z = 441.12($C_{30}H_{19}NOS$ = 441.55) |
| Sub 2-42 | m/z = 499.19($C_{37}H_{25}NO$ = 499.61) |
| Sub 2-43 | m/z = 427.14($C_{30}H_{21}NS$ = 427.56) |
| Sub 2-44 | m/z = 499.19($C_{37}H_{25}NO$ = 499.61) |
| Sub 2-45 | m/z = 507.11($C_{34}H_{21}NS_2$= 507.67) |
| Sub 2-46 | m/z = 515.17($C_{37}H_{25}NS$ = 515.67) |
| Sub 2-47 | m/z = 487.19($C_{36}H_{25}NO$ = 487.60) |
| Sub 2-48 | m/z = 497.18($C_{37}H_{23}NO$ = 497.60) |
| Sub 2-49 | m/z = 451.19($C_{33}H_{25}NO$ = 451.57) |
| Sub 2-50 | m/z = 467.17($C_{33}H_{25}NS$ = 467.63) |
| Sub 2-51 | m/z = 451.19($C_{33}H_{25}NO$ = 451.57) |
| Sub 2-52 | m/z = 467.17($C_{33}H_{25}NS$ = 467.63) |
| Sub 2-53 | m/z = 335.13($C_{24}H_{17}NO$ = 335.41) |
| Sub 2-54 | m/z = 441.16($C_{31}H_{23}NS$ = 441.59) |
| Sub 2-55 | m/z = 335.13($C_{24}H_{17}NO$ = 335.41) |
| Sub 2-56 | m/z = 470.23($C_{34}H_{14}D_9NO$ = 470.62) |
| Sub 2-57 | m/z = 431.17($C_{30}H_{25}NS$ = 431.60) |
| Sub 2-58 | m/z = 573.21($C_{43}H_{27}NO$ = 573.69) |
| Sub 2-59 | m/z = 351.11($C_{24}H_{17}NS$ = 351.47) |
| Sub 2-60 | m/z = 529.15($C_{37}H_{23}NOS$ = 529.66) |
| Sub 2-61 | m/z = 513.17($C_{37}H_{23}NO_2$ = 513.60) |
| Sub 2-62 | m/z = 549.21($C_{41}H_{27}NO$ = 549.67) |
| Sub 2-63 | m/z = 513.17($C_{37}H_{23}NO_2$ = 513.60) |
| Sub 2-64 | m/z = 516.18($C_{36}H_{24}N_2O_2$ = 516.60) |
| Sub 2-65 | m/z = 666.27($C_{49}H_{34}N_2O$ = 666.82) |
| Sub 2-66 | m/z = 666.27($C_{49}H_{34}N_2O$ = 666.82) |
| Sub 2-67 | m/z = 502.20($C_{36}H_{26}N_2O$ = 502.62) |
| Sub 2-68 | m/z = 532.16($C_{36}H_{24}N_2OS$ = 532.66) |
| Sub 2-69 | m/z = 542.24($C_{39}H_{30}N_2O$ = 542.68) |
| Sub 2-70 | m/z = 682.24($C_{49}H_{34}N_2S$ = 682.88) |
| Sub 2-71 | m/z = 442.15($C_{30}H_{22}N_2S$ = 442.58) |
| Sub 2-72 | m/z = 516.18($C_{36}H_{24}N_2O_2$= 516.60) |
| Sub 2-73 | m/z = 548.14($C_{36}H_{24}N_2S_2$ = 548.72) |
| Sub 2-74 | m/z = 566.20($C_{40}H_{26}N_2O_2$= 566.66) |
| Sub 2-75 | m/z = 502.20($C_{36}H_{26}N_2O$ = 502.62) |
| Sub 2-76 | m/z = 608.19($C_{42}H_{28}N_2OS$ = 608.76) |
| Sub 2-77 | m/z = 518.18($C_{36}H_{26}N_2S$ = 518.68) |
| Sub 2-78 | m/z = 594.21($C_{42}H_{30}N_2S$ = 594.78) |

TABLE 2-continued

| compound | FD-MS |
|---|---|
| Sub 2-79 | m/z = 542.24($C_{39}H_{30}N_2O$ = 542.68) |
| Sub 2-80 | m/z = 666.27($C_{49}H_{34}N_2O$ = 666.82) |
| Sub 2-81 | m/z = 682.24($C_{49}H_{34}N_2S$ = 682.88) |
| Sub 2-82 | m/z = 666.27($C_{49}H_{34}N_2O$ = 666.82) |
| Sub 2-83 | m/z = 664.25($C_{49}H_{32}N_2O$ = 664.81) |
| Sub 2-84 | m/z = 426.17($C_{30}H_{22}N_2O$ = 426.52) |
| Sub 2-85 | m/z = 594.21($C_{42}H_{30}N_2S$ = 594.78) |
| Sub 2-86 | m/z = 442.15($C_{30}H_{22}N_2S$ = 442.58) |
| Sub 2-87 | m/z = 578.24($C_{42}H_{30}N_2O$ = 578.72) |
| Sub 2-88 | m/z = 618.27($C_{45}H_{34}N_2O$ = 618.78) |
| Sub 2-89 | m/z = 682.24($C_{49}H_{34}N_2S$ = 682.88) |
| Sub 2-90 | m/z = 502.20($C_{36}H_{26}N_2O$ = 502.62) |
| Sub 2-91 | m/z = 664.25($C_{49}H_{32}N_2O$ = 664.81) |
| Sub 2-92 | m/z = 499.19($C_{37}H_{25}NO$ = 499.61) |
| Sub 2-93 | m/z = 441.12($C_{30}H_{19}NOS$ = 441.55) |
| Sub 2-94 | m/z = 381.06($C_{24}H_{15}NS_2$ = 381.51) |
| Sub 2-95 | m/z = 441.12($C_{30}H_{19}NOS$ = 441.55) |
| Sub 2-96 | m/z = 365.09($C_{24}H_{15}NOS$ = 365.45) |
| Sub 2-97 | m/z = 349.11($C_{24}H_{15}NO_2$ = 349.39) |
| Sub 2-98 | m/z = 447.17($C_{30}H_{25}NOS$ = 447.60) |
| Sub 2-99 | m/z = 441.12($C_{30}H_{19}NOS$ = 441.55) |
| Sub 2-100 | m/z = 441.12($C_{30}H_{19}NOS$ = 441.55) |
| Sub 2-101 | m/z = 441.12($C_{30}H_{19}NOS$ = 441.55) |
| Sub 2-102 | m/z = 459.17($C_{31}H_{25}NOS$ = 459.61) |

III. Synthesis of Final Product

1. Synthesis Example of A-3

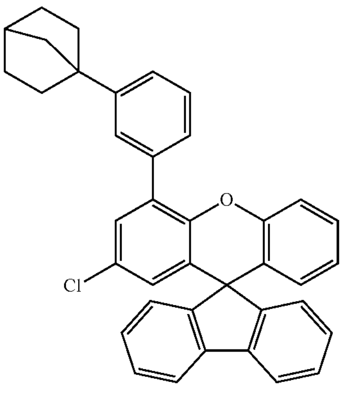

Sub 1-3

+

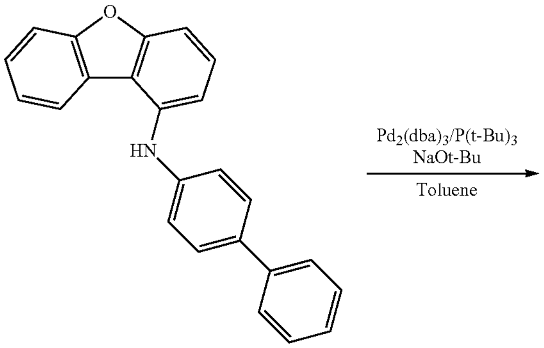

Sub 2-34

-continued

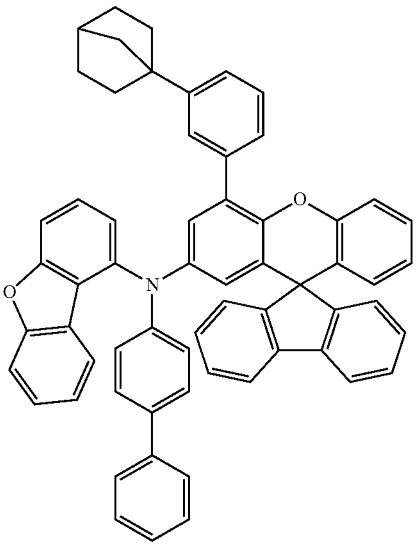

A-3

After dissolving Sub 1-3 (10 g, 18.6 mmol) with Toluene (250 mL) in a round bottom flask, Sub 2-34 (6.2 g, 18.6 mmol), $Pd_2(dba)_3$ (0.5 g, 0.6 mmol), $P(t\text{-}Bu)_3$ (50 wt % Sol.) (0.5 mL, 1.1 mmol), NaOt-Bu (5.8 g, 55.9 mmol) were added and stirred at 80° C. when the reaction was complete, the mixture was extracted with $CH_2Cl_2$ and water, the organic layer was dried over $MgSO_4$, concentrated, and the resulting compound was purified by silicagel column and sublimation to obtain 13.5 g (yield: 87%) of the product.

2. Synthesis Example of A-6

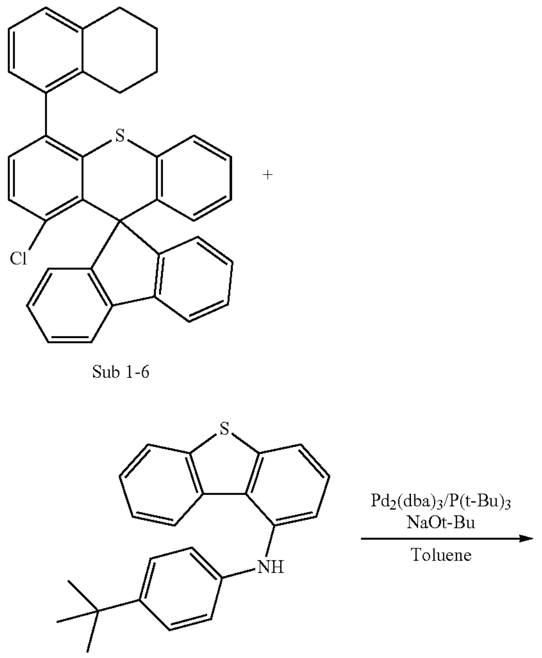

Sub 1-6

Sub 2-6

-continued

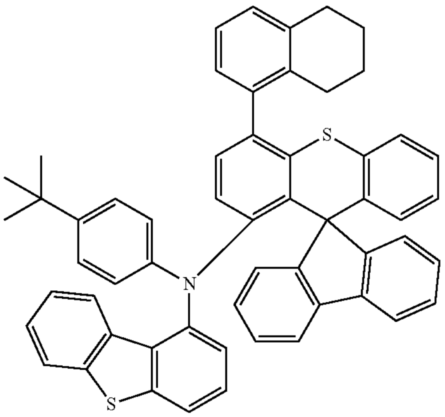

A-6

Sub 1-6 (13 g, 25.3 mmol) and Sub 2-6 (8.4 g, 25.3 mmol), $Pd_2(dba)_3$ (0.7 g, 0.8 mmol), NaOt-Bu (7.3 g, 76.0 mmol), Anhydrous Toluene (270 mL), $P(t\text{-}Bu)_3$ (50 wt % Sol.) (0.6 mL, 1.5 mmol) were used for the synthesis of A-3 to obtain 18.2 g (yield: 89%) of the product.

3. Synthesis Example of A-9

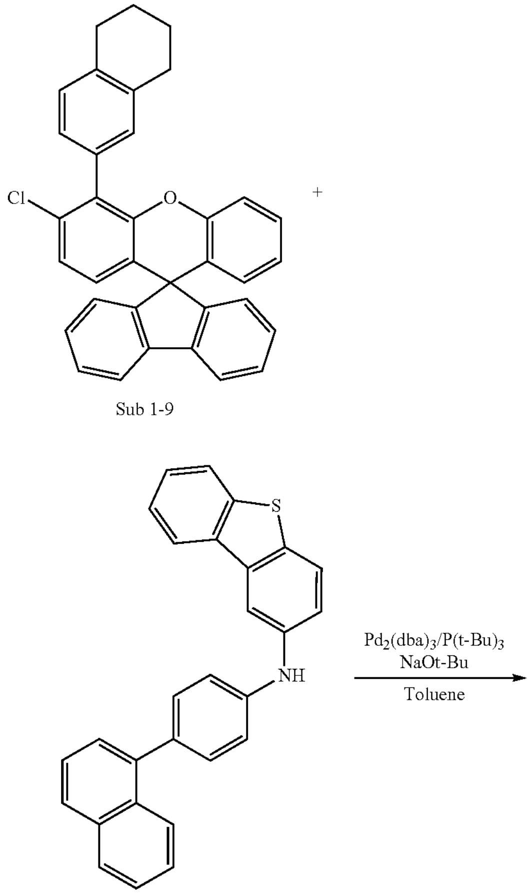

Sub 1-9

Sub 2-9

-continued

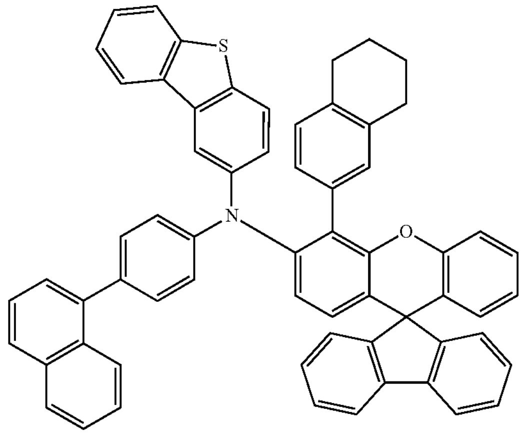

A-9

Sub 1-9 (12.0 g, 24.1 mmol) and Sub 2-9 (9.7 g, 24.1 mmol), $Pd_2(dba)_3$ (0.7 g, 0.7 mmol), NaOt-Bu (7.0 g, 72.4 mmol), Anhydrous Toluene (270 mL), $P(t\text{-}Bu)_3$ (50 wt % Sol.) (0.6 mL, 1.5 mmol) were used for the synthesis of A-3 to obtain 17.7 g (yield: 85%) of the product.

4. Synthesis Example of A-31

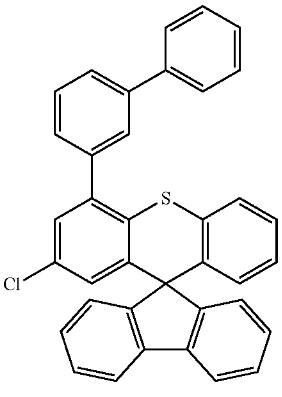

Sub 1-22

+

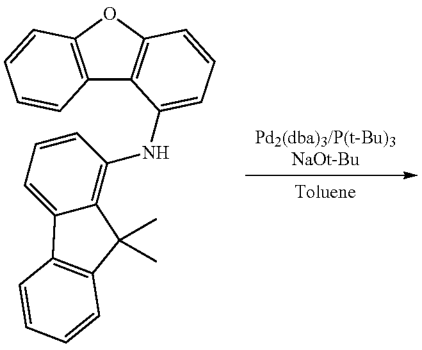

Sub 2-30

-continued

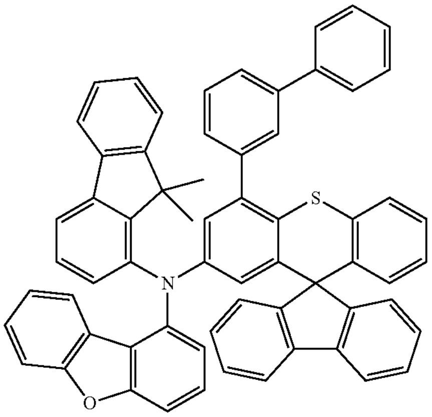

A-31

Sub 1-22 (15.0 g, 28.0 mmol) and Sub 2-30 (10.5 g, 28.0 mmol), $Pd_2(dba)_3$ (0.8 g, 0.8 mmol), NaOt-Bu (8.1 g, 84.1 mmol), Anhydrous Toluene (280 mL), $P(t\text{-}Bu)_3$ (50 wt % Sol.) (0.7 mL, 1.7 mmol) were used for the synthesis of A-3 to obtain 20.1 g (yield: 82%) of the product.

5. Synthesis Example of A-35

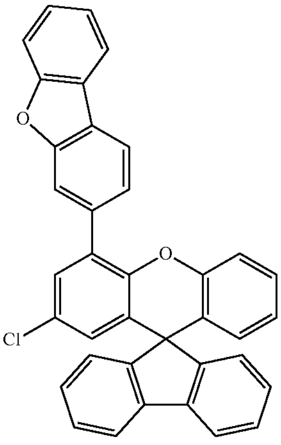

Sub 1-31

+

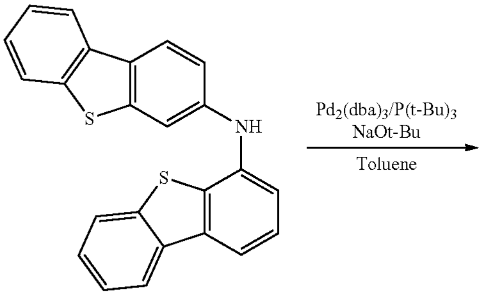

Sub 2-94

-continued

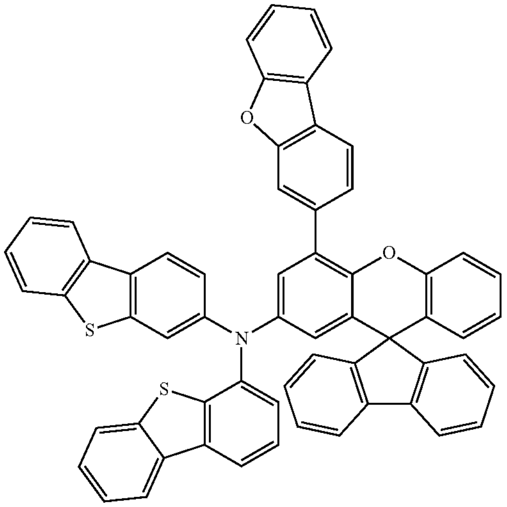

A-35

Sub 1-31 (11.0 g, 20.6 mmol) and Sub 2-94 (7.9 g, 20.6 mmol), $Pd_2(dba)_3$ (0.6 g, 0.6 mmol), NaOt-Bu (6.0 g, 61.9 mmol), Anhydrous Toluene (250 mL), $P(t-Bu)_3$ (50 wt % Sol.) (0.5 mL, 1.2 mmol) were used for the synthesis of A-3 to obtain 14.3 g (yield: 79%) of the product.

6. Synthesis Example of A-81

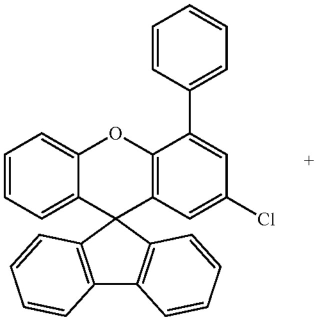

Sub 1-20

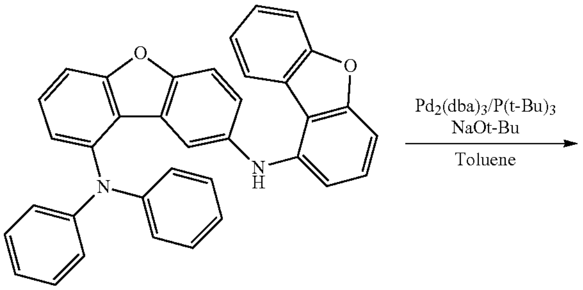

Sub 2-72

-continued

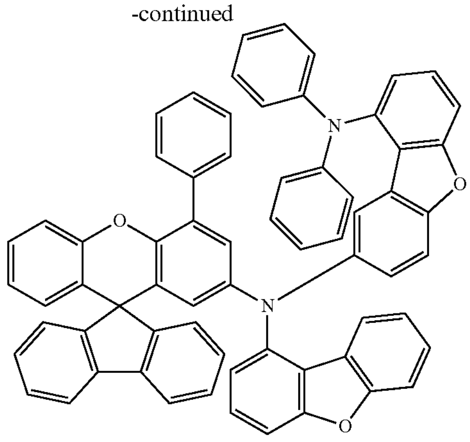

A-81

Sub 1-20 (10.0 g, 22.6 mmol) and Sub 2-72 (11.7 g, 22.6 mmol), $Pd_2(dba)_3$ (0.6 g, 0.7 mmol), NaOt-Bu (6.5 g, 67.7 mmol), Anhydrous Toluene (250 mL), $P(t-Bu)_3$ (50 wt % Sol.) (0.5 mL, 1.4 mmol) were used for the synthesis of A-3 to obtain 16.9 g (yield: 81%) of the product.

Meanwhile, FD-MS values of compounds A-1 to A-112 of the present invention prepared according to the above synthesis examples are shown in Table 3.

TABLE 3

| compound | FD-MS |
|---|---|
| A-1 | m/z = 799.35($C_{59}H_{45}NO_2$ = 800.01) |
| A-2 | m/z = 891.35($C_{65}H_{49}NOS$ = 892.17) |
| A-3 | m/z = 835.35($C_{62}H_{45}NO_2$ = 836.05) |
| A-4 | m/z = 835.35($C_{62}H_{45}NO_2$ = 836.05) |
| A-5 | m/z = 907.35($C_{68}H_{45}NO_2$ = 908.11) |
| A-6 | m/z = 807.30($C_{57}H_{45}NS_2$ = 808.11) |
| A-7 | m/z = 911.38($C_{68}H_{49}NO_2$ = 912.14) |
| A-8 | m/z = 797.33($C_{59}H_{43}NO_2$ = 798.00) |
| A-9 | m/z = 861.31($C_{63}H_{43}NOS$ = 862.10) |
| A-10 | m/z = 879.35($C_{64}H_{49}NOS$ = 880.16) |
| A-11 | m/z = 931.38($C_{68}H_{53}NOS$ = 932.24) |
| A-12 | m/z = 863.38($C_{64}H_{49}NO_2$ = 864.10) |
| A-13 | m/z = 829.30($C_{59}H_{43}NO_2S$ = 830.06) |
| A-14 | m/z = 905.33($C_{65}H_{47}NO_2S$ = 906.16) |
| A-15 | m/z = 951.41($C_{71}H_{53}NO_2$ = 952.21) |
| A-16 | m/z = 795.28($C_{5\&}H_{37}NO_3$ = 795.94) |
| A-17 | m/z = 899.27($C_{65}H_{41}NS_2$ = 900.17) |
| A-18 | m/z = 791.28($C_{59}H_{37}NO_2$ = 791.95) |
| A-19 | m/z = 817.30($C_{61}H_{39}NO_2$ = 817.99) |
| A-20 | m/z = 798.27($C_{57}H_{38}N_2OS$ = 799.00) |
| A-21 | m/z = 797.33($C_{59}H_{43}NO_2$ = 798.00) |
| A-22 | m/z = 807.26($C_{59}H_{37}NOS$ = 808.01) |
| A-23 | m/z = 883.29($C_{65}H_{41}NOS$ = 884.11) |
| A-24 | m/z = 791.28($C_{59}H_{37}NO_2$ = 791.95) |
| A-25 | m/z = 880.31($C_{65}H_{40}N_2O_2$ = 881.05) |
| A-26 | m/z = 841.30($C_{63}H_{39}NO_2$ = 842.01) |
| A-27 | m/z = 831.28($C_{61}H_{37}NO_3$ = 831.97) |
| A-28 | m/z = 897.27($C_{65}H_{39}NO_2S$ = 898.09) |
| A-29 | m/z = 781.30($C_{58}H_{39}NO_2$ = 781.95) |
| A-30 | m/z = 797.28($C_{58}H_{39}NOS$ = 798.02) |
| A-31 | m/z = 873.31($C_{64}H_{43}NOS$ = 874.11) |
| A-32 | m/z = 879.35($C_{64}H_{49}NOS$ = 880.16) |
| A-33 | m/z = 923.29($C_{67}H_{41}NO_2S$ = 924.13) |
| A-34 | m/z = 863.23($C_{61}H_{37}NOS_2$ = 864.09) |
| A-35 | m/z = 877.21($C_{61}H_{35}NO_2S_2$ = 878.08) |
| A-36 | m/z = 831.28($C_{61}H_{37}NO_3$ = 831.97) |
| A-37 | m/z = 939.26($C_{67}H_{41}NOS_2$ = 940.19) |
| A-38 | m/z = 910.31($C_{64}H_{34}D_7NOS_2$ = 911.20) |
| A-39 | m/z = 898.32($C_{65}H_{42}N_2O_3$ = 899.06) |
| A-40 | m/z = 966.27($C_{68}H_{42}N_2OS_2$ = 967.22) |
| A-41 | m/z = 965.31($C_{70}H_{47}NS_2$ = 966.27) |
| A-42 | m/z = 963.32($C_{70}H_{45}NO_2S$ = 964.19) |
| A-43 | m/z = 913.34($C_{67}H_{47}NOS$ = 914.18) |

TABLE 3-continued

| compound | FD-MS |
|---|---|
| A-44 | m/z = 897.27($C_{65}H_{39}NO_2S$ = 898.09) |
| A-45 | m/z = 847.25($C_{61}H_{37}NO_2S$ = 848.03) |
| A-46 | m/z = 905.33($C_{6\&}H_{43}NO_2$ = 906.10) |
| A-47 | m/z = 833.28($C_{61}H_{39}NOS$ = 834.05) |
| A-48 | m/z = 921.31($C_{6\&}H_{43}NOS$ = 922.16) |
| A-49 | m/z = 929.22($C_{65}H_{39}NS_3$ = 930.21) |
| A-50 | m/z = 921.31($C_{68}H_{43}NOS$ = 922.16) |
| A-51 | m/z = 909.31($C_{67}H_{43}NOS$ = 910.15) |
| A-52 | m/z = 919.29($C_{68}H_{41}NOS$ = 920.14) |
| A-53 | m/z = 863.23($C_{61}H_{37}NOS_2$ = 864.09) |
| A-54 | m/z = 921.31($C_{68}H_{43}NOS$ = 922.16) |
| A-55 | m/z = 1031.38($C_{7\&}H_{49}NO_2$ = 1032.25) |
| A-56 | m/z = 919.29($C_{6\&}H_{41}NOS$ = 920.14) |
| A-57 | m/z = 913.39($C_{68}H_{51}NO_2$ = 914.16) |
| A-58 | m/z = 894.32($C_{64}H_{38}D_5NS_2$ = 895.21) |
| A-59 | m/z = 954.37($C_{70}H_{42}D_5NOS$ = 955.24) |
| A-60 | m/z = 930.37($C_{68}H_{3\&}D_7NOS$ = 931.22) |
| A-61 | m/z = 838.32($C_{61}H_{30}D_7NO_3$ = 839.01) |
| A-62 | m/z = 869.31($C_{62}H_{47}NS_2$ = 870.18) |
| A-63 | m/z = 927.31($C_{67}H_{37}D_4NO_2S$ = 928.15) |
| A-64 | m/z = 992.43($C_{74}H_{40}D_9NO_2$ = 993.27) |
| A-65 | m/z = 1003.38($C_{74}H_{53}NOS$ = 1004.30) |
| A-66 | m/z = 855.35($C_{62}H_{49}NOS$ = 856.14) |
| A-67 | m/z = 979.35($C_{74}H_{45}NO_2$ = 980.18) |
| A-68 | m/z = 923.27($C_{67}H_{41}NS_2$ = 924.19) |
| A-69 | m/z = 953.33($C_{69}H_{47}NO_2S$ = 954.20) |
| A-70 | m/z = 919.31($C_{68}H_{41}NO_3$ = 920.08) |
| A-71 | m/z = 961.39($C_{72}H_{51}NO_2$ = 962.20) |
| A-72 | m/z = 919.31($C_{68}H_{41}NO_3$ = 920.08) |
| A-73 | m/z = 928.37($C_{67}H_{48}N_2O_3$ = 929.13) |
| A-74 | m/z = 1106.43($C_{81}H_{58}N_2OS$ = 1107.43) |
| A-75 | m/z = 1146.46($C_{84}H_{62}N_2OS$ = 1147.49) |
| A-76 | m/z = 970.45($C_{71}H_{58}N_2O_2$ = 971.26) |
| A-77 | m/z = 960.32($C_{67}H_{48}N_2OS_2$ = 961.25) |
| A-78 | m/z = 966.42($C_{71}H_{54}N_2O_2$ = 967.23) |
| A-79 | m/z = 1146.46($C_{84}H_{62}N_2OS$ = 1147.49) |
| A-80 | m/z = 888.32($C_{64}H_{44}N_2OS$ = 889.13) |
| A-81 | m/z = 922.32($C_{67}H_{42}N_2O_3$ = 923.08) |
| A-82 | m/z = 1020.27($C_{71}H_{44}N_2S_3$ = 1021.33) |
| A-83 | m/z = 1028.40($C_{75}H_{52}N_2O_3$ = 1029.25) |
| A-84 | m/z = 908.34($C_{67}H_{44}N_2O_2$ = 909.10) |
| A-85 | m/z = 1014.33($C_{73}H_{46}N_2O_2S$ = 1015.24) |
| A-86 | m/z = 1016.33($C_{73}H_{48}N_2S_2$ = 1017.32) |
| A-87 | m/z = 1005.38($C_{73}H_{43}D_5N_2OS$ = 1006.29) |
| A-88 | m/z = 1033.46($C_{76}H_{43}D_9N_2O_2$ = 1034.32) |
| A-89 | m/z = 1072.40($C_{80}H_{52}N_2O_2$ = 1073.31) |
| A-90 | m/z = 1088.38($C_{80}H_{52}N_2OS$ = 1089.37) |
| A-91 | m/z = 1072.40($C_{80}H_{52}N_2O_2$ = 1073.31) |
| A-92 | m/z = 1086.36($C_{80}H_{50}N_2OS$ = 1087.35) |
| A-93 | m/z = 938.30($C_{67}H_{42}N_2O_2S$ = 939.14) |
| A-94 | m/z = 1106.34($C_{79}H_{50}N_2OS_2$ = 1107.40) |
| A-95 | m/z = 964.35($C_{70}H_{48}N_2OS$ = 965.23) |
| A-96 | m/z = 1165.41($C_{85}H_{55}N_3OS$ = 1166.45) |
| A-97 | m/z = 1024.40($C_{76}H_{52}N_2O_2$ = 1025.26) |
| A-98 | m/z = 1088.38($C_{80}H_{52}N_2OS$ = 1089.37) |
| A-99 | m/z = 908.34($C_{67}H_{44}N_2O_2$ = 909.10) |
| A-100 | m/z = 1086.36($C_{80}H_{50}N_2OS$ = 1087.35) |
| A-101 | m/z = 964.34($C_{67}H_{32}D_{10}N_2OS_2$ = 965.27) |
| A-102 | m/z = 1106.37($C_{80}H_{54}N_2S_2$ = 1107.45) |
| A-103 | m/z = 1008.37($C_{75}H_{48}N_2O_2$ = 1009.22) |
| A-104 | m/z = 1014.33($C_{73}H_{46}N_2O_2S$ = 1015.24) |
| A-105 | m/z = 913.25($C_{65}H_{39}NOS_2$ = 914.15) |
| A-106 | m/z = 821.24($C_{59}H_{35}NO_2S$ = 821.99) |
| A-107 | m/z = 929.22($C_{65}H_{39}NS_3$ = 930.21) |
| A-108 | m/z = 929.33($C_{67}H_{47}NO_2S$ = 930.18) |
| A-109 | m/z = 847.25($C_{61}H_{37}NO_2S$ = 848.03) |
| A-110 | m/z = 847.25($C_{61}H_{37}NO_2S$ = 848.03) |
| A-111 | m/z = 939.26($C_{67}H_{41}NOS_2$ = 940.19) |
| A-112 | m/z = 941.33($C_{68}H_{47}NO_2S$ = 924.19) |

Evaluation of Manufacture of Organic Electronic element

[Example 1] Green Organic Light Emitting Diode (Emitting Auxiliary Layer)

An organic electroluminescent device was manufactured according to a conventional method using the compound of the present invention as an emitting auxiliary layer material. First, after vacuum deposition of 4,4',4"-Tris[2-naphthyl (phenyl)amino]triphenylamine (hereinafter, 2-TNATA) to a thickness of 60 nm on the ITO layer (anode) formed on the glass substrate to form a hole injection layer, N,N'-bis(1-naphthalenyl)-N,N'-bis-phenyl-(1,1'-biphenyl)-4,4'-diamine (hereinafter, NPB) was vacuum-deposited on the hole injection layer to a thickness of 60 nm to form a hole transport layer. Then, the compound A-3 was vacuum-deposited to a thickness of 20 nm on the hole transport layer to form an emitting auxiliary layer, 4,4'-N,N'-dicarbazole-biphenyl (hereinafter, CBP) as a host material and tris(2-phenylpyridine)-iridium (hereinafter, Ir(ppy)3) as a dopant material on the emitting auxiliary layer were doped at a weight ratio of 95:5, and then vacuum-deposited to a thickness of 30 nm to form an emitting layer. Then, (1,1'-biphenyl-4-olato)bis(2-methyl-8-quinolinolato)aluminum (hereinafter, BAlq) is vacuum-deposited to a thickness of 10 nm on the emitting layer to form a hole blocking layer, and on the hole blocking layer, tris-(8-hydroxyquinoline)aluminum (hereinafter, $Alq_3$) was vacuum-deposited to a thickness of 40 nm to form an electron transport layer. Thereafter, LiF, which is an alkali metal halide, was deposited to a thickness of 0.2 nm to form an electron injection layer, and then A1 was deposited to a thickness of 150 nm to form a cathode, thereby manufacturing an organic electroluminescent device.

[Example 2] to [Example 21] Green Organic Light Emitting Diode (Emitting Auxiliary Layer)

An organic light emitting diode was manufactured in the same manner as in Example 1, except that the compound of the present invention described in Table 4 were used instead of A-3 as the emitting auxiliary layer material.

[Comparative Example 1] to [Comparative Example 2]

An organic light emitting diode was manufactured in the same manner as in Example 1, Except that the comparative compound 1 or the comparative compound 2 described in Table 4 were used instead of A-3 as the emitting auxiliary layer material <comparative compound 1>

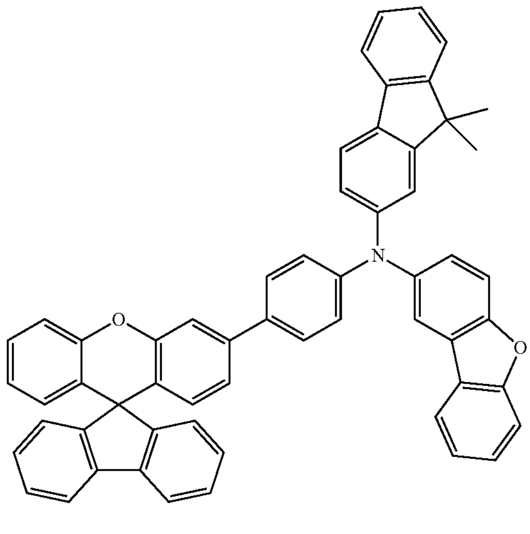

-continued

<comparative compound 2>

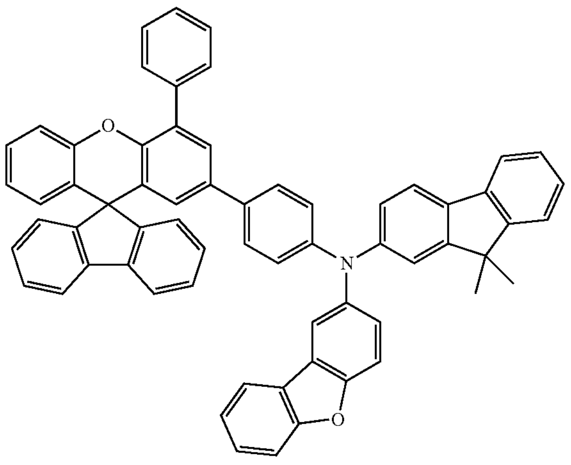

Electroluminescence (EL) characteristics were measured by PR-650 of photoresearch company by applying a forward bias direct current voltage to the organic light emitting diodes prepared according to Examples 1 to 21 and Comparative Example 1 to Comparative Example 2 of the present invention, T95 life was measured through a life measurement equipment manufactured by McScience at a luminance of 5000 cd/m$^2$, and the measurement results are shown in Table 4.

In detail, the comparative compound and the compound of the present invention are the same in including a xanthene core and an amine substituent, but there is a difference in the presence or absence of a secondary substituent of the xanthene core and a linkage between the xanthene and an amine.

First, when Comparative Compound 1 and Comparative Compound 2 are compared, it can be seen that Comparative Compound 2 in which a secondary substituent is further substituted at the 4th position of the xanthene core has improved device results than Comparative Compound 1 with no substituents attached. These results show that the value of the energy level (HOMO, LUMO level) is changed according to the presence or absence of bonding of the secondary substituent and the bonding position, and the physical properties of the compound are changed, thereby affecting the overall device performance.

Furthermore, Comparative Compound 2 and the compound of the present invention are the same in that the secondary substituent is bonded to the 4th position of the xanthene core, but there is a difference in the presence or absence of a linking group between the xanthene core and the amine group. In other words, in the case of Comparative Compound 2, an amine group is bonded to the secondary substituted xanthene core through a linking group phenylene, whereas in the compound of the present invention, an amine group is substituted by a direct bond, as a result, it can be seen that the element made of the compound of the present invention in which an amine group is bonded to the 4-position of the secondary substituted xanthene core by a direct bond has the best performance.

TABLE 4

| | compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comparative example (1) | comparative compound 1 | 5.9 | 28.7 | 5000.0 | 17.4 | 86.5 | 0.34 | 0.60 |
| comparative example (2) | comparative compound 2 | 5.7 | 24.8 | 5000.0 | 20.2 | 98.3 | 0.31 | 0.63 |
| example(1) | A-3 | 4.7 | 10.3 | 5000.0 | 48.5 | 131.5 | 0.31 | 0.62 |
| example(2) | A-9 | 4.8 | 11.1 | 5000.0 | 45.1 | 130.9 | 0.33 | 0.63 |
| example(3) | A-10 | 4.7 | 10.0 | 5000.0 | 50.0 | 133.4 | 0.33 | 0.62 |
| example(4) | A-13 | 4.8 | 9.9 | 5000.0 | 50.7 | 130.5 | 0.32 | 0.60 |
| example(5) | A-27 | 4.8 | 9.9 | 5000.0 | 50.6 | 133.8 | 0.35 | 0.62 |
| example(6) | A-29 | 4.7 | 10.0 | 5000.0 | 50.2 | 134.2 | 0.32 | 0.64 |
| example(7) | A-36 | 4.7 | 11.0 | 5000.0 | 45.5 | 132.3 | 0.35 | 0.63 |
| example(8) | A-37 | 4.9 | 9.6 | 5000.0 | 52.0 | 134.0 | 0.35 | 0.63 |
| example(9) | A-38 | 4.8 | 10.1 | 5000.0 | 49.3 | 134.6 | 0.31 | 0.64 |
| example(10) | A-42 | 4.8 | 10.5 | 5000.0 | 47.4 | 130.1 | 0.32 | 0.64 |
| example(11) | A-52 | 4.7 | 10.3 | 5000.0 | 48.7 | 133.5 | 0.31 | 0.62 |
| example(12) | A-54 | 4.8 | 10.0 | 5000.0 | 50.1 | 133.6 | 0.33 | 0.60 |
| example(13) | A-60 | 4.8 | 9.6 | 5000.0 | 51.8 | 132.6 | 0.32 | 0.64 |
| example(14) | A-72 | 4.9 | 10.6 | 5000.0 | 47.1 | 131.3 | 0.33 | 0.65 |
| example(15) | A-77 | 4.7 | 10.1 | 5000.0 | 49.7 | 132.7 | 0.31 | 0.63 |
| example(16) | A-80 | 4.9 | 9.7 | 5000.0 | 51.6 | 131.0 | 0.32 | 0.62 |
| example(17) | A-81 | 4.8 | 10.7 | 5000.0 | 46.8 | 130.9 | 0.32 | 0.64 |
| example(18) | A-89 | 4.8 | 11.1 | 5000.0 | 45.2 | 131.8 | 0.33 | 0.64 |
| example(19) | A-98 | 4.8 | 10.4 | 5000.0 | 47.9 | 131.0 | 0.30 | 0.63 |
| example(20) | A-106 | 4.7 | 10.1 | 5000.0 | 49.7 | 132.8 | 0.32 | 0.62 |
| example(21) | A-111 | 4.8 | 9.6 | 5000.0 | 51.9 | 132.4 | 0.31 | 0.62 |

As can be seen from the results in Table 4, when a green organic light emitting device is manufactured by using the material for an organic electrolumines cent device of the present invention as an emitting auxiliary layer material, compared to the case of using Comparative Compound 1 or Comparative Compound 2, the driving voltage of the organic light emitting device could be lowered, and efficiency and lifespan were significantly improved.

As a result, the amine group is directly bonded to the secondary substituted xanthene core, thereby having greater stereoscopicity, as a result, it is determined that the overall device performance is improved by adjusting the packing density between materials, even if a substituent is bonded at the same position, it suggests that the characteristics of the device may vary depending on the presence or absence of a linking group of the substituent.

Figure 4:
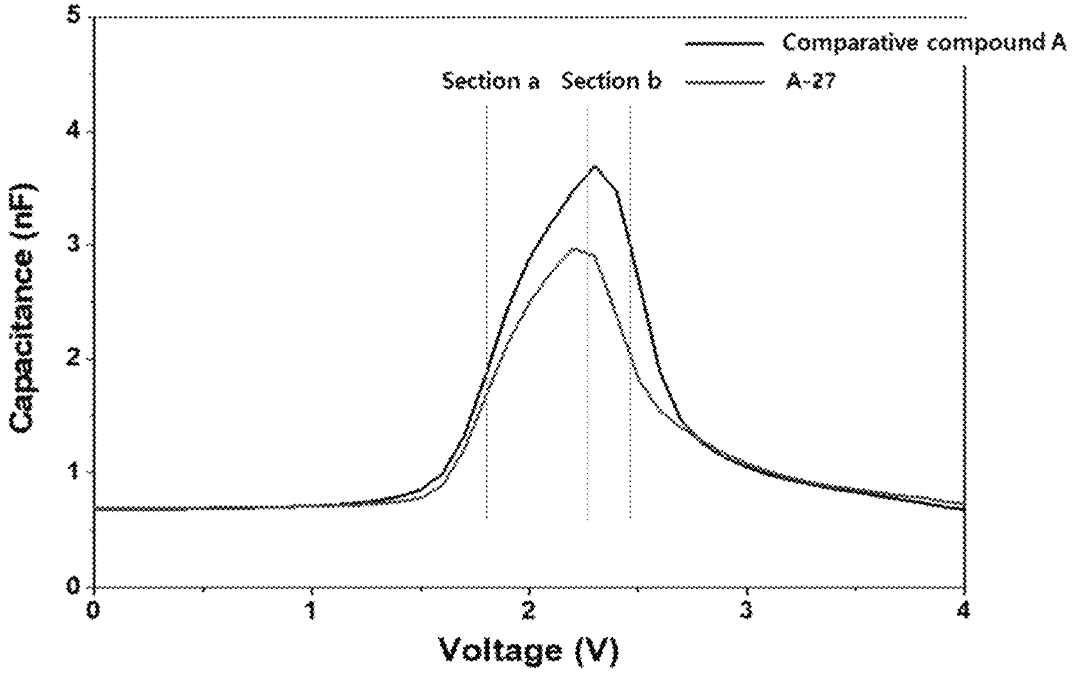
FIG. 4 is a graph of measuring capacitance change according to voltage of Comparative Compound A and Compound A-27 of the present invention in an alternating current (AC) driving circuit for OLED according to an embodiment of the present invention.

Additionally, FIG. 4 is a graph measuring the capacitance change according to the voltage of Comparative Compound A and Compound A-27 of the present invention in an alternating current (AC) driving circuit for OLED, and through this, it can be seen that a difference occurs in the capacitance of the compound depending on the presence or absence of a secondary substituent at a specific position of the xanthene core.

The three physical factors of capacitance are the active area of the capacitor conductors (plates), the distance between the conductors, and the dielectric constant of the dielectric medium used between the conductors, and by applying this, the capacitance can be expressed by the following equation.

$$C = \frac{\varepsilon_r \varepsilon_0 \times A}{d}$$

| Comparative compound A | A-27 |
|---|---|
| 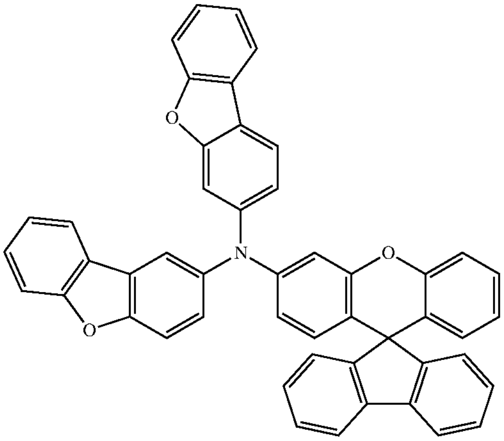 [SMILES: c1ccc2c(c1)Oc1cc(N(c3ccc4c(c3)oc3ccccc34)c3ccc4oc5ccccc5c4c3)ccc1C21c2ccccc2-c2ccccc21] | 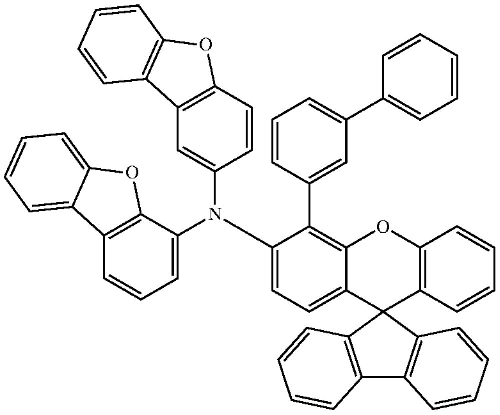 [SMILES: c1ccc(-c2cccc(-c3c(N(c4ccc5oc6ccccc6c5c4)c4cccc5c4oc4ccccc45)ccc4c3Oc3ccccc3C43c4ccccc4-c4ccccc43)c2)cc1] |

OLED displays require high device uniformity, but the current supplied to the pixels of the OLED changes, and the characteristics of the OLED device fluctuate, which causes deterioration of initial panel characteristics or image quality problems such as stains and afterimages, thereby causing reliability problems.

For this reason, it is important to increase the stability of the element, to be able to supply a constant charge according to the change of the element, and to facilitate the charge transfer at the interface of the OLED device.

In general, a capacitor tries to maintain a potential difference of the same magnitude as the power supply voltage by collecting charges (charging) when the voltage is high and releasing (discharging) the charges when the voltage is low. The charge/discharge cycle of such a capacitor varies depending on the ratio of the amount of charge stored when a voltage is applied, and capacitance indicates the ability to charge the charge of the capacitor.

The symbol of capacitance is C, and the unit is farad [F], and refers to a quantity representing the ratio of the amount of charge accumulated when a voltage is applied. If the accumulated charge in the capacitor is Q and the applied voltage is V, then a capacitance of 1F means that when a voltage of 1V is applied to the capacitor, a charge of 1C (coulomb) can be accumulated between two parallel plates. Here, the voltage V and the amount of charge Q are proportional to each other, and as the voltage V increases, the greater the amount of charge Q is charged. So, when the voltage V is the same, the larger the capacitance C, the more charge is charged.

That is, the relationship between the voltage, the amount of charge, and the capacitance is expressed as follows.

$$Q=C \times V$$

$\varepsilon_r$: relative permittivity (dielectric constant), $\varepsilon_0$ permittivity in vacuum, A: electrode plate area, d:distance between two electrodes An OLED device can be said to be a single capacitor made of a multi-layered organic material (dielectric) between two electrodes, and unlike general capacitors, when more than a certain amount of energy is applied to the element, the electric charge moves to the internal organic material layer, and the capacitance changes according to the internal charge transfer.

In other words, capacitance represents the charge storage capacity of a compound in an OLED device. When the capacitance is large, charges (holes) are continuously accumulated at the interface of the emitting auxiliary layer, and charge injection into the emitting layer is relatively slow, so that the charge transfer does not occur smoothly. Due to this, charges and electrons meet late in the emitting layer, and as the charge accumulates at the interface of the emitting auxiliary layer, it is not resolved well, so even if the power supply is stopped due to the charge remaining at the interface, a low gray phenomenon occurs in which current flows. As a result, this phenomenon causes a problem of deterioration of the image quality of the OLED device panel. Therefore, when a compound with a small capacitance is used in an OLED device, since the charge accumulation time at the interface of the emitting auxiliary layer is shortened and the charge is supplied to the emitting layer smoothly, the low gray phenomenon can be solved and the stability of the OLED device can be improved.

Referring to FIG. 4, it can be seen that the graph area of the compound A-27 of the present invention is small compared to the comparative compound A, which means that the capacitance of the compound A-27 of the present invention is smaller. In detail, Section a represents a change in capacitance due to charge (holes) injection from the emitting auxiliary layer to the emitting layer, and Section b is a section in which charges meet electrons in the emitting layer to recombine and emit light.

Comparative Compound A, which does not have a secondary substituent in the xanthene core, has a large capacitance, so charges are continuously accumulated at the interface or inside the emitting auxiliary layer, so that the charge injection into the emitting layer is delayed, so that the charge transfer is not performed smoothly. For this reason, it can be seen that the charge and the electron meet late in the emitting layer, and the charge transfer is not well resolved as the charge accumulates at the interface of the emitting auxiliary layer. That is, the organic electronic element using Comparative Compound A, even if power supply is stopped due to the charge remaining at the interface, may have a low gray phenomenon in which an afterimage of light remains may occur, which may cause deterioration of OLED device characteristics or image quality problems such as stains and afterimages, resulting in reliability problems. However, since the capacitance of Compound A-27 of the present invention is small, it can be seen that the capacitance rapidly decreases in Section b as charges are injected and discharged into the emitting layer as quickly as charges are accumulated at the interface or inside of the emitting auxiliary layer.

As a result, by using a compound in which a secondary substituent is bonded to the xanthene core, charge injection from the emitting auxiliary layer to the emitting layer is smoothly performed, so that the charge mobility is excellent, and through this, it is shown that the driving voltage, efficiency, and lifespan of the overall element are improved as the stability of the OLED device is increased.

In the case of the emitting auxiliary layer, the correlation between the hole transport layer and the emitting layer (host) should be understood, therefore it will be very difficult for a person skilled in the art to infer the characteristics of the emitting auxiliary layer in which the compound of the present invention is used even if a similar core is used.

Furthermore, although the element characteristics were described in which the compound of the present invention was applied to only one layer of the emitting auxiliary layer in the evaluation result of the above-described device fabrication, but it may also be applied to a case in which a hole transport layer or both a hole transport layer and an emitting auxiliary layer are formed using the compound of the present invention.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed:

1. A compound represented by Formula A:

<Formula A>

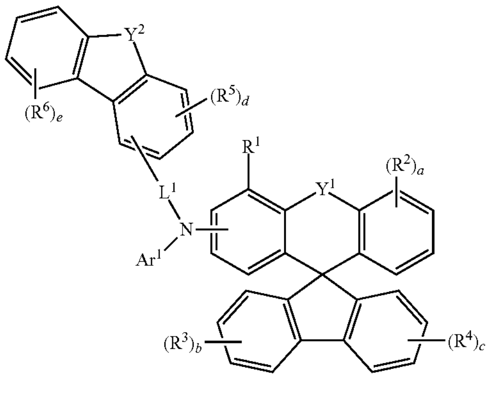

wherein:

1) $Y^1$ and $Y^2$ are each independently O or S;

2) $L^1$ is selected from the group consisting of single bond; a $C_6$-$C_{60}$ arylene group; a fluorenylene group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

3) $Ar^1$ is selected from the group consisting of $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

4) $R^1$ is selected from the group consisting of a $C_6$-$C_{60}$ aryl group; a fluorenyl group; a $C_3$-$C_{60}$ aliphatic cyclic group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

5) $R^2$, $R^3$, $R^4$, $R^5$ and $R^6$ are each independently selected from the group consisting of hydrogen; deuterium; tritium; halogen; cyano group; nitro group; $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; $C_1$-$C_{50}$ alkyl group; $C_2$-$C_{20}$ alkenyl group; $C_2$-$C_{20}$ alkynyl group; $C_1$-$C_{30}$ alkoxyl group; $C_6$-$C_{30}$ aryloxy group; and -L'-N($R^a$)($R^b$);

6) a, b, c and e are each independently an integer from 0 to 4, d is an integer from 0 to 3, wherein in case a, b, c and d are 2 or more, $R^2$, $R^3$, $R^4$, $R^5$ and $R^6$ are each in plural being the same or different, and an adjacent plurality of $R^2$ or a plurality of $R^3$ or a plurality of $R^4$ or a plurality of $R^5$ or a plurality of $R^6$ may be bonded to each other to form a ring, 7) L' is selected from the group consisting of single bond; a $C_6$-$C_{60}$ arylene group; a fluorenylene group; a $C_3$-$C_{60}$ aliphatic ring; a $C_2$-$C_{60}$ heterocyclic group including at least one heteroatom of O, N, S, Si or P; and combinations thereof, wherein $R^a$ and $R^b$ are each independently selected from the group consisting of a $C_6$-$C_{60}$ aryl group; a fluorenyl group; a $C_3$-$C_{60}$ aliphatic ring; a $C_2$-$C_{60}$ heterocyclic group including at least one heteroatom of O, N, S, Si or P; and combinations thereof, wherein, the aryl group, arylene group, heterocyclic group, fluorenyl group, fluorenylene group, fused ring group, alkyl group, alkenyl group, alkoxy group, aryloxy group and aliphatic cyclic group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; $C_8$-$C_{20}$ arylalkenyl group; and -L'-N($R_a$)($R_b$); wherein the substituents may be bonded to each other to form a saturated or unsaturated ring, wherein the term 'ring' means a $C_3$-$C_{60}$ aliphatic ring, a $C_6$-$C_{60}$ aromatic ring, or a $C_2$-$C_{60}$ heterocyclic group, or a fused ring formed by combination thereof.

2. The compound of claim 1, wherein Formula A is represented by Formula A-8:

<Formula A-8>

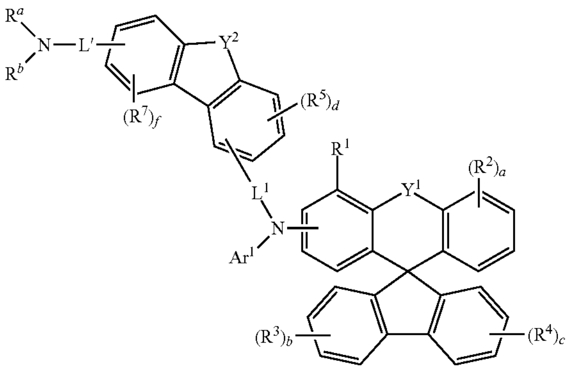

wherein $Y^1$, $Y^2$, $L^1$, $Ar^1$, $R^1$, $R^2$, $R^3$, $R^4$, $R^5$, a, b, c, d, L', $R^a$ and $R^b$ are the same as defined in claim 1, $R^7$ is the same as definition of $R^2$ in claim 1, and f is an integer of 0 to 3.

3. The compound of claim 1, wherein $Ar^1$ is represented by any one of Formulas Ar-1 to Ar-6:

<Formula Ar-1>

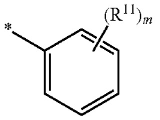

<Formula Ar-2>

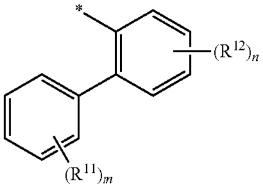

<Formula Ar-3>

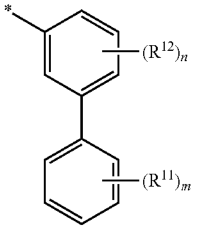

-continued

<Formula Ar-4>

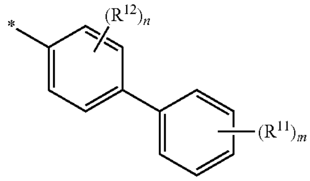

<Formula Ar-5>

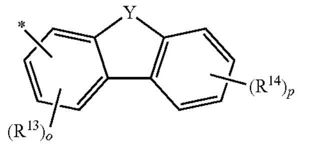

<Formula Ar-6>

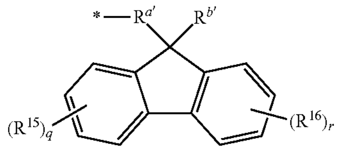

wherein:

*- indicates the bonding position, $R^{11}$, $R^{12}$, $R^{13}$, $R^{14}$, $R^{15}$ and $R^{16}$ are the same or different from each other and are each independently selected from the group consisting of hydrogen; deuterium; halogen; cyano group; nitro group; $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; $C_1$-$C_{50}$ alkyl group; $C_2$-$C_{20}$ alkenyl group; $C_2$-$C_{20}$ alkynyl group; $C_1$-$C_{30}$ alkoxyl group; $C_6$-$C_{30}$ aryloxy group;

Y is O, S, $CR^xR^y$ or $NR^z$, $R^{a'}$, $R^{b'}$, $R^x$, $R^y$ and $R^z$ are each independently selected from the group consisting of a $C_6$-$C_{60}$ aryl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; $C_1$-$C_{50}$ alkyl group; $C_2$-$C_{20}$ alkenyl group; $C_2$-$C_{20}$ alkynyl group; $C_1$-$C_{30}$ alkoxyl group; and $C_6$-$C_{30}$ aryloxy group; or $R^{a'}$ and $R^{b'}$ may be bonded to each other to form a ring, or $R^x$ and $R^y$ may be bonded to each other to form a ring, m is an integer from 0 to 5, n, p, q and r are each independently an integer from 0 to 4, and o is an integer from 0 to 3.

4. The compound of claim 1, wherein the compound represented by Formula A may be any one of the following compounds A-1 to A-112, but is not limited thereto:

A-1
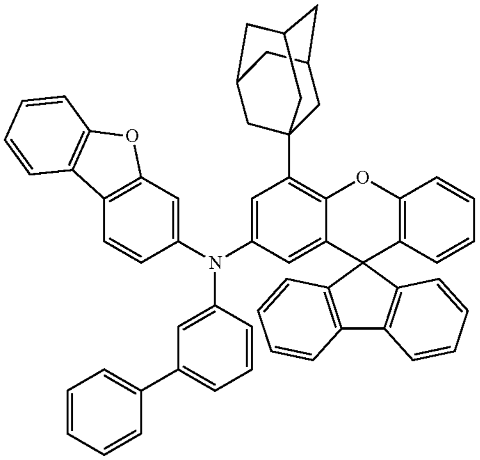
A-2
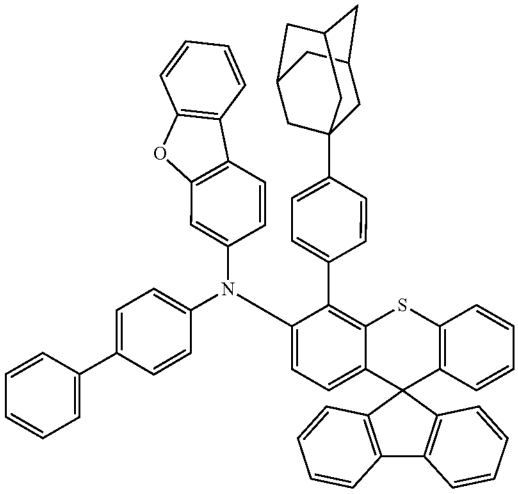
A-3
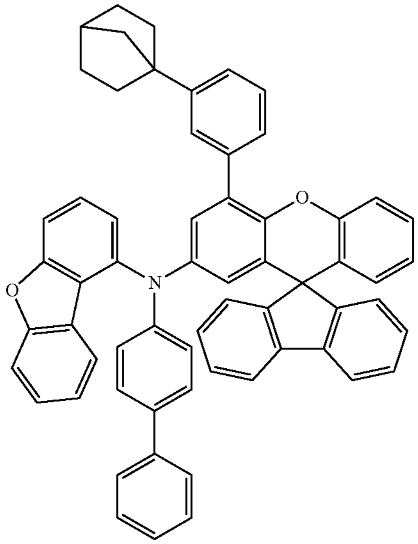
-continued
A-4
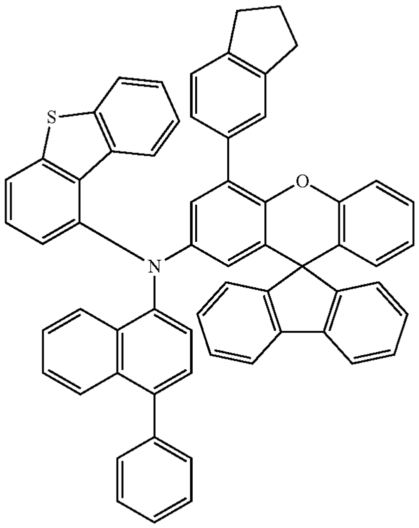
A-5
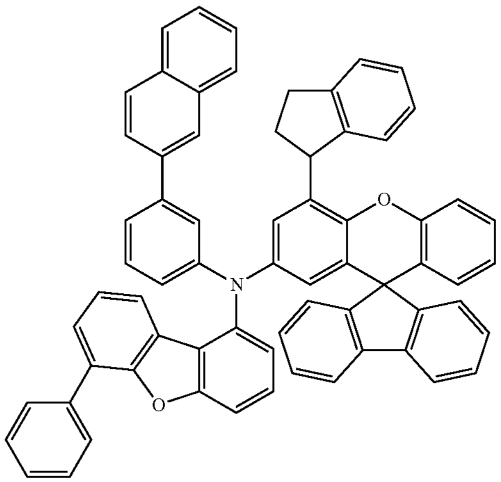
A-6
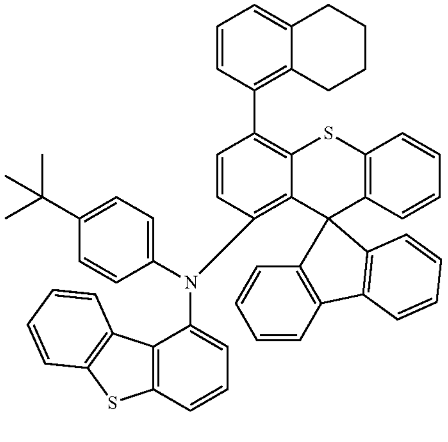

-continued
A-7
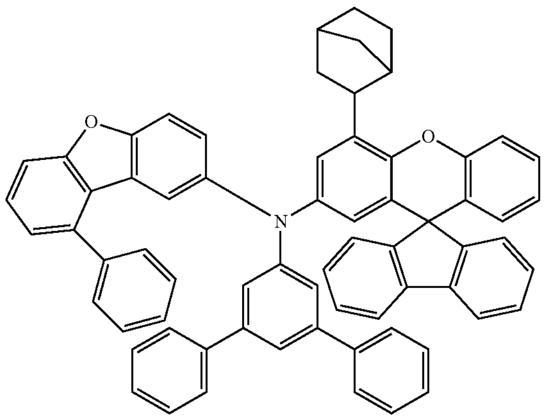
A-8
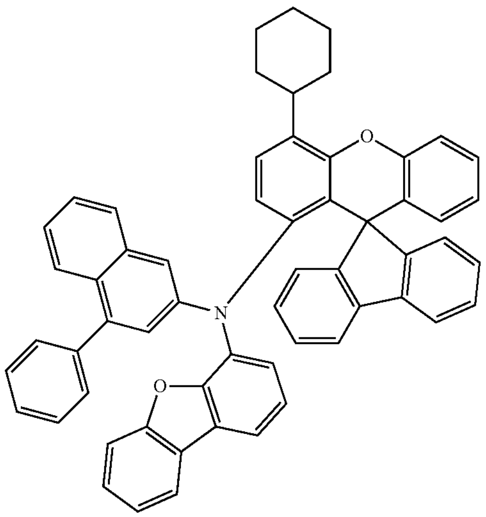
A-9
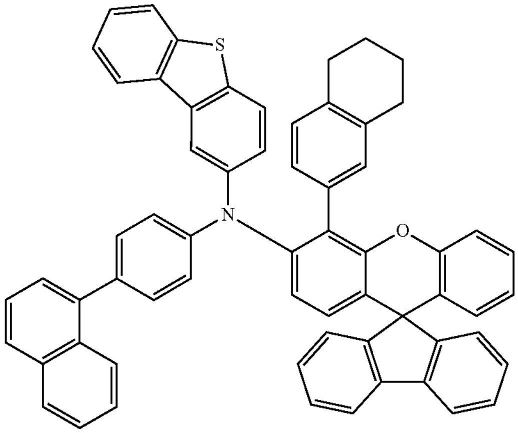
-continued
A-10
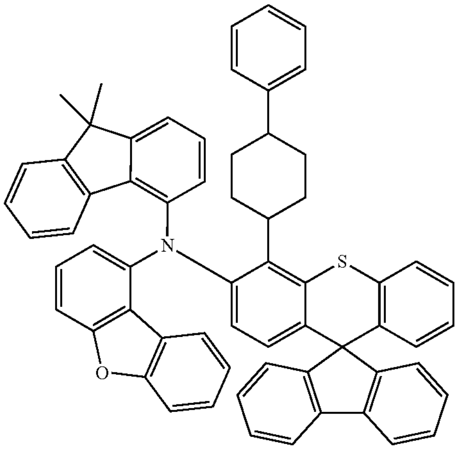
A-11
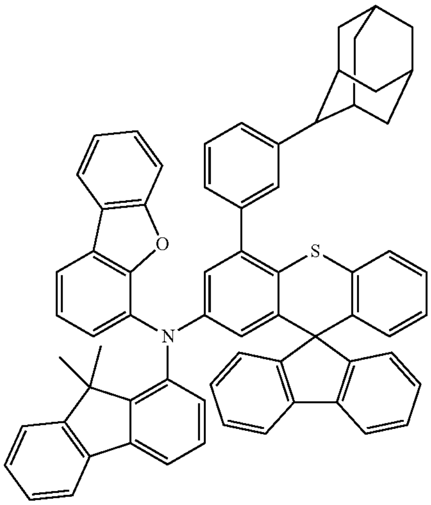
A-12
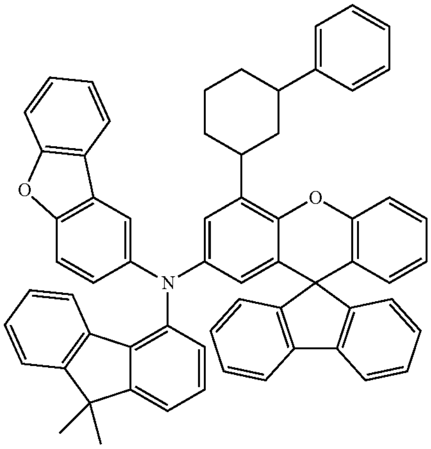

-continued
A-13
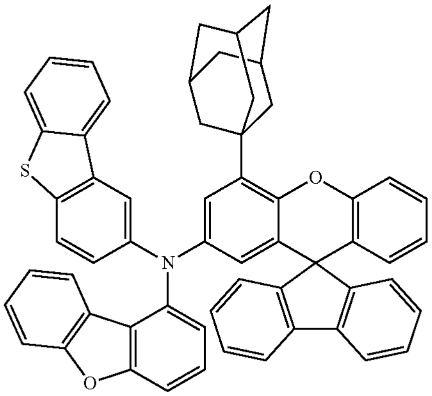
A-14
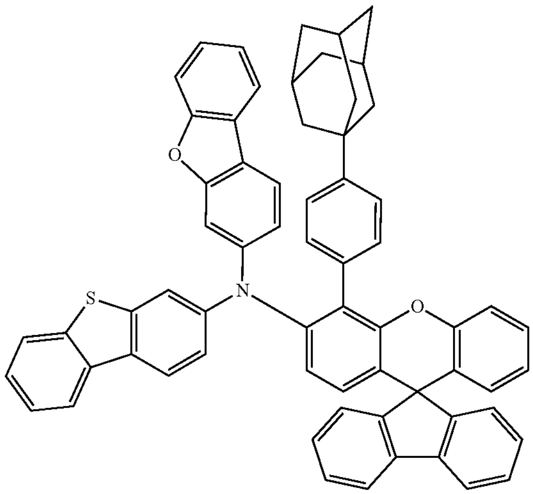
A-15
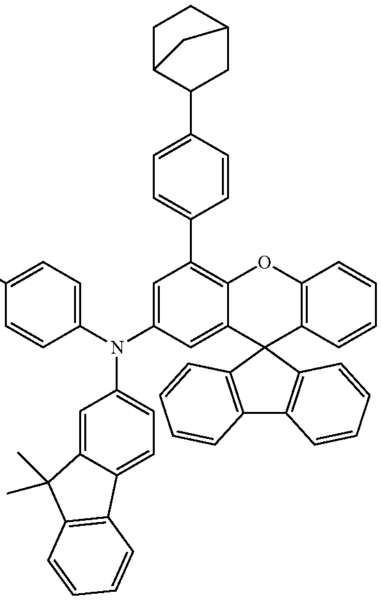
-continued
A-16
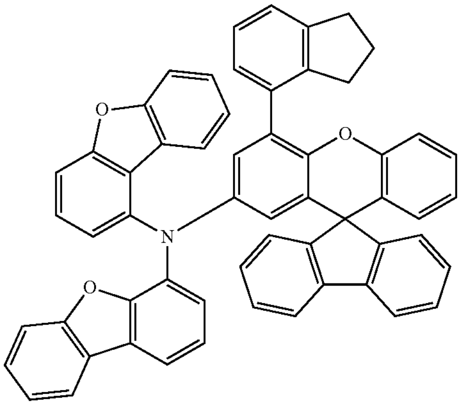
A-17
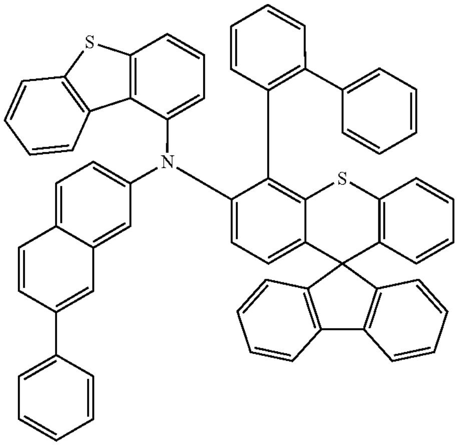
A-18
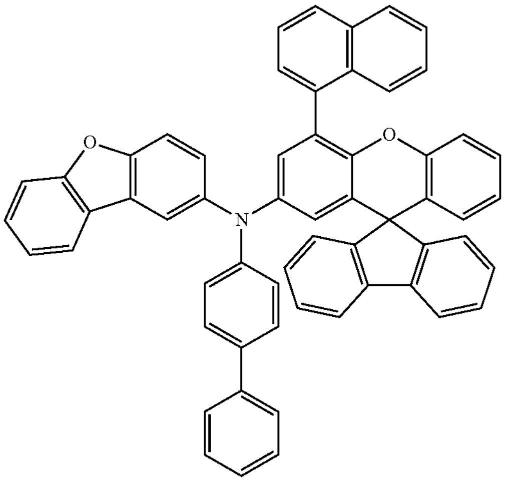

-continued
A-19
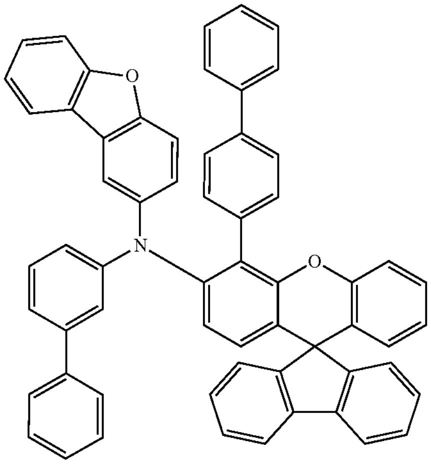
A-20
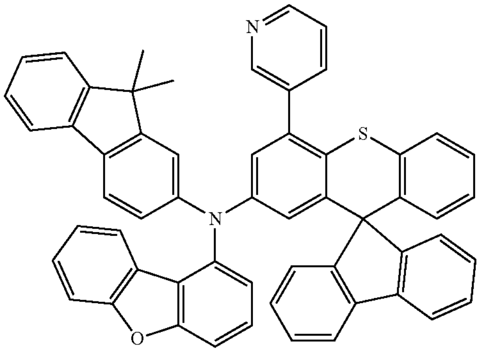
A-21
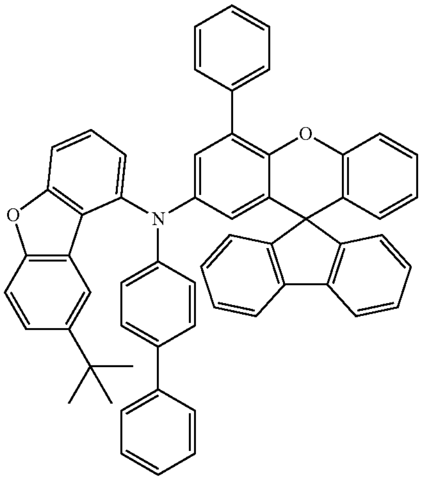
-continued
A-22
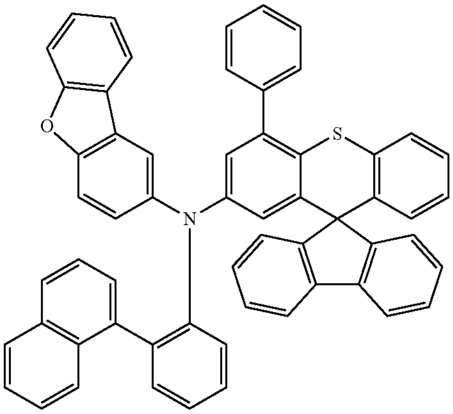
A-23
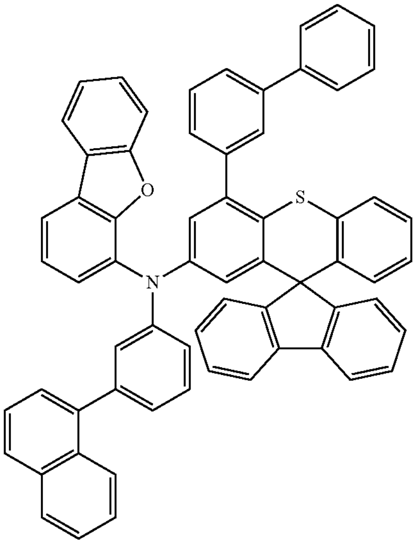
A-24
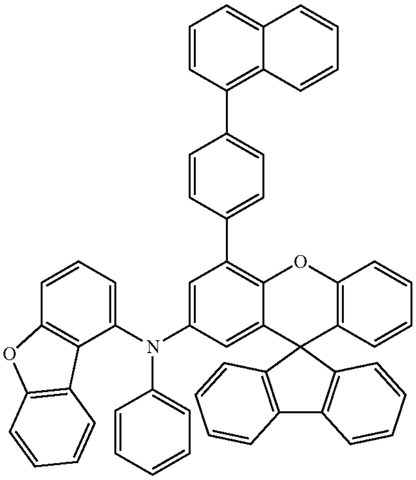

-continued
A-25
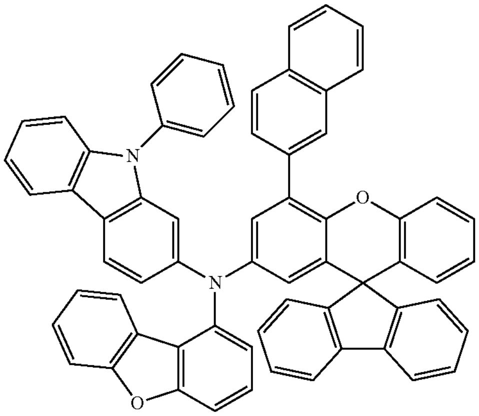
A-26
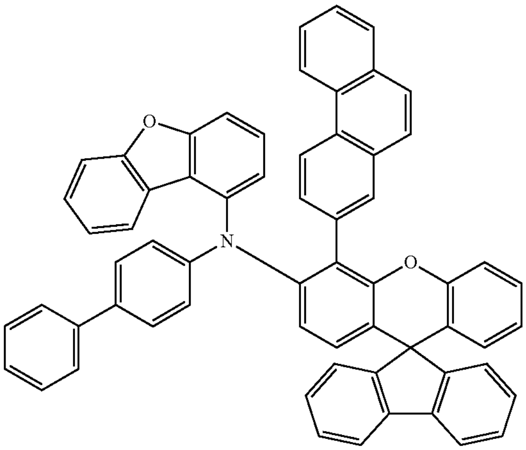
A-27
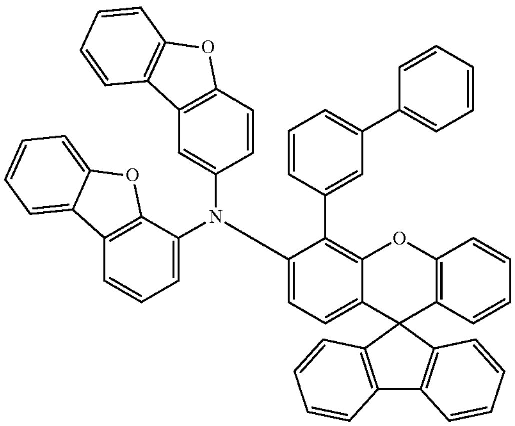
-continued
A-28
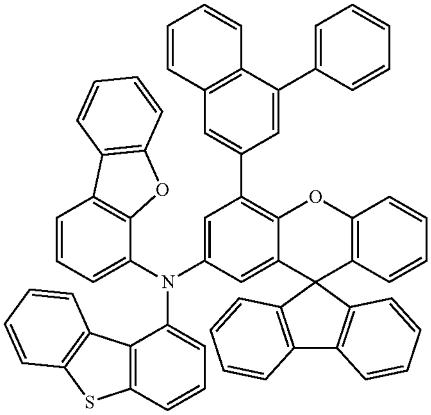
A-29
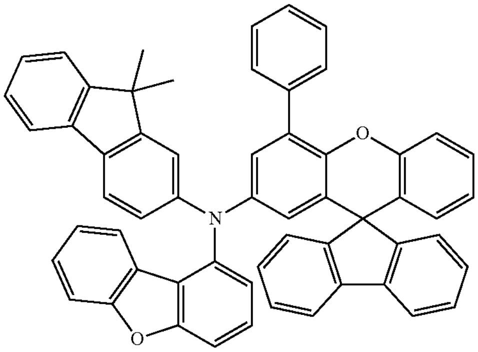
A-30
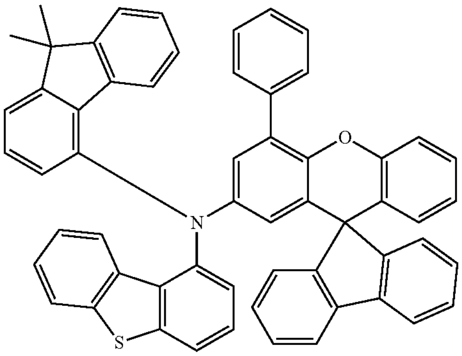
A-31
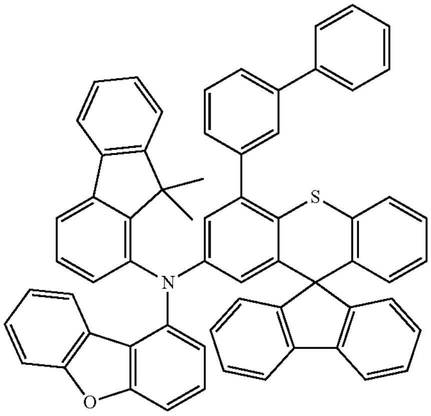

-continued
A-32
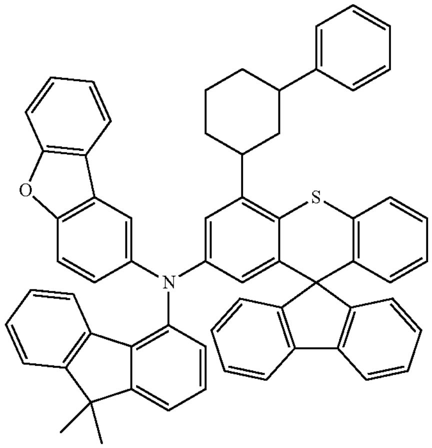
A-33
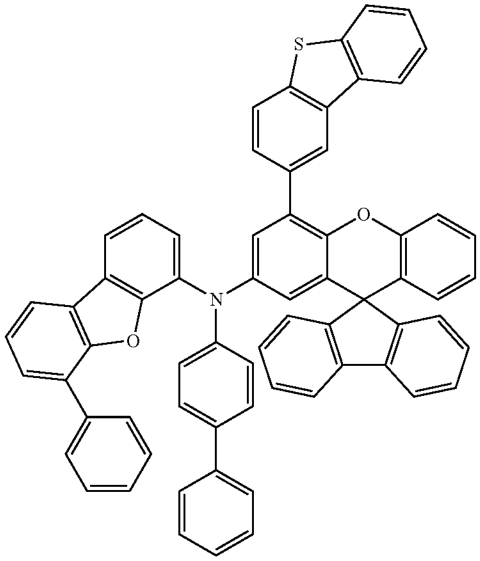
A-34
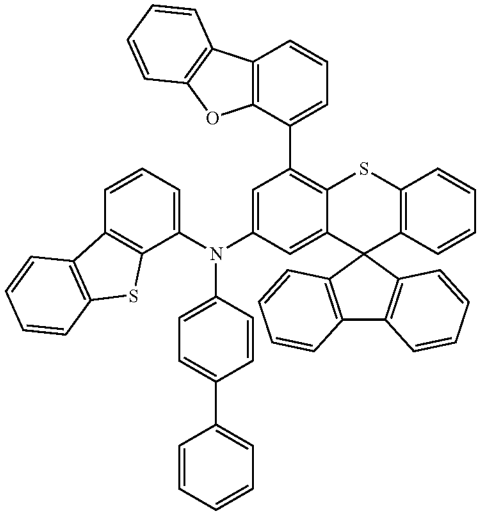
-continued
A-35
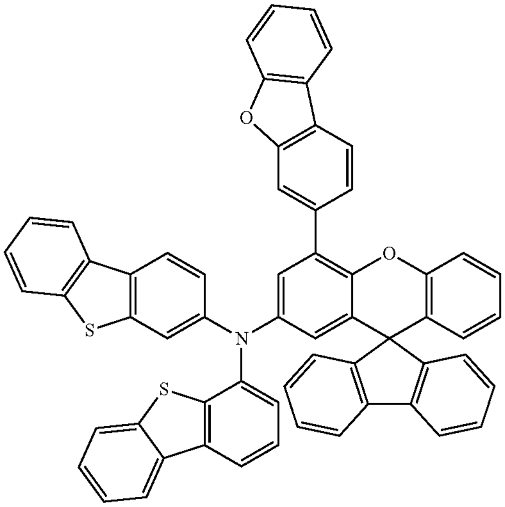
A-36
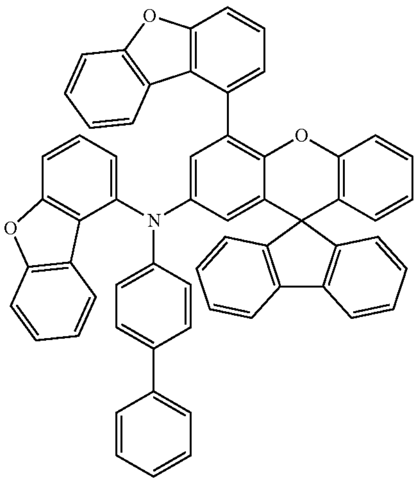
A-37
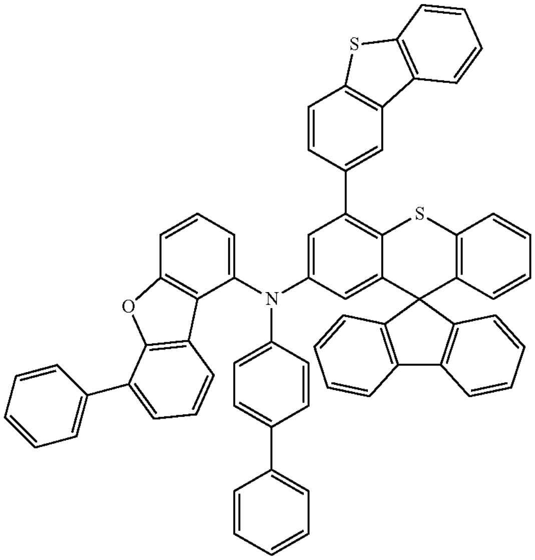

-continued
A-38
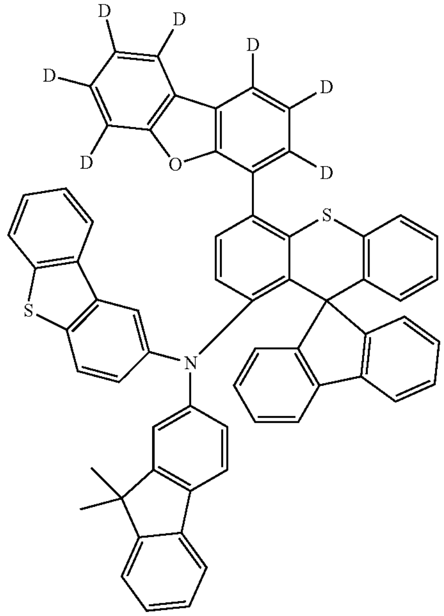
A-39
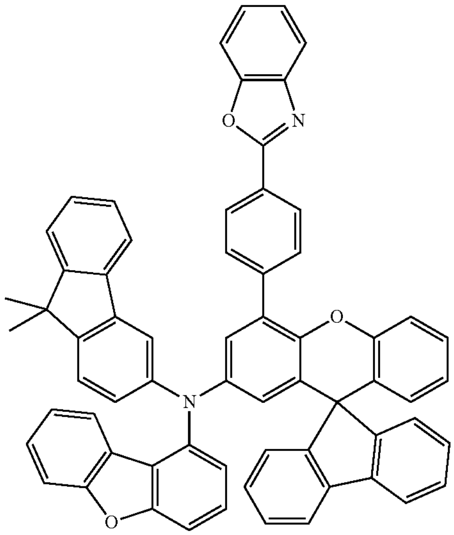
A-40
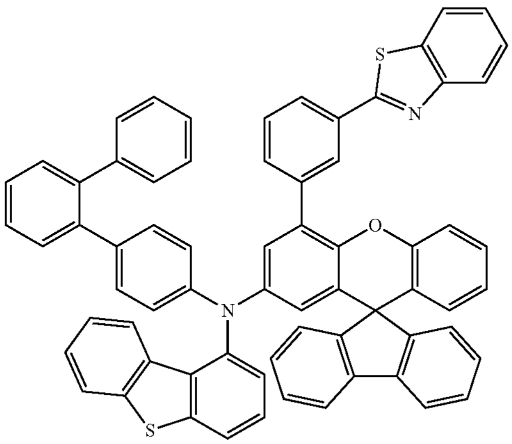
-continued
A-41
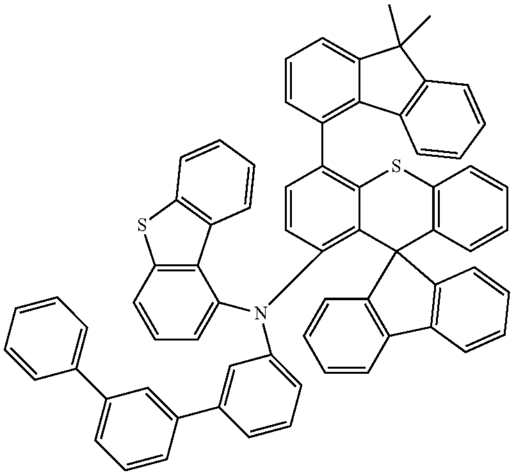
A-42
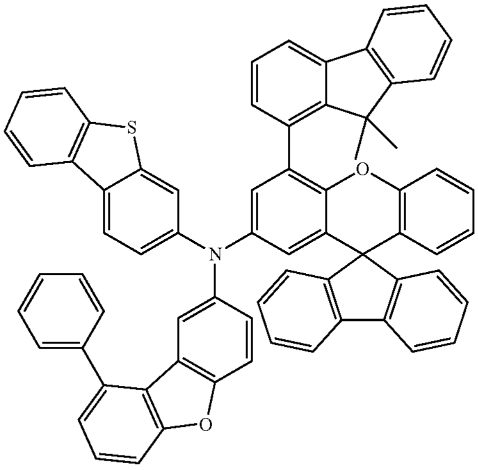
A-43
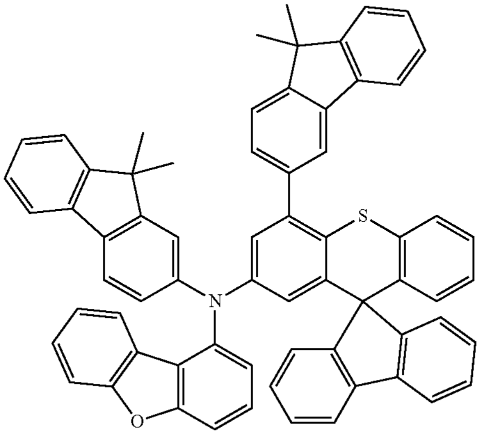

-continued
A-44
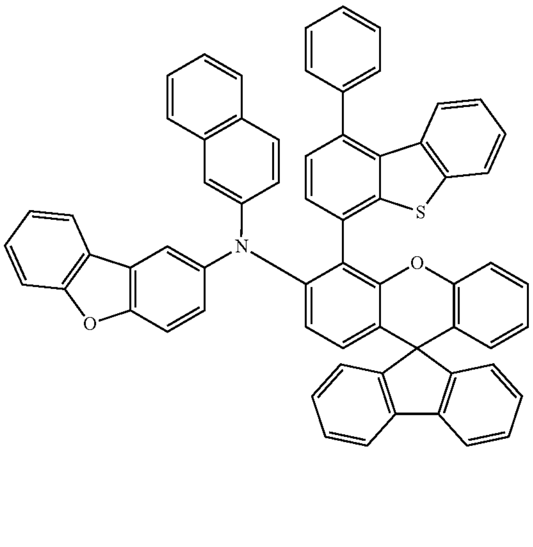
A-45
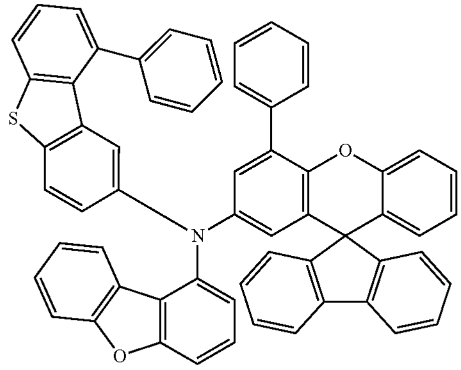
A-46
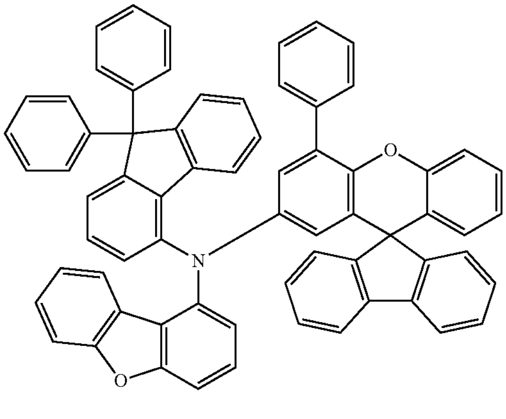
-continued
A-47
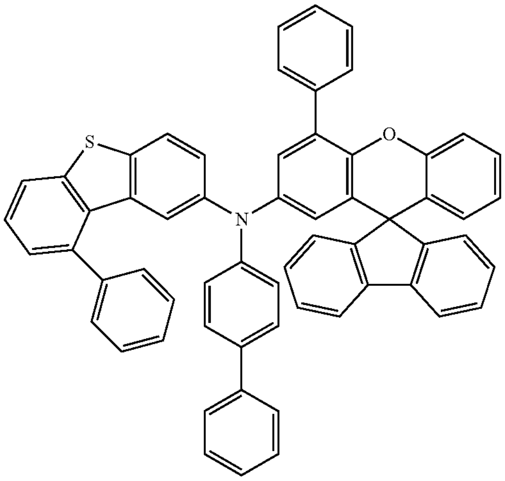
A-48
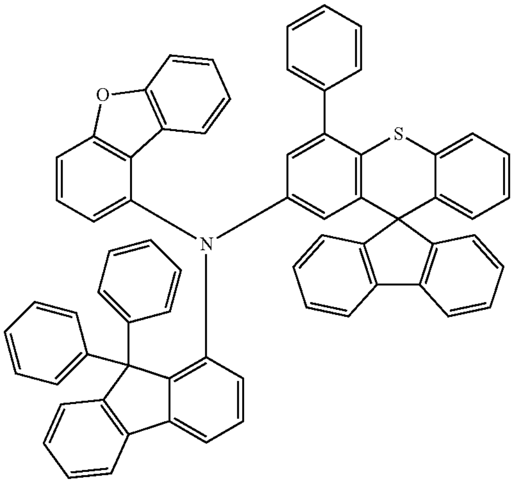
A-49
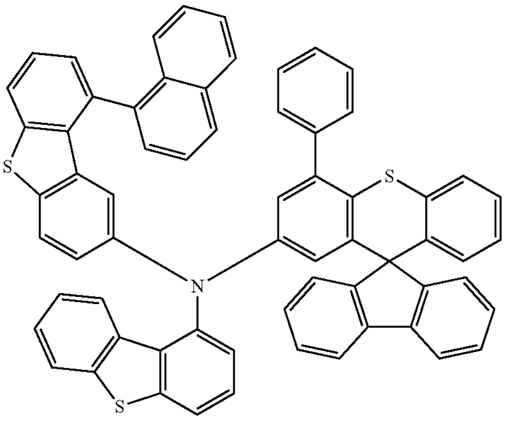

-continued
A-50
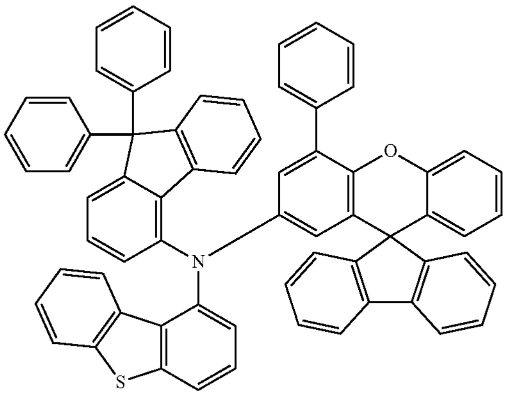
A-51
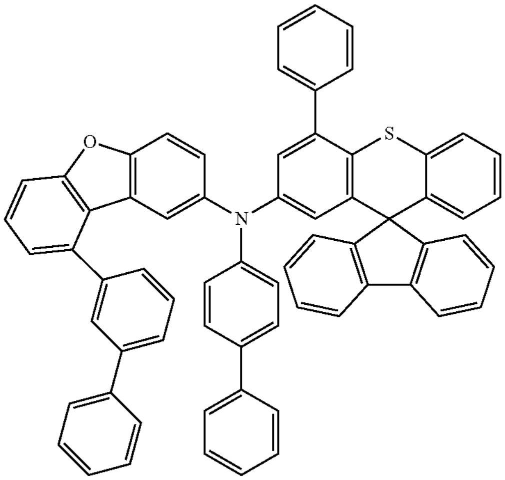
A-52
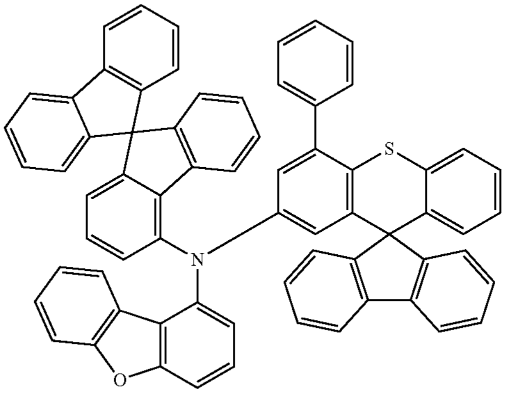
-continued
A-53
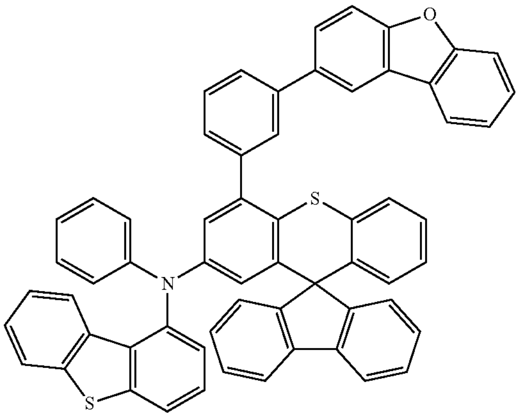
A-54
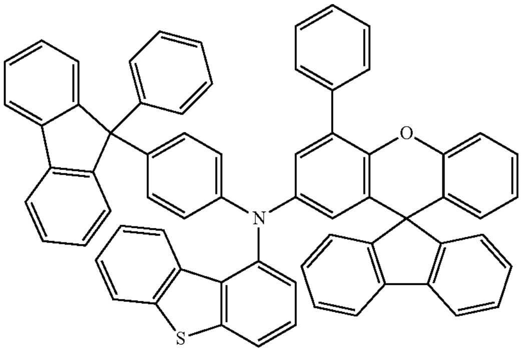
A-55
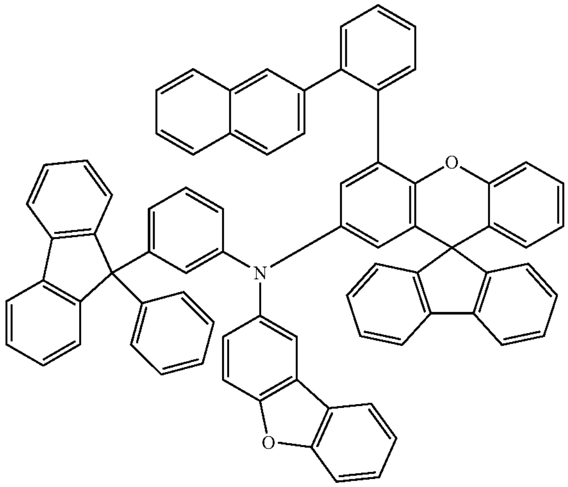

-continued
A-56
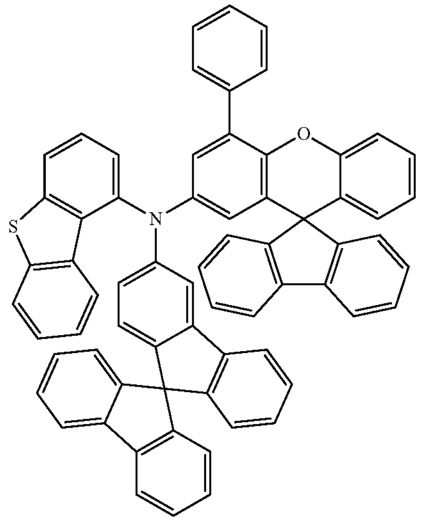
A-57
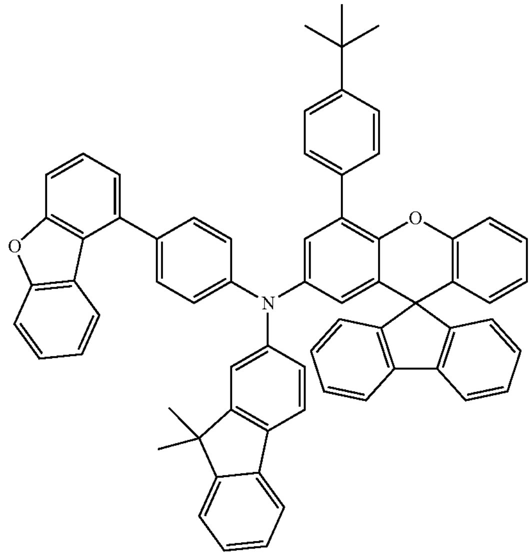
A-58
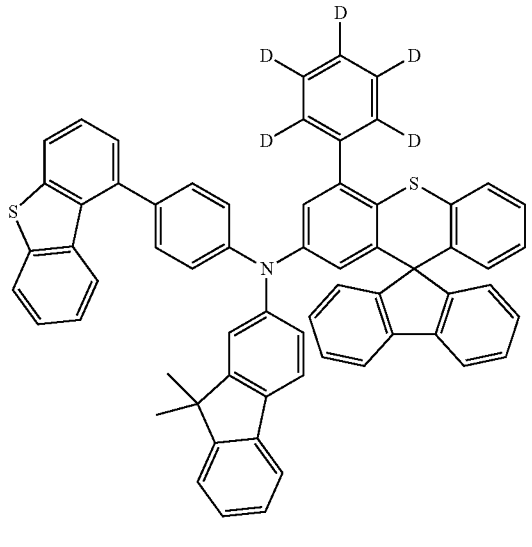
-continued
A-59
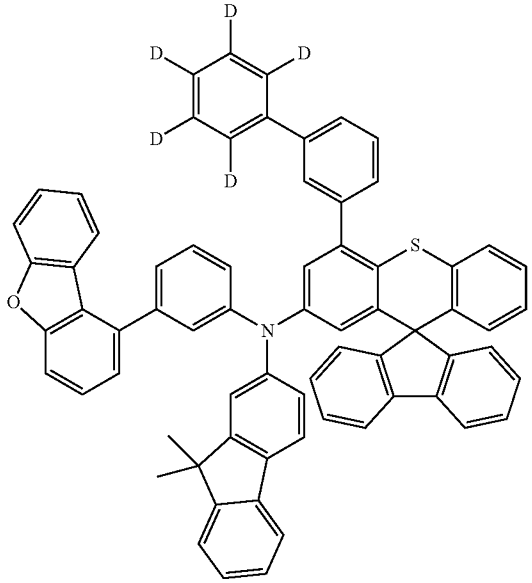
A-60
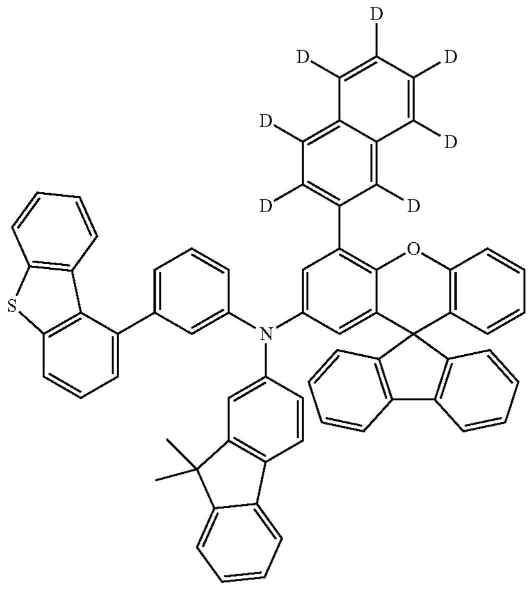

-continued
A-61
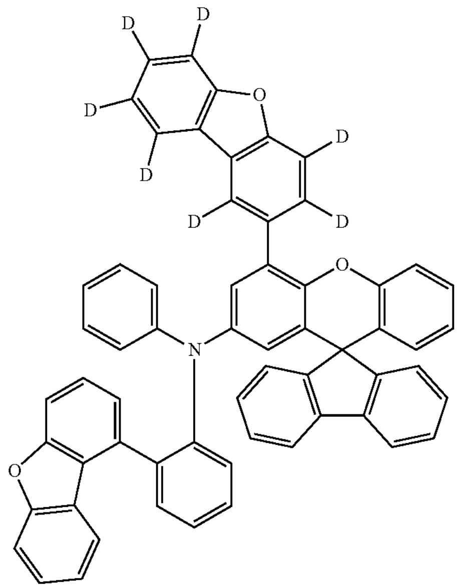
A-62
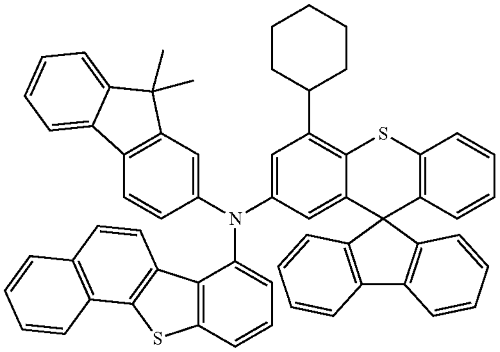
A-63
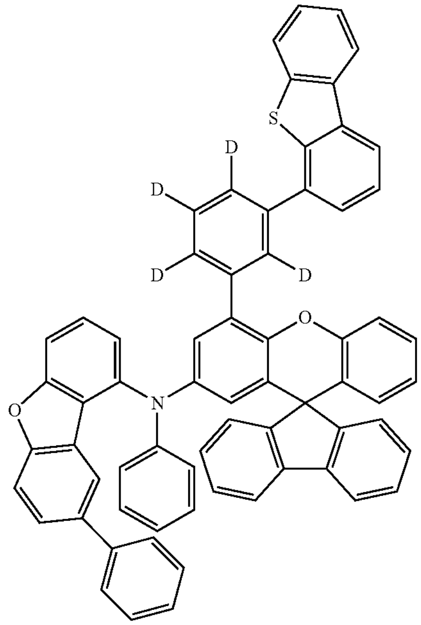
-continued
A-64
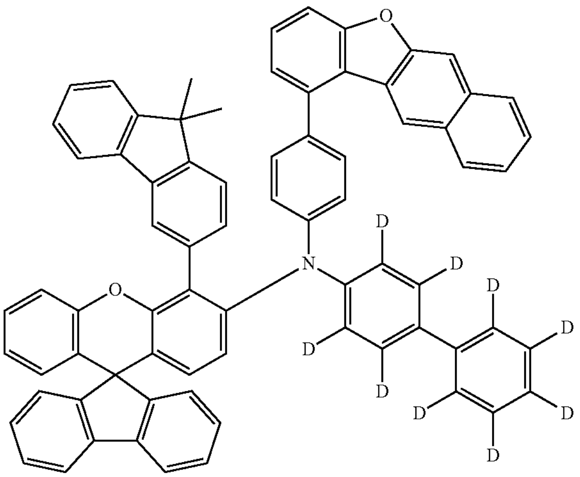
A-65
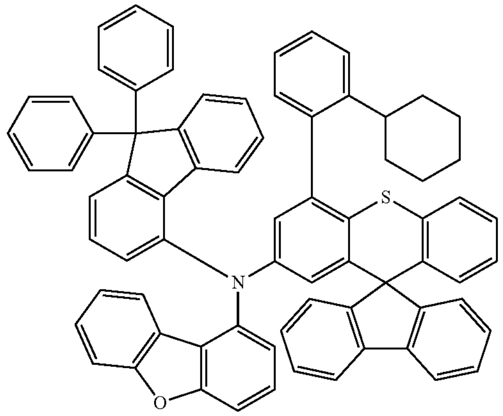
A-66
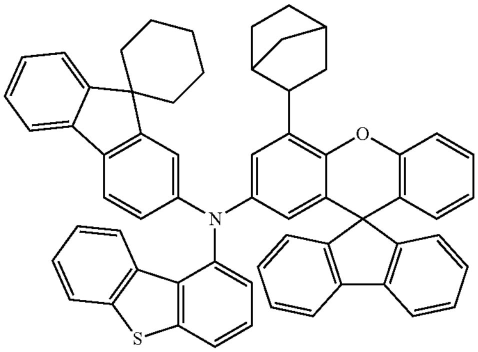

-continued
A-67
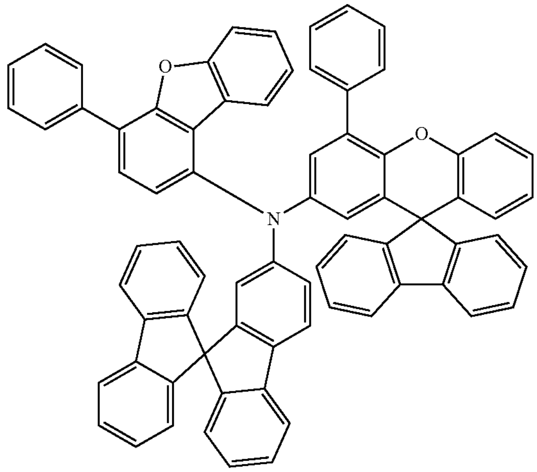
A-68
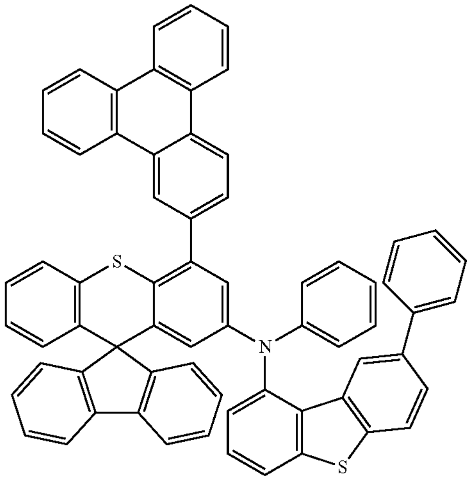
A-69
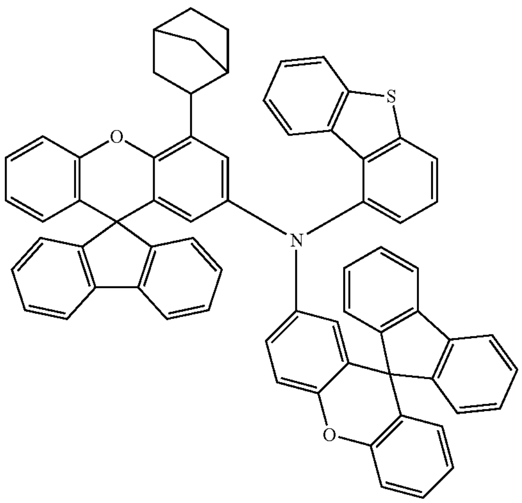
-continued
A-70
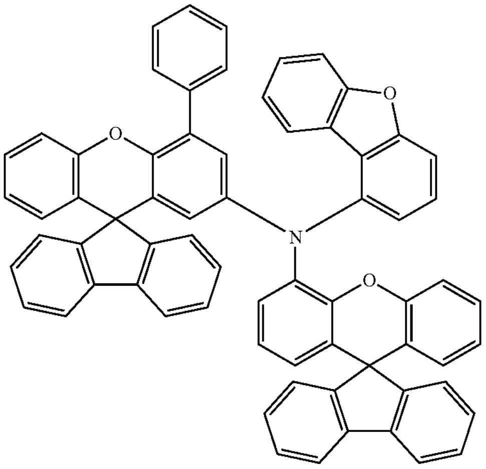
A-71
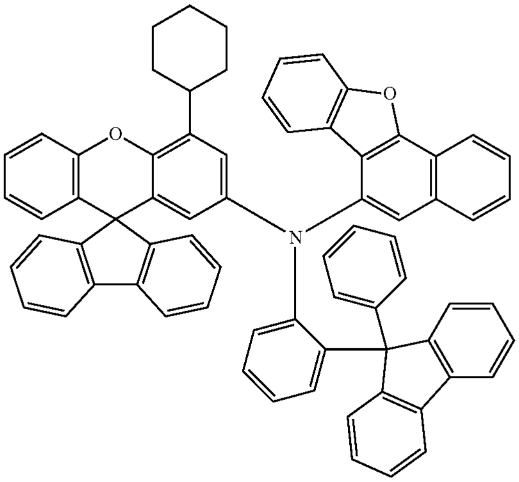
A-72
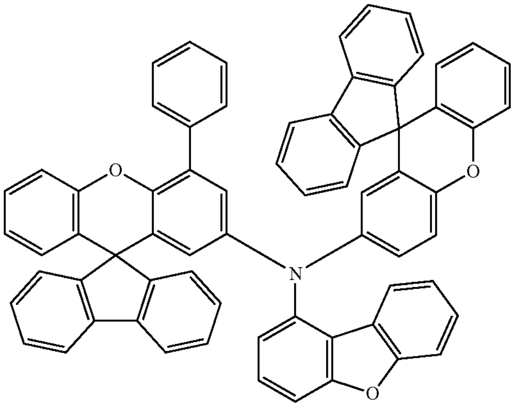

-continued
A-73
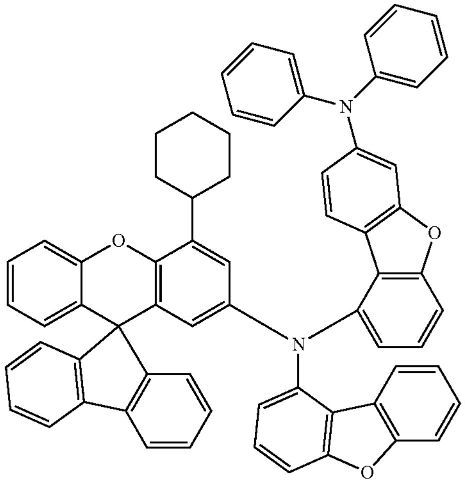
A-74
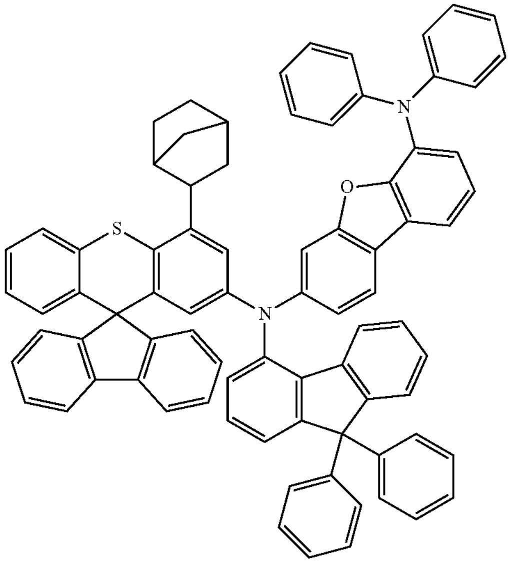
-continued
A-75
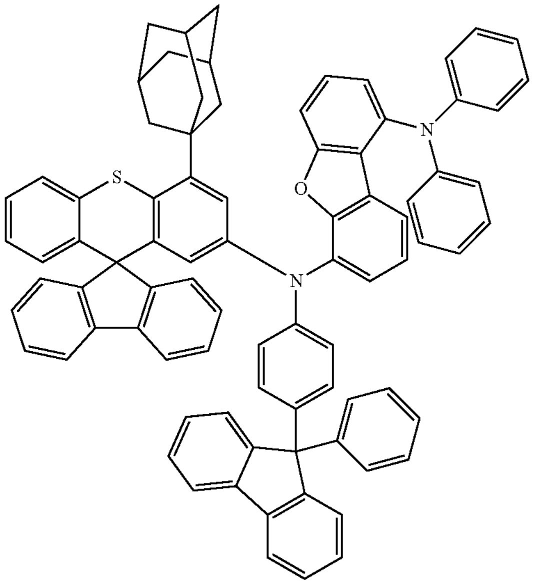
A-76
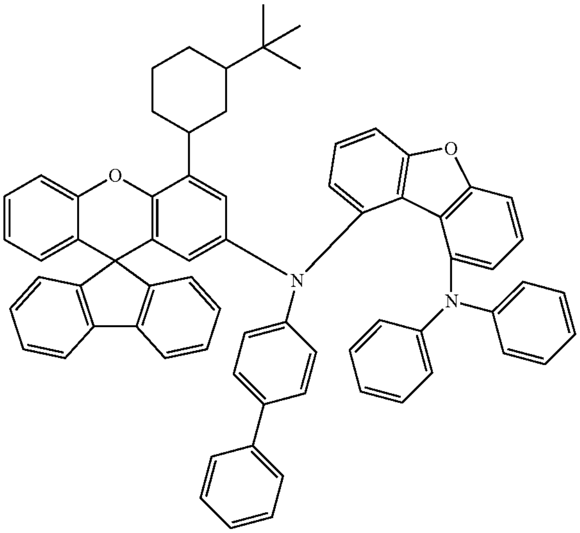

-continued
A-77
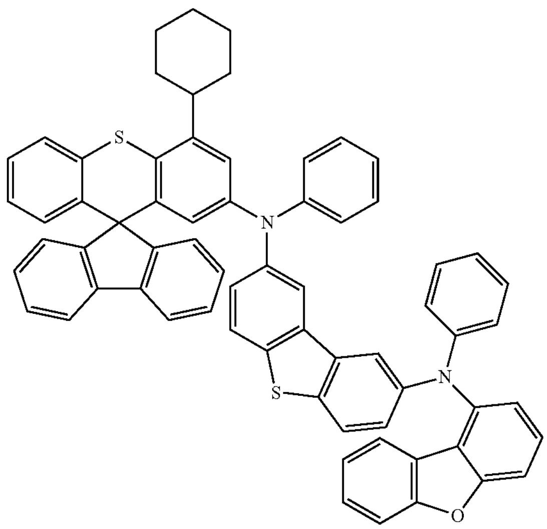
A-78
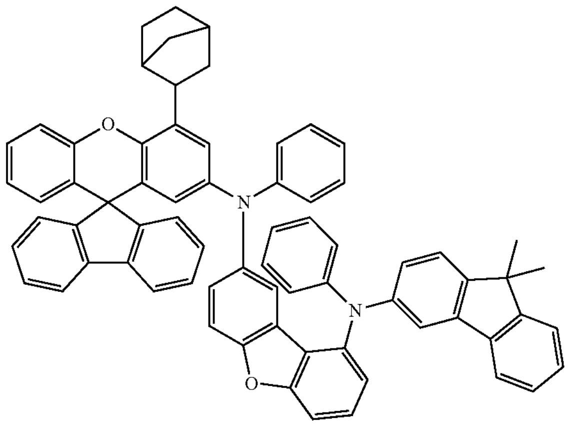
A-79
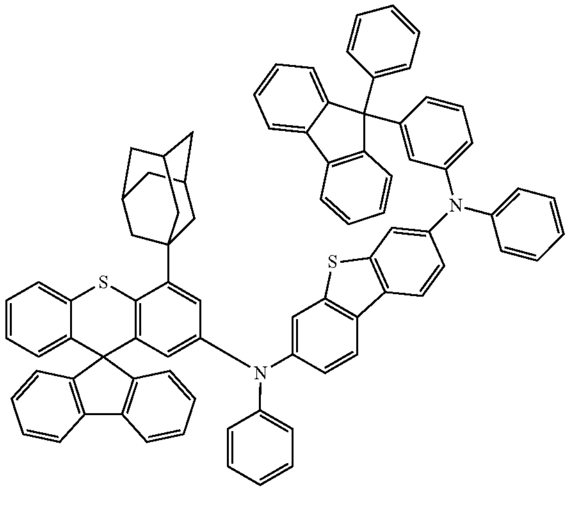
-continued
A-80
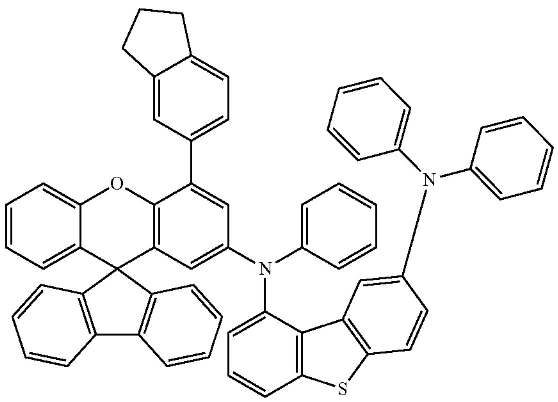
A-81
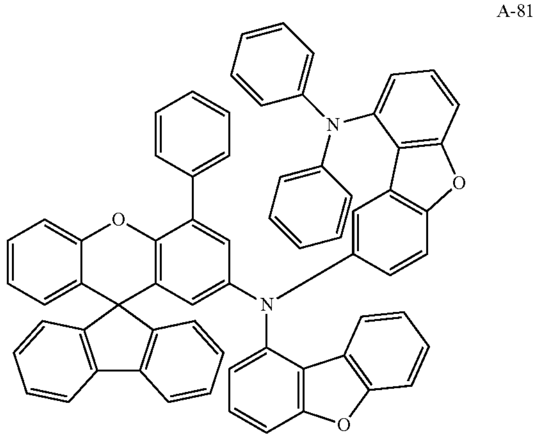
A-82
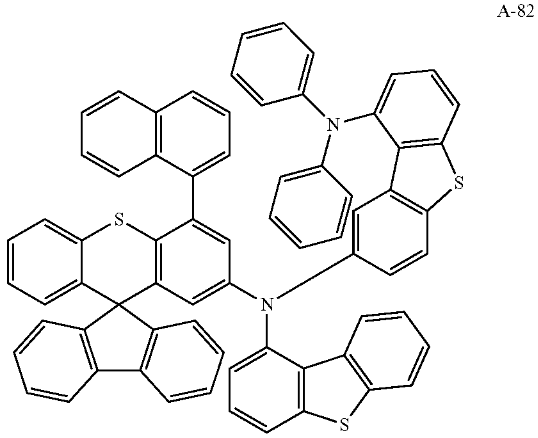

-continued
A-83
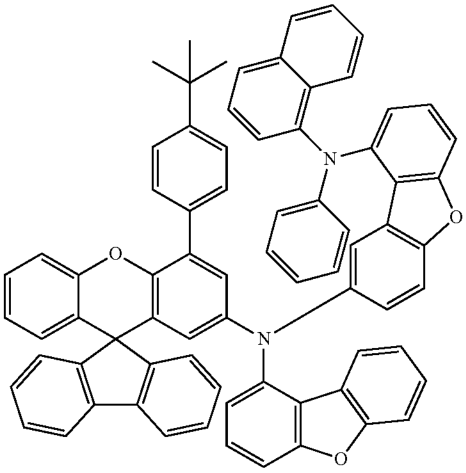
A-84
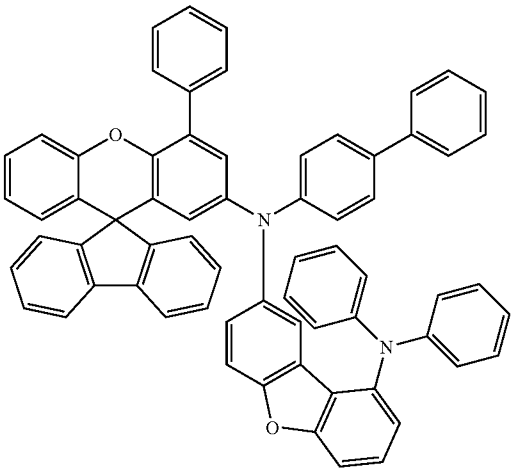
A-85
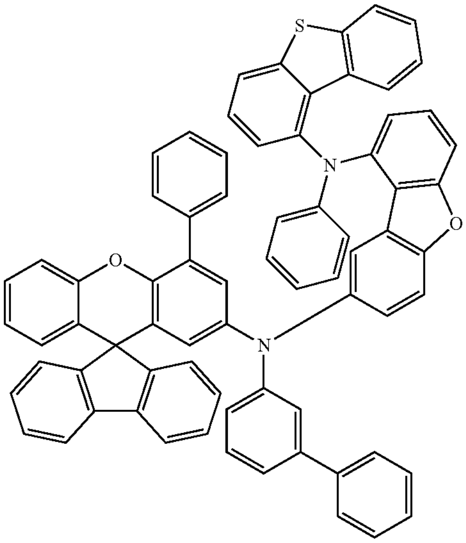
-continued
A-86
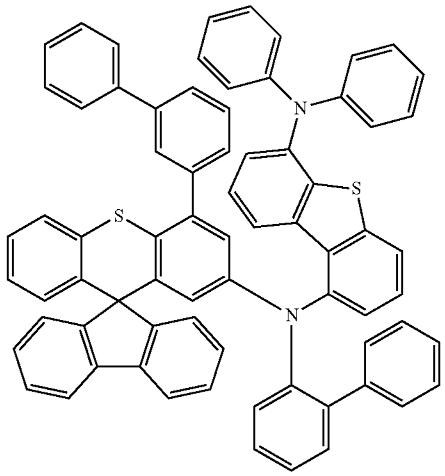
A-87
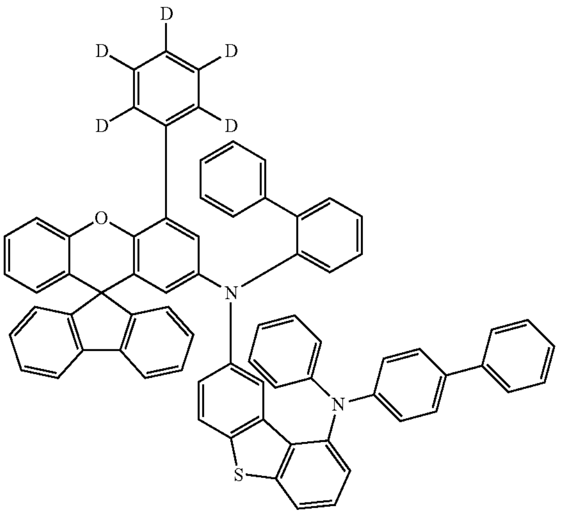
A-88
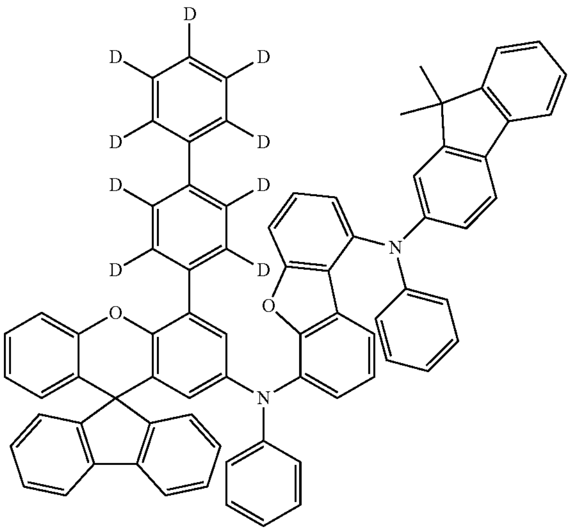

-continued
A-89
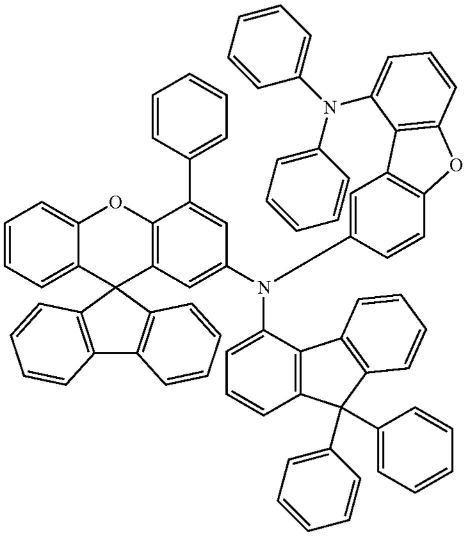
A-90
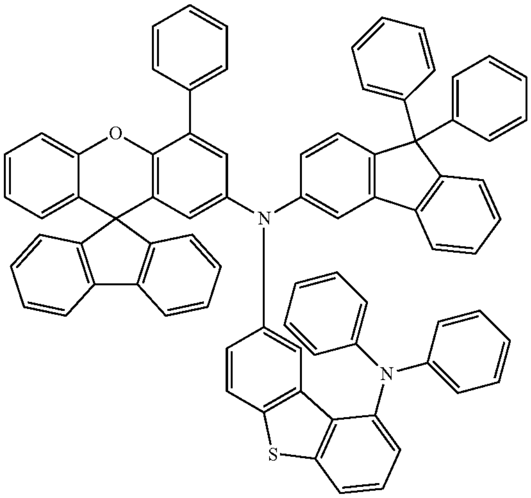
A-91
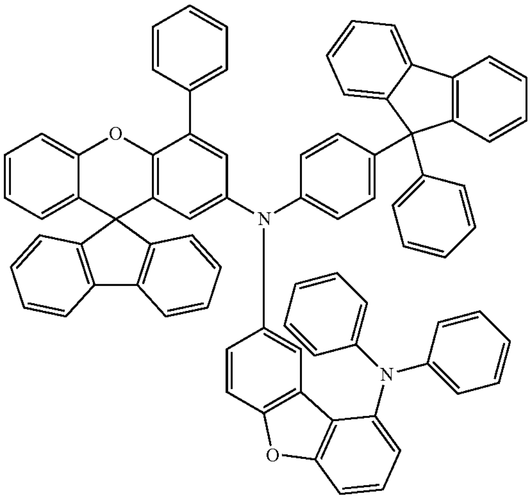
-continued
A-92
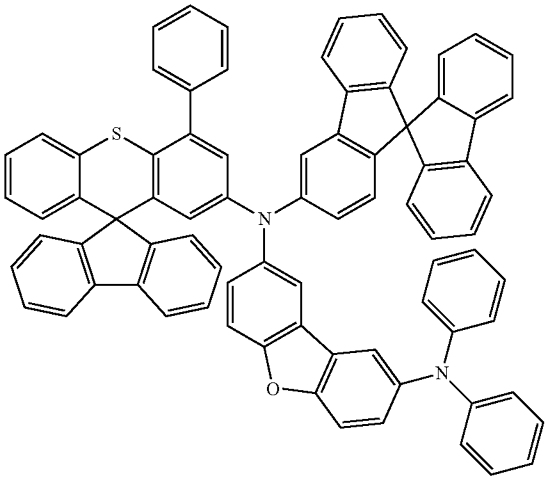
A-93
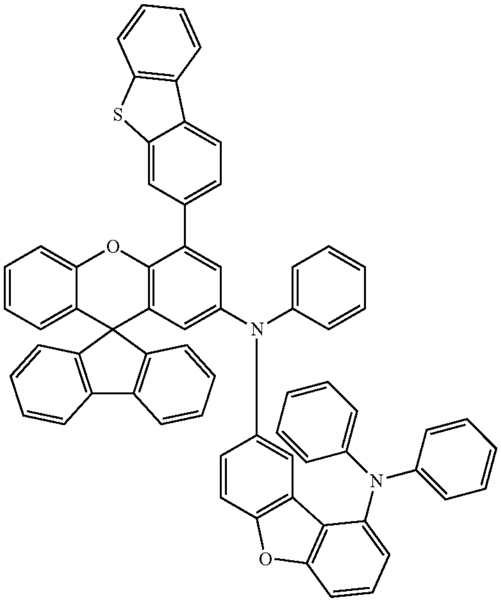

-continued
A-94
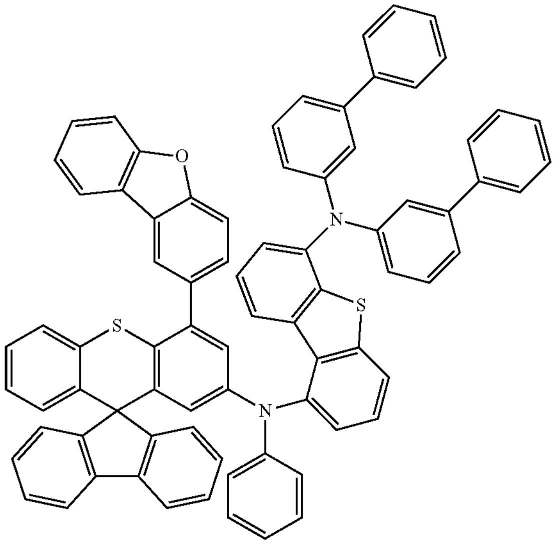
A-95
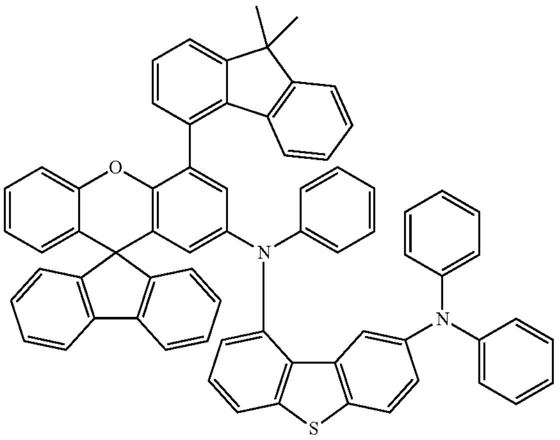
A-96
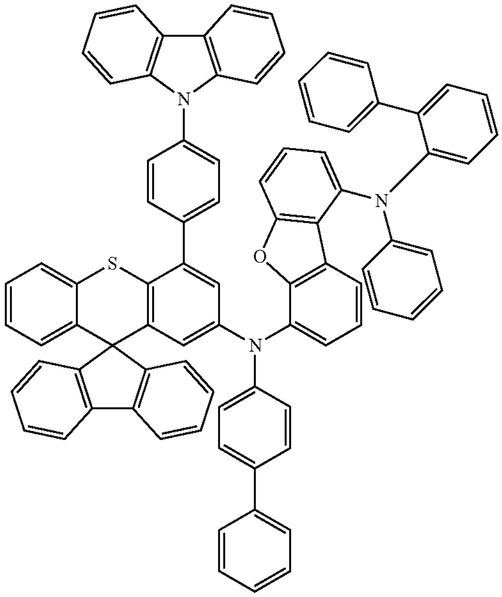
-continued
A-97
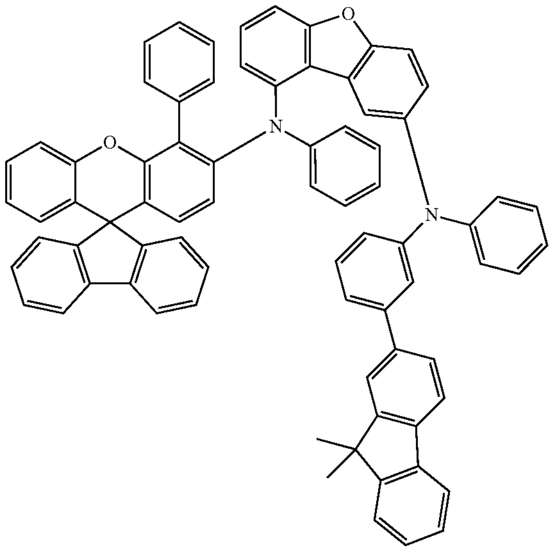
A-98
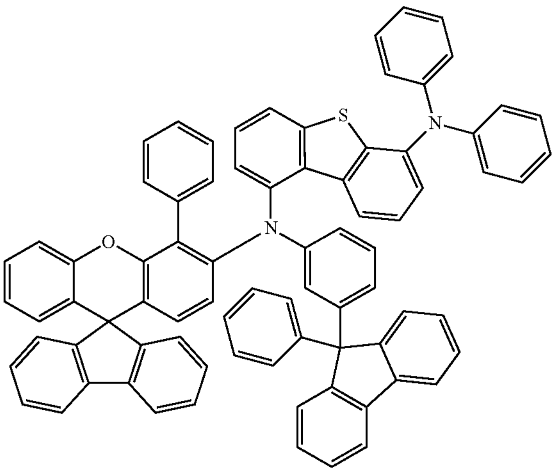
A-99
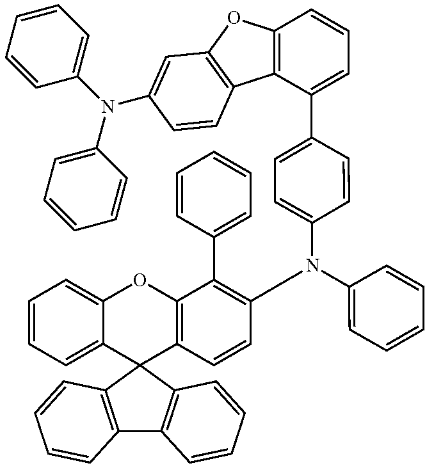

-continued
A-100
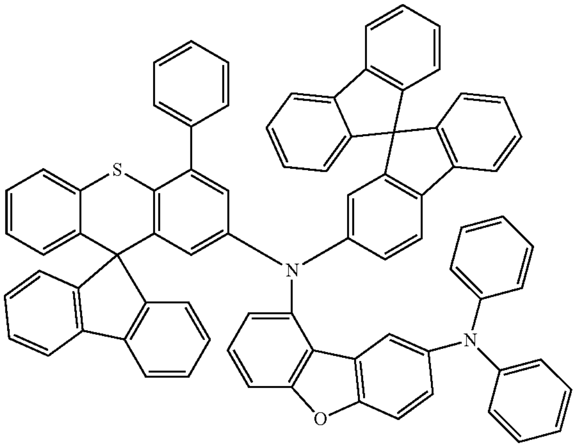
A-101
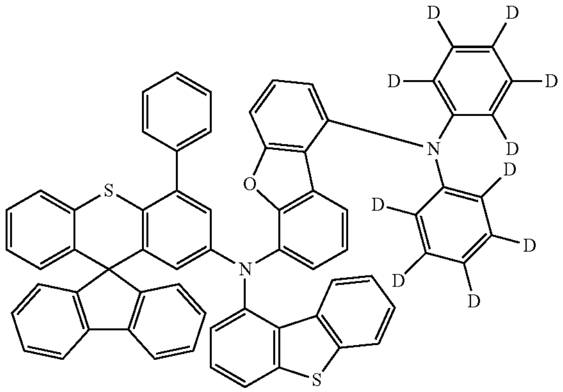
A-102
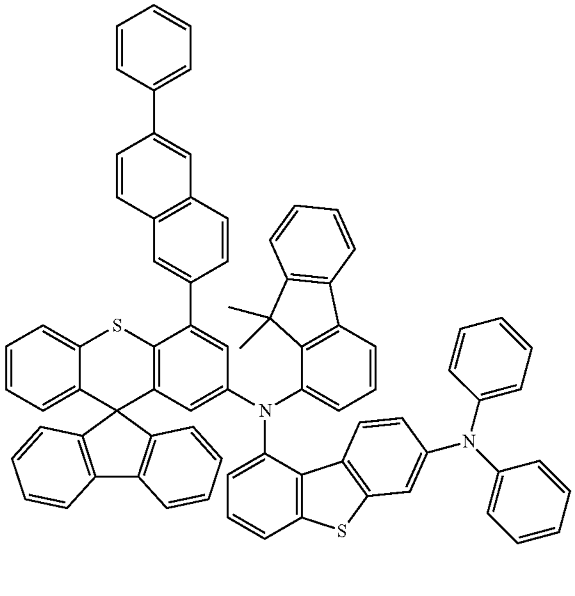
-continued
A-103
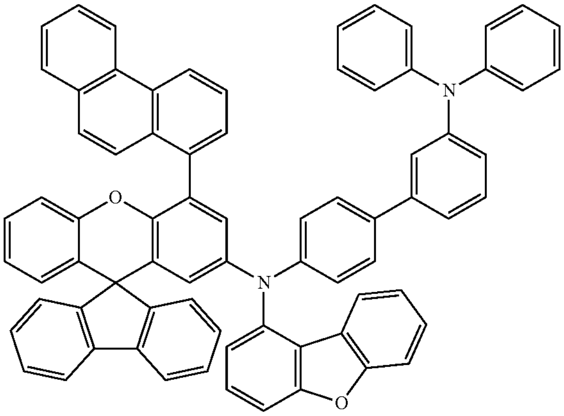
A-104
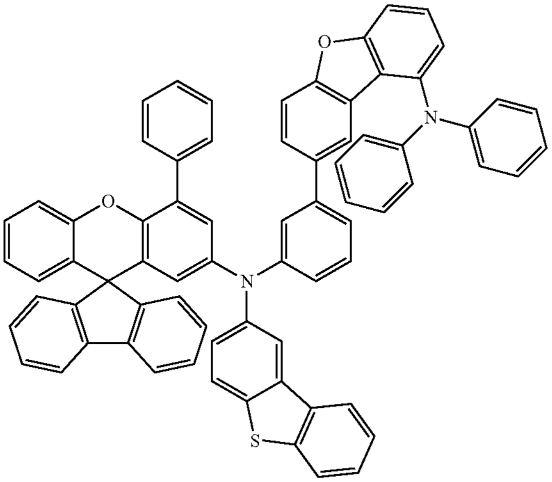
A-105
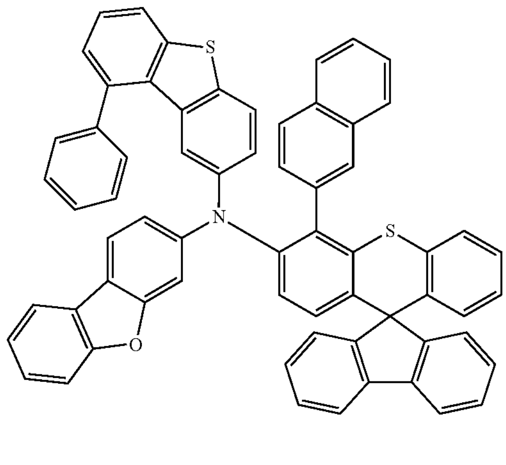

-continued
A-106
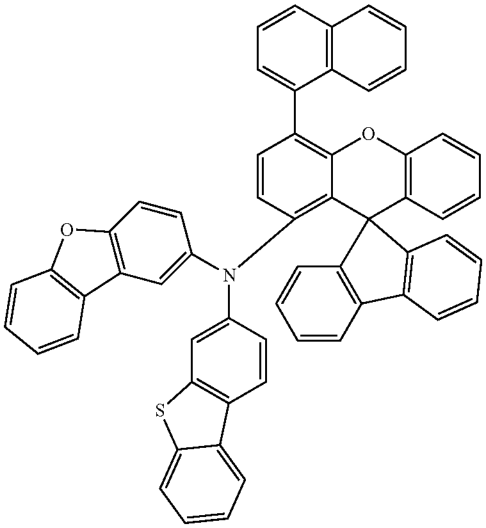
A-107
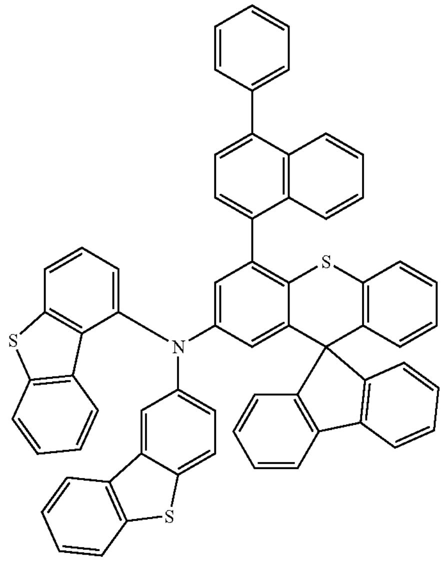
A-108
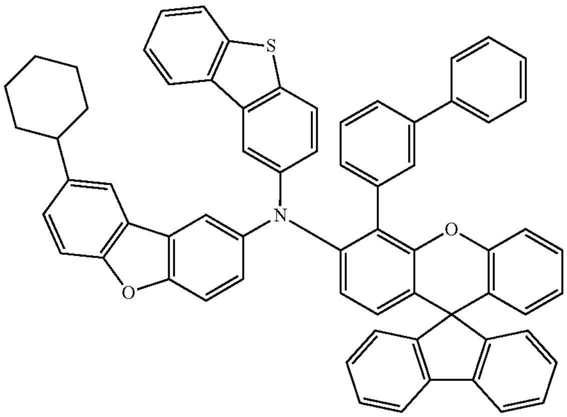
-continued
A-109
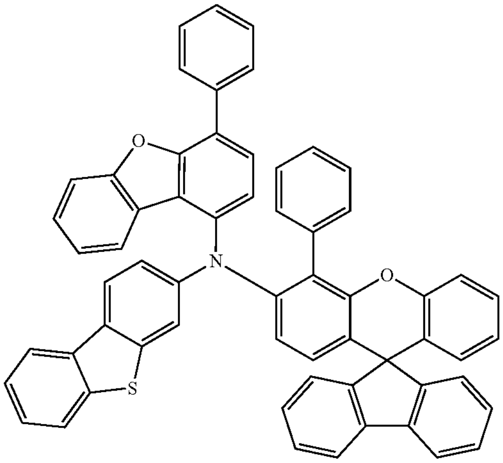
A-110
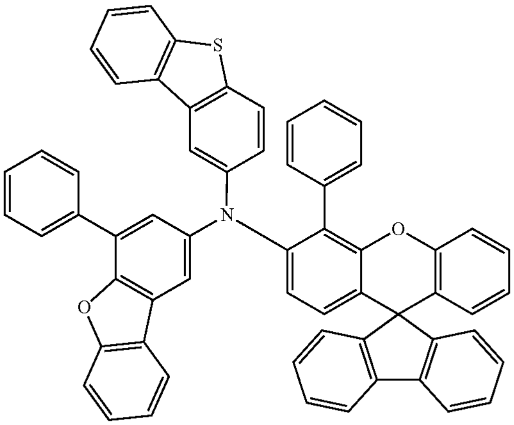
A-111
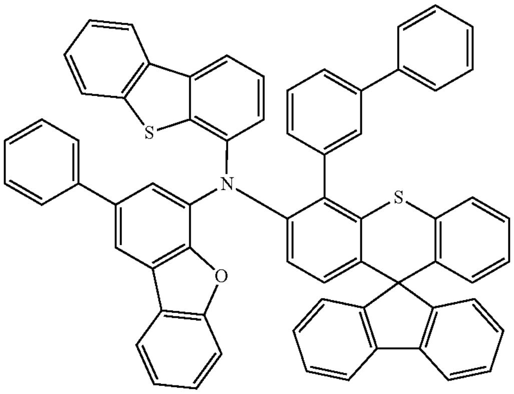

-continued

A-112

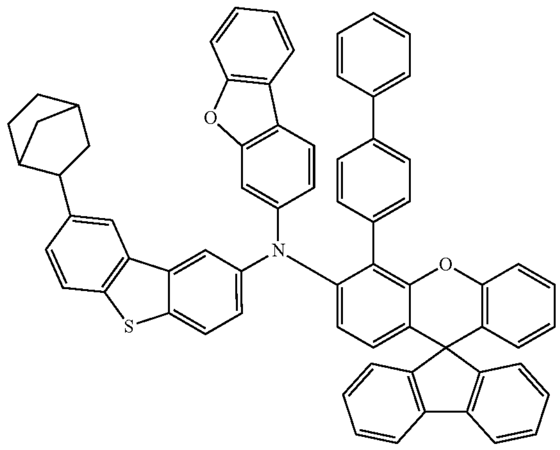

5. An organic electronic element comprising an anode, a cathode, and an organic material layer formed between the anode and the cathode, wherein the organic material layer comprises a single compound or 2 or more compounds represented by Formula A of claim 1.

6. The organic electronic element of claim 5, wherein the organic material layer comprises at least one of a hole injection layer, a hole transport layer, an emitting auxiliary layer, an emitting layer, an electron transport auxiliary layer, an electron transport layer, and an electron injection layer.

7. The organic electronic element of claim 5, wherein the organic material layer is an emitting auxiliary layer.

8. The organic electronic element of claim 5, wherein the organic electronic device further comprises a light efficiency enhancing layer formed on at least one surface of the anode and the cathode, the surface being opposite to the organic material layer.

9. The organic electronic element of claim 5, wherein the organic material layer comprises 2 or more stacks including a hole transport layer, an emitting layer, and an electron transport layer sequentially formed on the anode.

10. The organic electronic element of claim 9, wherein the organic material layer further comprises a charge generation layer formed between the 2 or more stacks.

11. An electronic device comprising a display device comprising the organic electronic element of claim 5; and a control unit for driving the display device.

12. An electronic device according to claim 11, wherein the organic electronic element is at least one of an OLED, an organic solar cell, an organic photo conductor(OPC), organic transistor (organic TFT) and an element for mono-chromic or white illumination.

13. A method of reusing the compound of Formula A of claim 1 in a manufacturing process of an organic light emitting device, comprising:

- a step of depositing an organic light emitting material including the compound of Formula A to a deposition apparatus;
- a step of recovering the organic light emitting material from the deposition apparatus as a crude material;
- a step of removing impurities from the crude organic light emitting material; and
- a step of recovering the purified organic light emitting material with a purity of 99.9% or more.

* * * * *